United States Patent
Luo et al.

(10) Patent No.: US 12,390,421 B2
(45) Date of Patent: Aug. 19, 2025

(54) ZWITTERIONIC DENDRITIC AMPHIPHILES, ZWITTERIONIC DENDRIMERS, ZWITTERIONIC TELODENDRIMERS, NANOCARRIERS COMPRISING SAME, AND METHODS OF MAKING AND USING SAME

(71) Applicant: The Research Foundation for the State University of New York, Syracuse, NY (US)

(72) Inventors: Juntao Luo, Jamesville, NY (US); Lili Wang, Syracuse, NY (US); Changying Shi, Jamesville, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 240 days.

(21) Appl. No.: 16/489,609

(22) PCT Filed: Feb. 28, 2018

(86) PCT No.: PCT/US2018/020316
§ 371 (c)(1),
(2) Date: Aug. 28, 2019

(87) PCT Pub. No.: WO2018/160759
PCT Pub. Date: Sep. 7, 2018

(65) Prior Publication Data
US 2020/0009069 A1    Jan. 9, 2020

Related U.S. Application Data

(60) Provisional application No. 62/464,892, filed on Feb. 28, 2017.

(51) Int. Cl.
*A61K 9/51*      (2006.01)
*A61K 45/06*   (2006.01)
*A61K 49/00*   (2006.01)
*B82Y 5/00*     (2011.01)

(52) U.S. Cl.
CPC .......... *A61K 9/5169* (2013.01); *A61K 9/5138* (2013.01); *A61K 9/5146* (2013.01); *A61K 45/06* (2013.01); *A61K 49/0054* (2013.01); *A61K 49/0093* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 5,712,326 | A | * | 1/1998 | Jones ...................... C08L 33/12 524/916 |
| 2011/0286915 | A1 | | 11/2011 | Lam et al. |
| 2013/0164369 | A1 | | 6/2013 | Lam et al. |
| 2013/0165636 | A1 | | 6/2013 | Luo et al. |
| 2014/0363371 | A1 | | 12/2014 | Luo et al. |
| 2015/0056139 | A1 | | 2/2015 | Luo et al. |

FOREIGN PATENT DOCUMENTS

WO    2016/057657 A1    4/2016

OTHER PUBLICATIONS

Jin, Q., et al., Zwitterionic drug nanocarriers: A biomimetic strategy for drug delivery, Colloids and Surfaces B: Biointerfaces, Jul. 19, 2014, vol. 124, pp. 80-86.

* cited by examiner

*Primary Examiner* — Tigabu Kassa
(74) *Attorney, Agent, or Firm* — Peter Fallon; Lance Reich

(57) ABSTRACT

Zwitterionic dendrimers and zwitterionic polymers and methods of making the zwitterionic dendrimers/polymers are provided herein. Also provided are amphiphilic dendrimers and amphiphilic telodendrimers with one or more zwitterionic dendron/polymer/linear group(s)/moiety(s) covalently bonded thereto. The amphiphilic dendrimers and amphiphilic telodendrimers are useful in protein binding and drug delivery. The amphiphilic dendrimers and amphiphilic telodendrimers are used in methods of treatment and/or imaging.

11 Claims, 79 Drawing Sheets

GPC$_8$-Arg$_4$C17$_4$

Protein binding janus-type amphiphiles

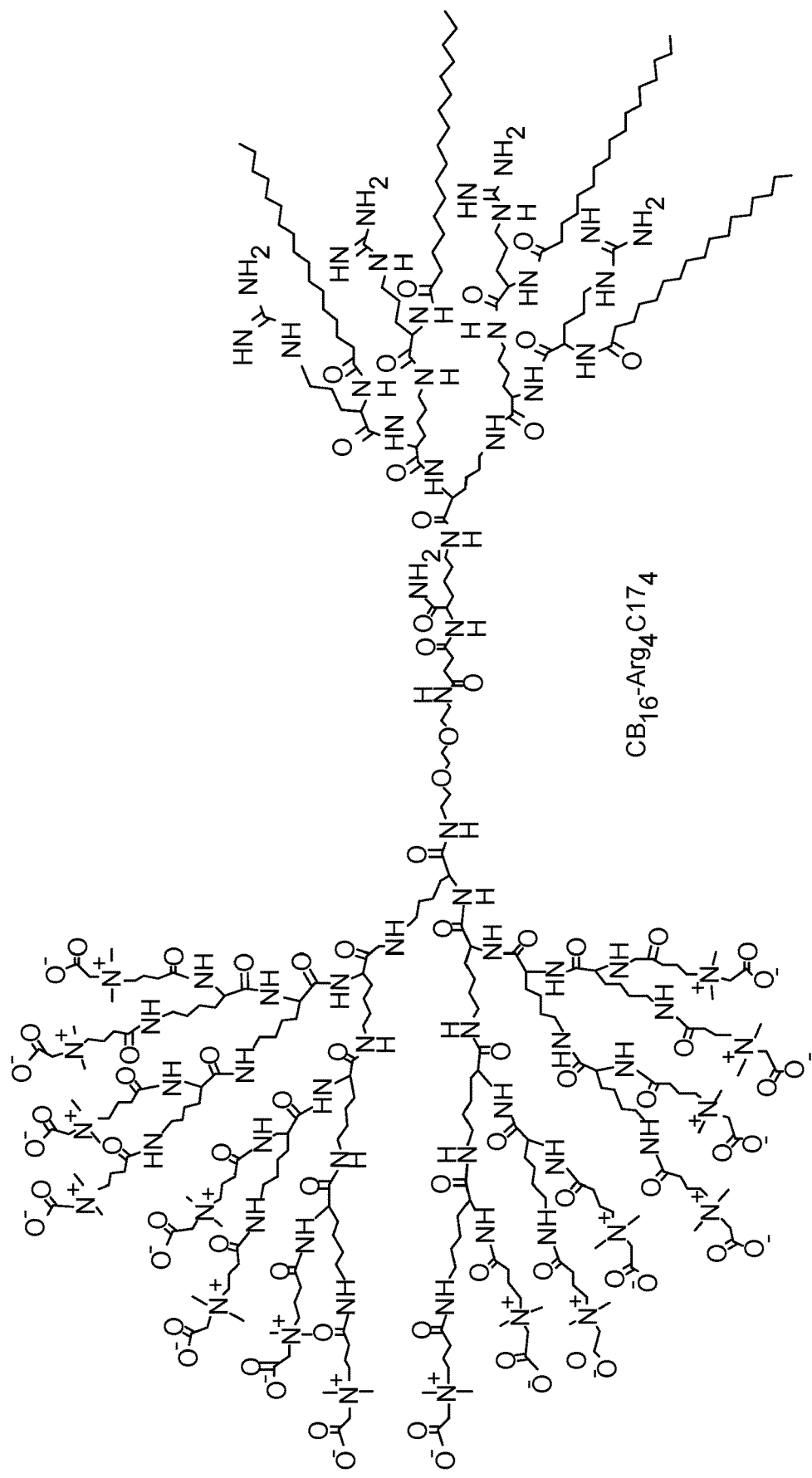
FIG. 11A (Cont'd) Protein binding janus-type amphiphiles
$CB_{16}$-$Arg_4$$C17_4$ Protein binding janus-type amphiphiles CB2₁₆-Arg₄PMB₄

Protein binding janus-type amphiphiles

GPC$_8$-Arg$_4$C17$_4$ $CB_{16}$-$Arg_4C17_4$

Protein binding janus-type amphiphiles

GPC$_8$-Rh$_4$

Drug binding janus-type amphiphiles

Drug binding janus-type amphiphiles $CB_{16}$-$Rh_4$

Phosphorylcholine (PC) Janus dendrimer for small molecular drug loading

PC Janus dendrimer with VE functionality for drug delivery

PC Janus dendrimer with hybrid Rf and CA functionalities for drug delivery

PC Janus dendrimer with Rf functionality for drug delivery

PC Janus dendrimer with hybrid arginine and Rf functionalities

PC Janus dendrimer with hybrid arginine and Rf functionalities

PC Janus dendrimer with segregated CA and CHO functionalities

PC Janus dendrimer with segregated CA and CHO functionalities

PC Janus dendrimer with segregated CA and CHO functionalities

PC Janus dendrimer with segregated carboxylic acid and CA functionalities for drug chelation and drug loading PC Janus dendrimer with hybrid amine and hydrophobic functionalities PC Janus dendrimer with hybrid arginine and CHO functionalities PEG<sup>5k</sup>(Arg-L-CHO)<sub>4</sub>

PC Janus dendrimer with hybrid amine and hydrophobic functionalities

PC Janus dendrimer with hybrid arginine and hydrophobic functionalities

PC Janus dendrimer with hybrid arginine and hydrophobic functionalities

1. α-Lactalbumin (α-LA)
2. α-LA-PEG$^{5k}$-(ArgC17)$_4$
3. α-LA-GPC$_8$-(ArgC17)$_4$ 1. pH low insertion peptide (pHLIP)
2. pHLIP-PEG$^{5k}$-(ArgC17)$_4$
3. pHLIP-GPC$_8$-(ArgC17)$_4$ 1. Insulin
2. Insulin-PEG$^{5k}$-(ArgC17)$_4$
3. Insulin-GPC$_8$-(ArgC17)$_4$

ZWITTERIONIC DENDRITIC AMPHIPHILES, ZWITTERIONIC DENDRIMERS, ZWITTERIONIC TELODENDRIMERS, NANOCARRIERS COMPRISING SAME, AND METHODS OF MAKING AND USING SAME

CROSS REFERENCE TO RELATED APPLICATIONS

This application claims priority to U.S. Provisional Application No. 62/464,892, filed on Feb. 28, 2017, the disclosure of which is hereby incorporated by reference.

STATEMENT REGARDING FEDERALLY SPONSORED RESEARCH OR DEVELOPMENT

This invention was made with government support under contract no. EB019607 awarded by National Institutes of Health. The government has certain rights in the invention.

FIELD OF THE DISCLOSURE

The disclosure generally relates to zwitterionic amphiphiles and zwitterionic telodendrimers.

BACKGROUND OF THE DISCLOSURE

In vivo application of nanoparticles is challenged by the rapid elimination from circulation due to their interactions with biological systems. To maintain nanoparticle integrity prior to their accumulation at therapeutic sites, nonspecific adsorption of proteins and interactions with phagocytes need to be minimized. A control over the interaction of nanomaterials with biological systems is primarily governed by physicochemical feature of nanoparticle surface. Hydrophilic polymers, e.g. polyethylene glycol (PEG), are most commonly employed as the shell of nanoparticles. The chain length and packing density of PEG on the surface of a nanoparticle is critical for the in vivo stability of nanoparticle. It was also reported that the repeated application of PEGylated nanoparticle may induce anti-PEG antibody production in animal, which may significantly accelerate the clearance from blood circulation. An alternative strategy to achieve stealth property is through the modification of nanoparticle with non-fouling polymers.

Dendritic polymers are perfectly branched and monodisperse macromolecules with layered architecture. Considerable variety in composition is attainable through the incorporation of different functional groups on the periphery of dendrons, inducing predictable properties and diverse applications. However, dendrimer functionality rely heavily on the surface functionality for drug conjugation. Dendrimers can be constructed asymmetrically by sequential substitution and functionalization of different fractions of the dendrons to acquire multifunctionality for the conjugation of different drugs or targeting ligand. The physical pockets within dendrimers are generally small and insufficient for achieving high drug loading capacity and controlled drug release. In addition, dendrimers are usually not able to self-assemble into nanoparticles in a controlled manner for drug encapsulation.

SUMMARY OF THE DISCLOSURE

The present disclosure provides zwitterionic dendrimers and zwitterionic polymers and methods of making the zwitterionic dendrimers/polymers. Also provided are amphiphilic dendrimers and amphiphilic telodendrimers comprising one or more zwitterionic dendron/polymer/linear group(s)/moiety(s) and methods of using the amphiphilic dendrimers and amphiphilic telodendrimers (for example, in protein binding and drug delivery).

This disclosure describes, for example, production of zwitterionic amphiphiles which integrate the therapeutic binding and anti-fouling moieties into a single dendrimer. A novel combination of solid-phase peptide and liquid-phase peptide synthesis was developed for synthesizing the zwitterionic amphiphiles. The unique structure of zwitterionic amphiphiles enable them to self-assemble with therapeutics into nanocarriers with zwitterionic surface, displaying non-fouling property, and increase in vitro and in vivo stability of nanotherapeutics for targeted drug delivery.

In an aspect, the present disclosure provides zwitterionic linear compounds, zwitterionic polymers, and zwitterionic dendrimers. The zwitterionic linear compounds, zwitterionic polymers, and zwitterionic dendrimers can be discrete compounds or can be used to form one or more zwitterionic dendron groups on an amphiphilic dendrimer or amphiphilic telodendrimer. In various examples, the backbone of the zwitterionic linear compounds and/or zwitterionic dendrimers are formed from amide bonds, ester bonds, ether bonds, or a combination thereof.

In an aspect, the present disclosure provides amphiphilic dendrimers and amphiphilic telodendrimers comprising one or more zwitterionic groups (e.g., zwitterionic linear compounds, zwitterionic polymers (e.g., zwitterionic linear polymers), or a combination thereof) and one or more other dendrons (e.g., drug-binding and/or protein-binding dendrons. The amphiphilic dendrimers can be hybrid dendrimers with two distinct dendrons. The dendrimers are also referred to herein as Janis-type amphiphiles. The amphiphilic dendrimers and amphiphilic telodendrimers can form nanocarriers (e.g., single or multi-layer dendrimer micelle structures). The nanocarriers can comprise a hydrophilic layer, which can be an external layer, that comprises one or more zwitterionic groups. In an example, amphiphilic dendrimers and/or amphiphilic telodendrimers do not comprise any polyethylene glycol (PEG) groups and/or PEG moieties.

In an aspect, the present disclosure provides methods of making zwitterionic dendrimers and amphiphilic dendrimers/telodendrimers comprising one or more zwitterionic dendrons. In various examples, the methods comprise one or more solid-phase synthetic steps (e.g., one or more steps based on solid-phase peptide synthesis).

In an aspect, the present disclosure provides methods of making amphiphilic dendrimers and amphiphilic telodendrimers comprising one or more zwitterionic dendrons and one or more other dendrons (e.g., drug-binding and/or protein-binding dendrons). In various examples, the methods comprise one or more liquid-phase synthetic steps (e.g., one or more steps based on liquid-phase peptide synthesis). In various examples, the methods comprise one or more solid-phase synthetic steps (e.g., one or more steps based on solid-phase peptide synthesis), which are used for form zwitterionic dendrons, and one or more liquid-phase synthetic steps (e.g., one or more steps based on liquid-phase peptide synthesis).

In an aspect, the present disclosure provides nanocarriers comprising amphiphilic dendrimers and/or amphiphilic telodendrimers. In an embodiment, a composition comprises an aggregate of a plurality of the amphiphilic dendrimers and/or amphiphilic telodendrimers that form a nanocarrier having a hydrophobic core and a hydrophilic exterior. The nanocarriers may comprise dendrimers having a plurality of cross-linked groups (e.g., photo-crosslinked groups). In an embodiment, a composition comprises an aggregate of a plurality of the dendrimers and/or telodendrimers having a plurality of crosslinked groups (e.g., photo-crosslinked groups) that form a nanocarrier having a hydrophobic core and a hydrophilic exterior.

In an aspect, the present disclosure provides uses of dendrimers comprising one or more zwitterionic dendrons of the present disclosure. The dendrimers can be used, for example, in methods of treatment and/or imaging.

BRIEF DESCRIPTION OF THE DRAWINGS

For a fuller understanding of the nature and objects of the disclosure, reference should be made to the following detailed description taken in conjunction with the accompanying figures.

DETAILED DESCRIPTION OF THE DISCLOSURE

Figure 1A:
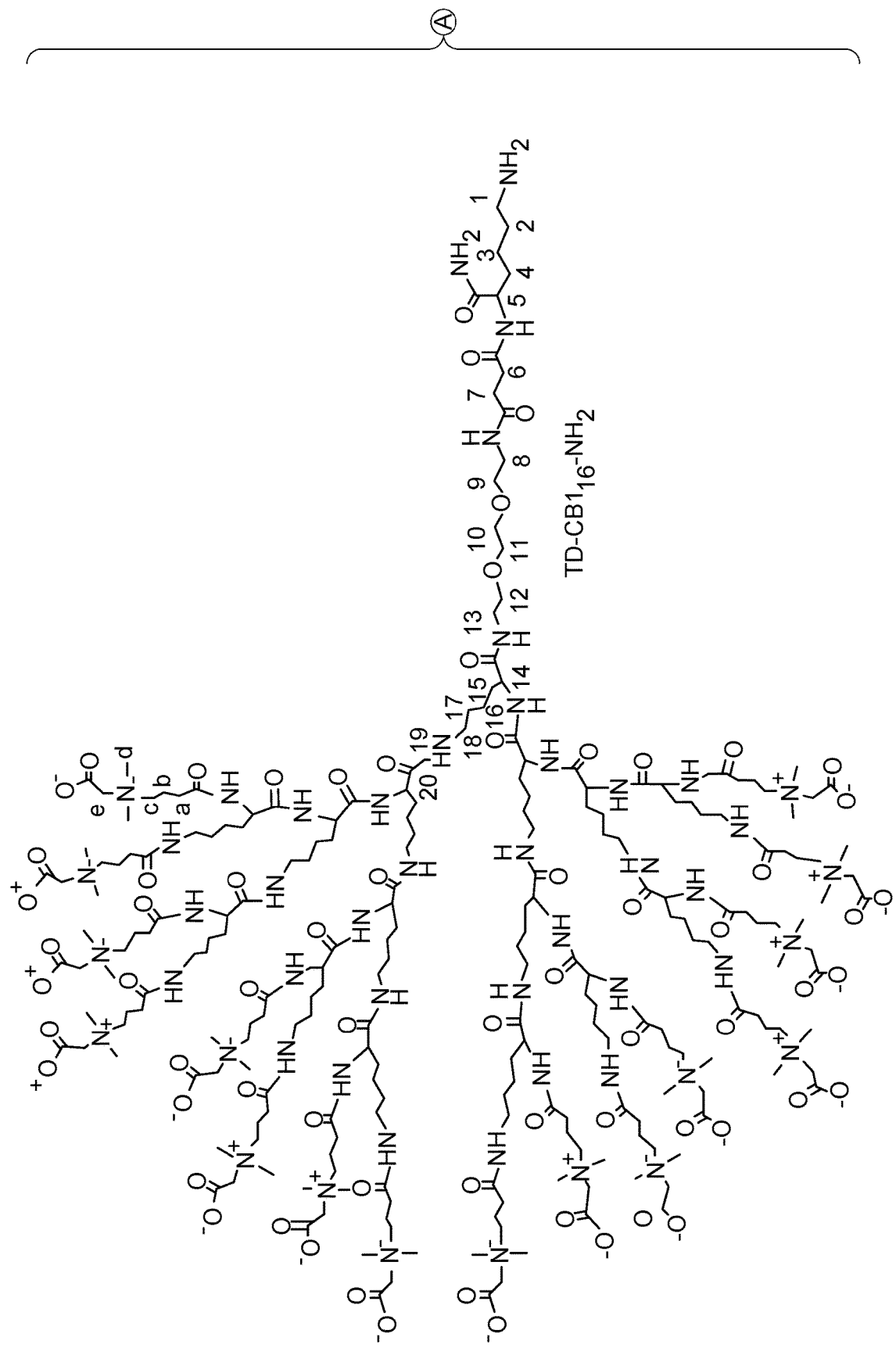
FIG. 1 shows $^1$H NMR spectra of D-$CB_{16}$—$NH_2$ (A) in DMSO-$d_6$ and D-$GPC_8$—$NH_2$ in $D_2O$ (B), recorded on 600 MHz.
Figure 1A:
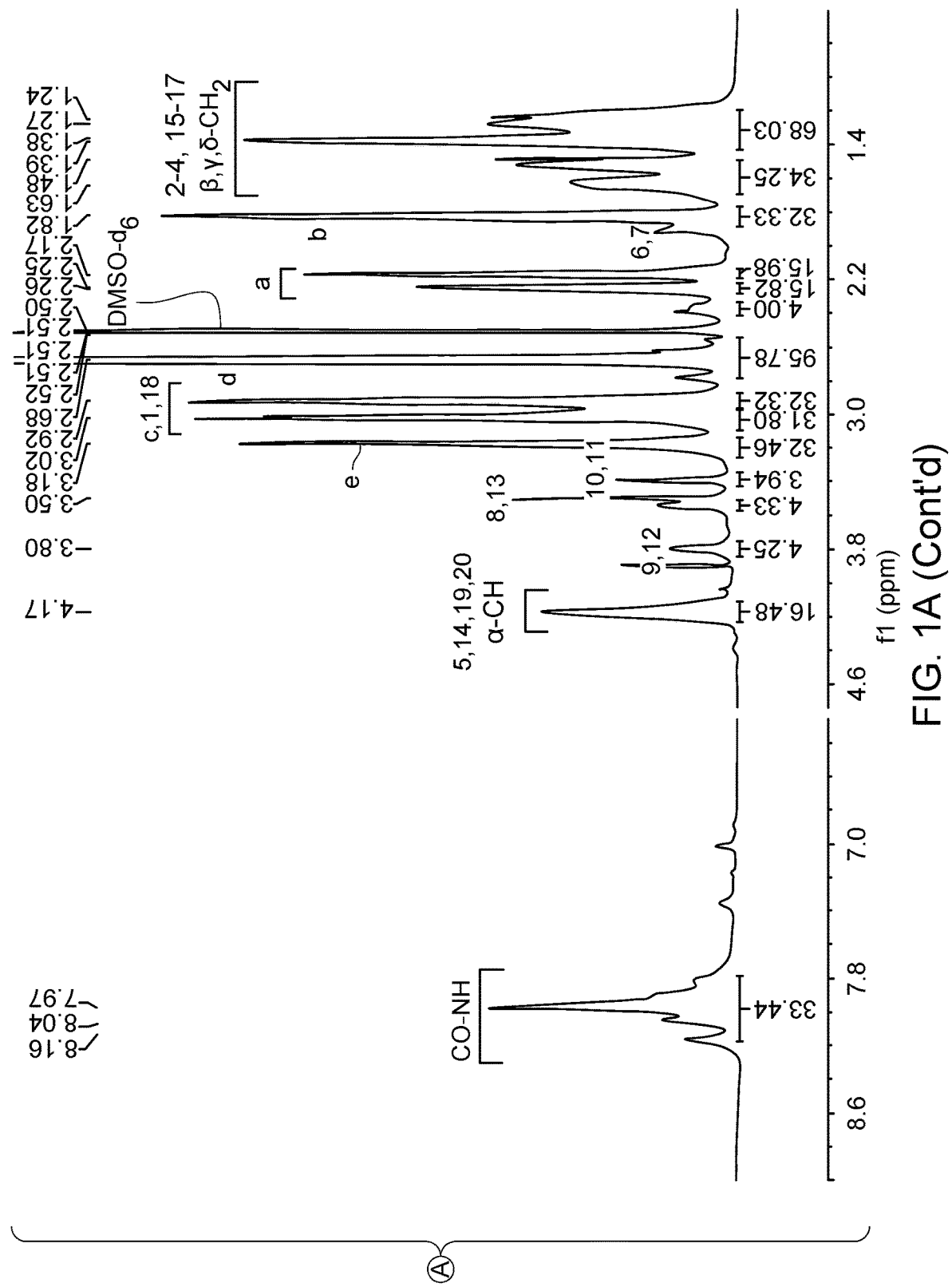
Figure 1B:
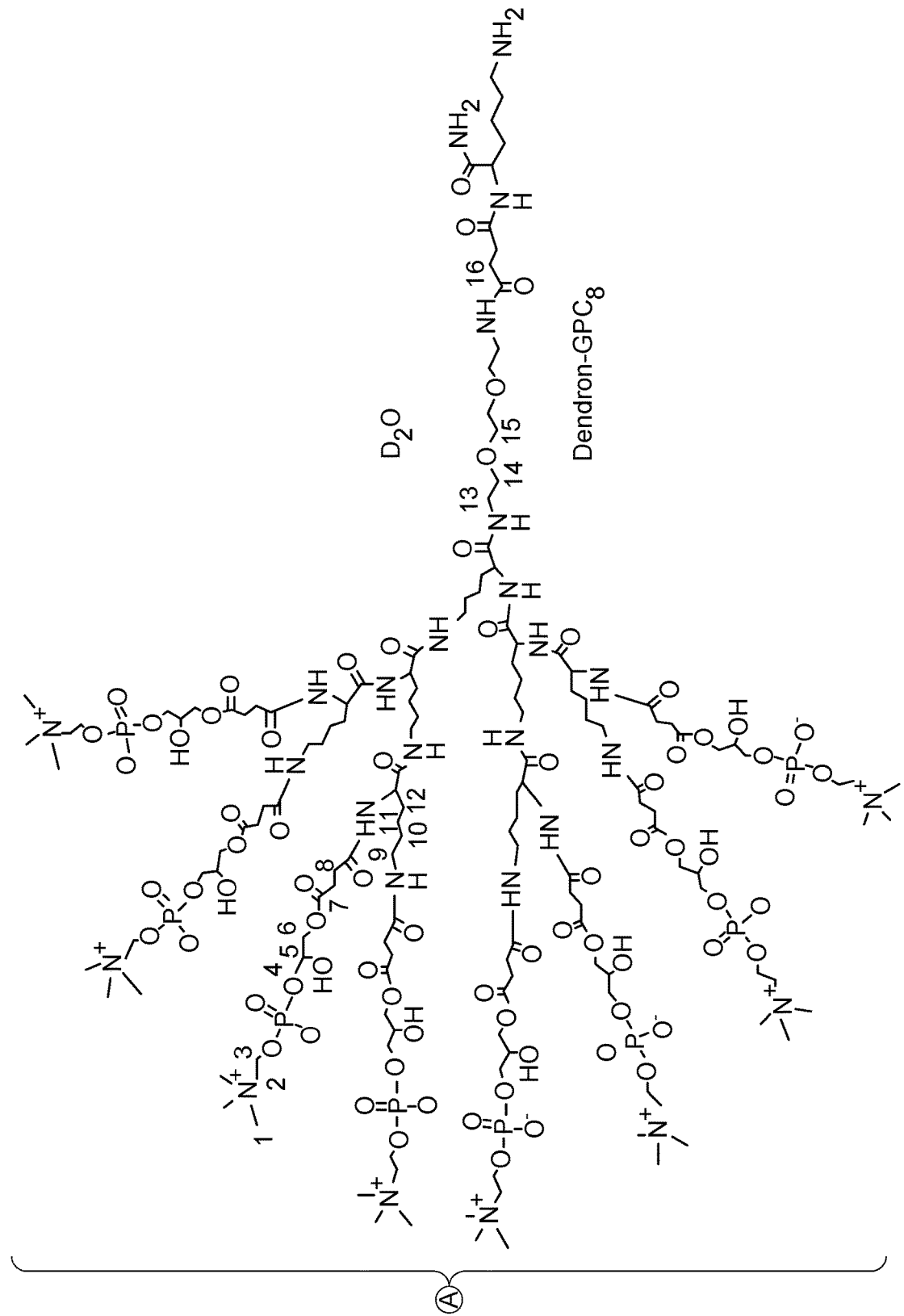
Figure 1B:
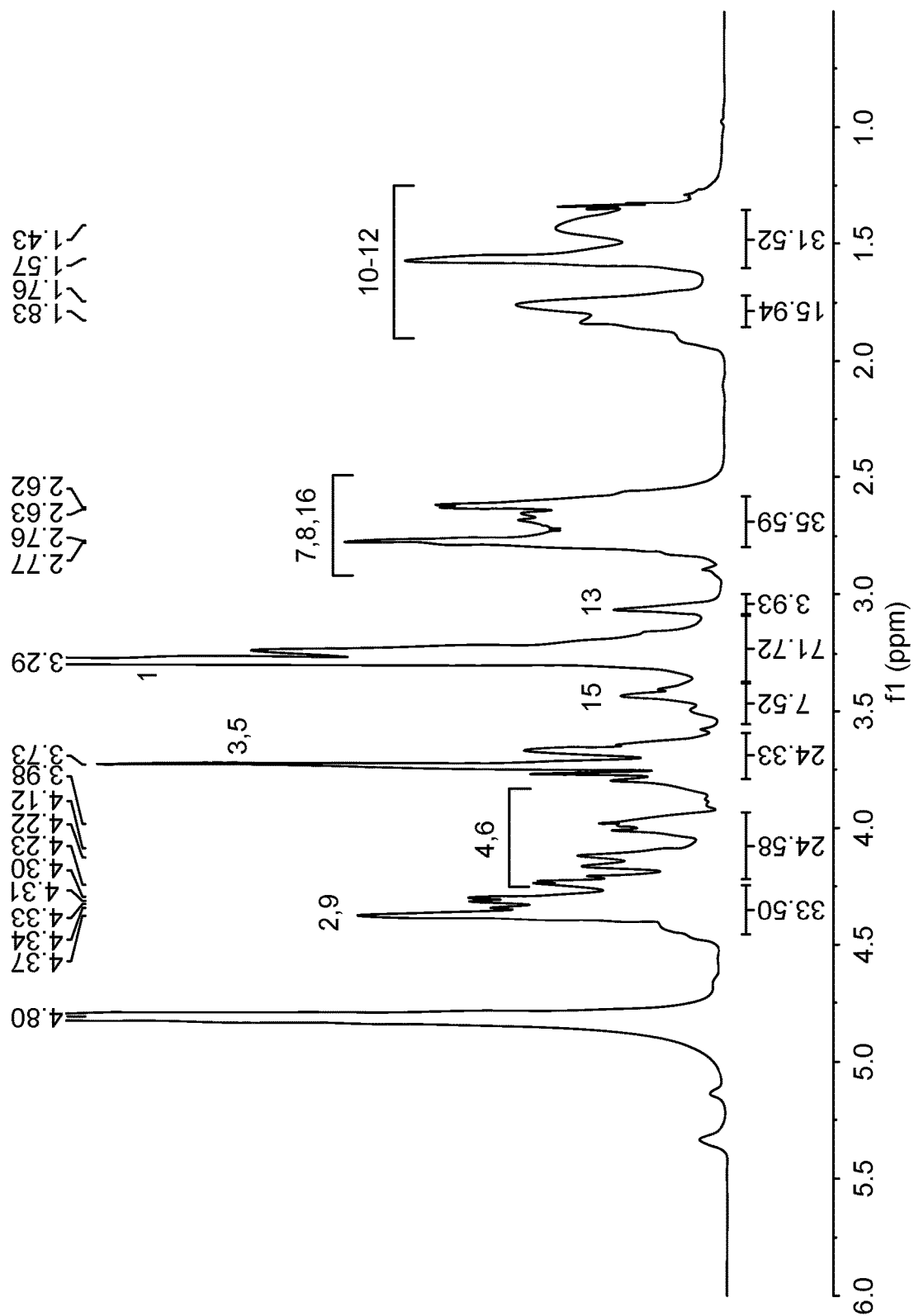
Figure 2A:
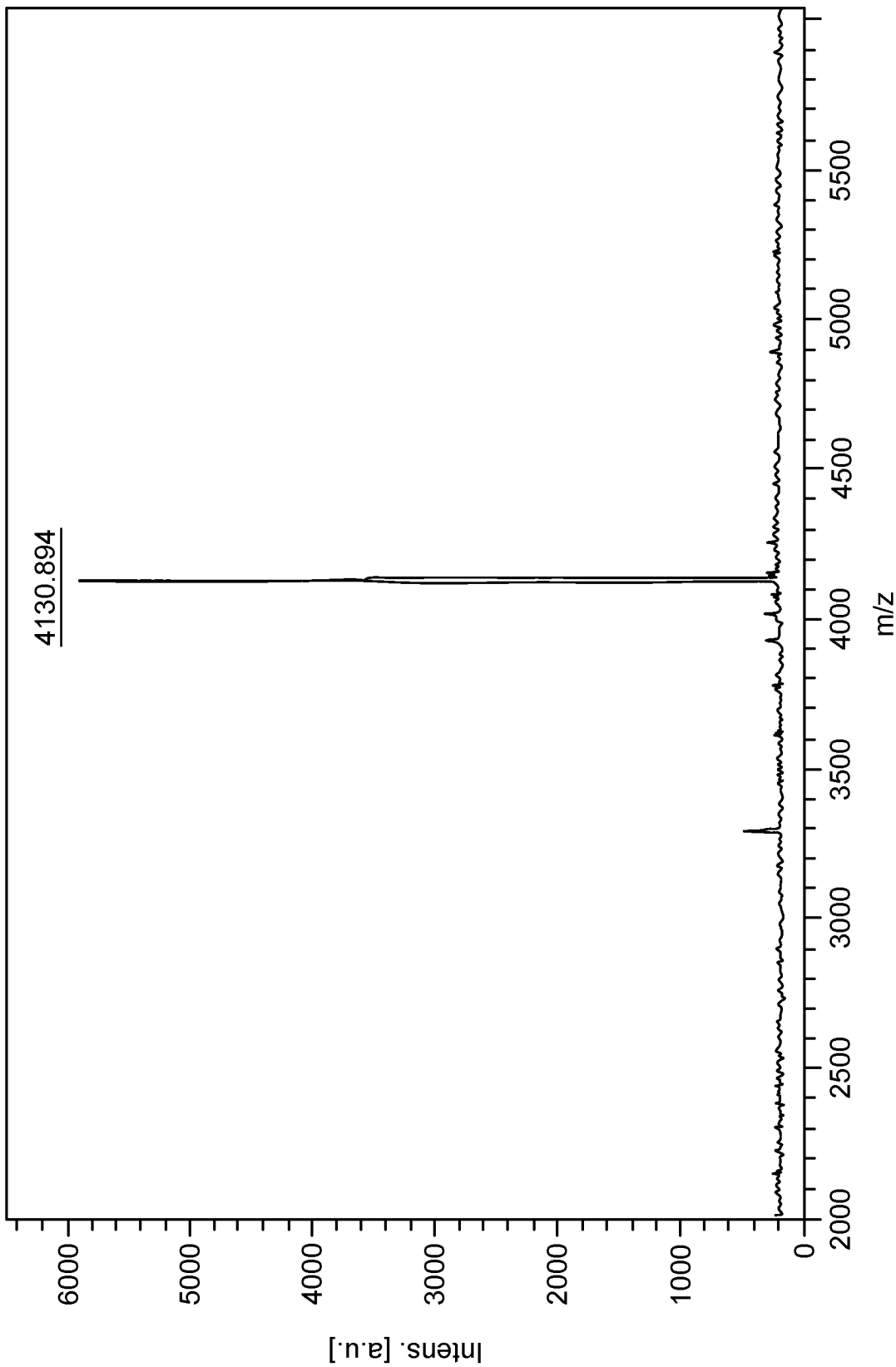
FIG. 2 shows characterization of dendron D-$DMBA_{16}$-$NH_2$. (A) MALDI-TOF MS and $^1$H NMR (B) spectra of dendron D-$DMBA_{16}$-$NH_2$. $^1$H NMR (600 MHz, DMSO) δ 8.23-7.78 (m, 33H), 4.25-4.08 (m, 16H), 3.50 (m, 4H), 3.38 (m, 4H), 3.18 (m, 4H), 3.12-2.85 (m, 66H), 2.76 (s, 96H), 2.36 (m, 4H), 2.24 (dd, J=11.9, 7.0 Hz, 16H), 2.16 (dd, J=11.9, 7.0 Hz, 16H), 1.83 (m, 32H), 1.73-1.12 (m, 102H).
Figure 2A:
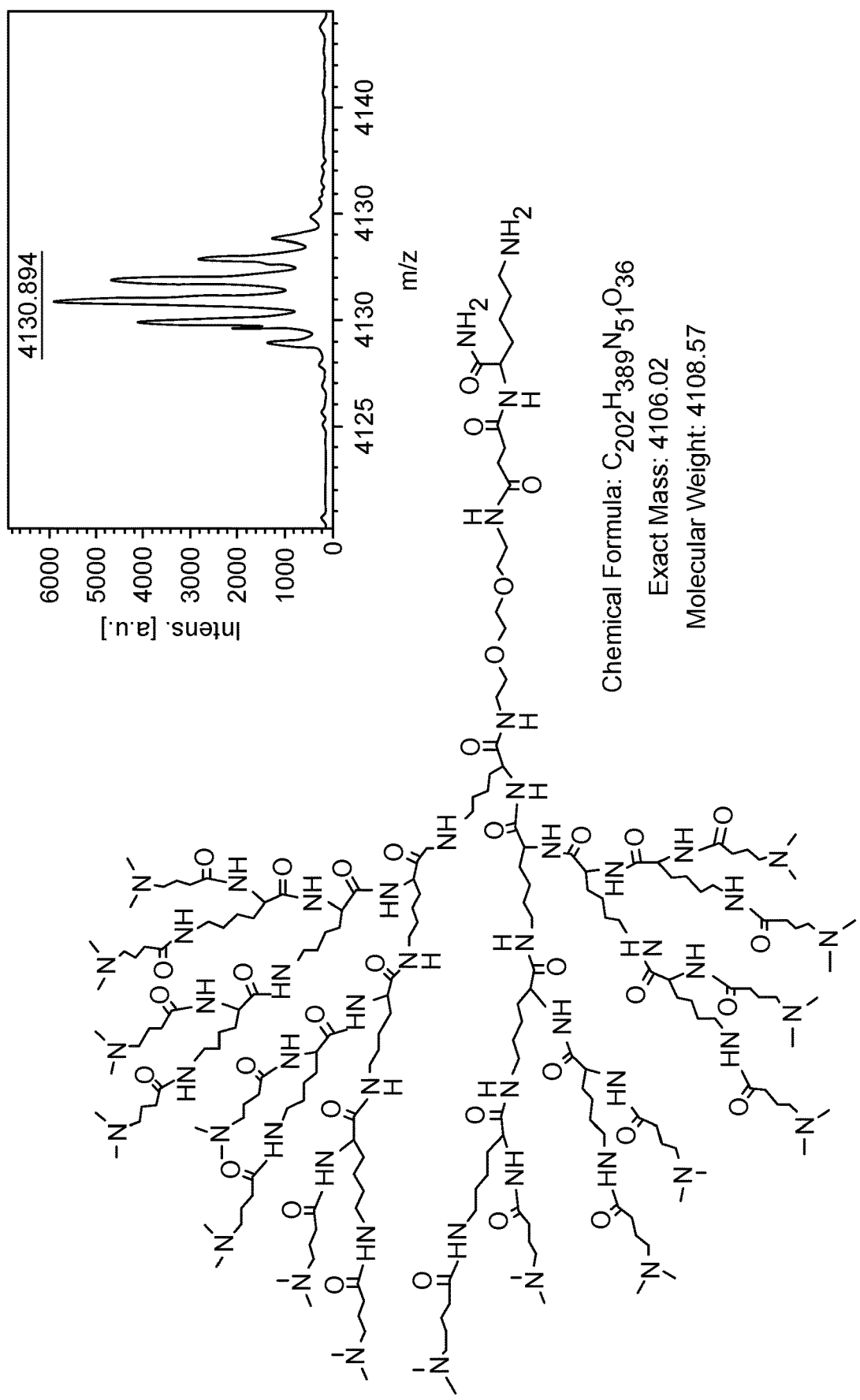
Figure 2B:
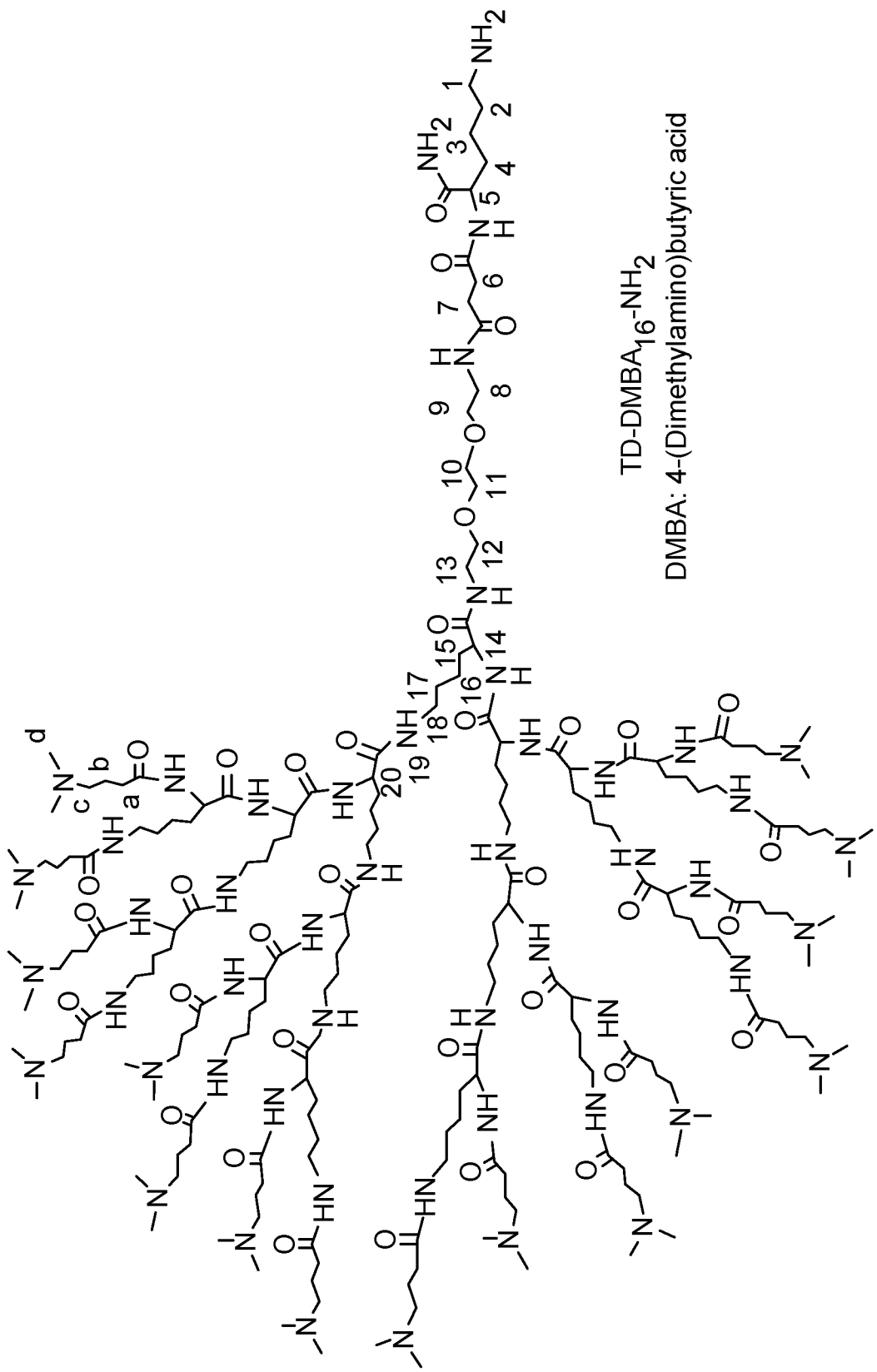
Figure 2B:
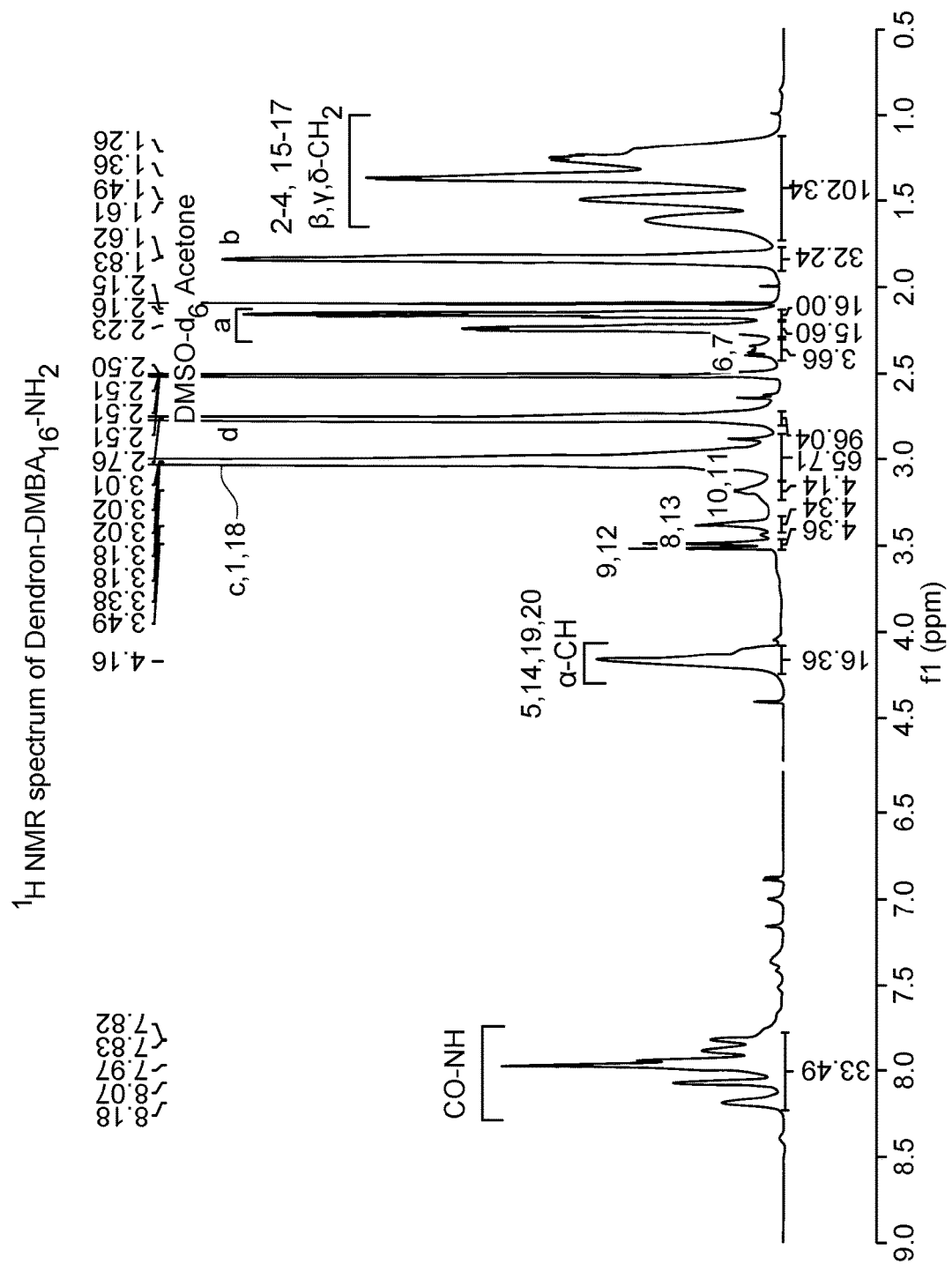

The present disclosure provides zwitterionic dendrimers and zwitterionic polymers and methods of making the zwitterionic dendrimers/polymers. Also provided are amphiphilic dendrimers and amphiphilic telodendrimers comprising one or more zwitterionic dendron/polymer/linear group(s)/moiety(s) and methods of using the amphiphilic dendrimers and/or amphiphilic telodendrimers (for example, in protein binding and drug delivery).

This disclosure describes, for example, production of zwitterionic amphiphiles which integrate the therapeutic binding and anti-fouling moieties into a single dendrimer. A novel combination of solid-phase peptide and liquid-phase peptide synthesis was developed for synthesizing the zwitterionic amphiphiles. The unique structure of zwitterionic amphiphiles enable them to self-assemble with therapeutics into nanocarriers with zwitterionic surface, displaying non-fouling property, and increase in vitro and in vivo stability of nanotherapeutics for targeted drug delivery.

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

Definitions

As used herein, the term "protein" includes peptides (generally 50 amino acids or less), polypeptides (generally, 100 amino acids or less), and proteins (greater than 100 amino acids). The protein can be a therapeutic protein (e.g., a cytotoxic protein or insulin). The protein can be an antibody, enzyme, or other bioactive protein.

As used herein, unless otherwise stated, the term "group" refers to a chemical entity that has one terminus that can be covalently bonded to other chemical species. For example,

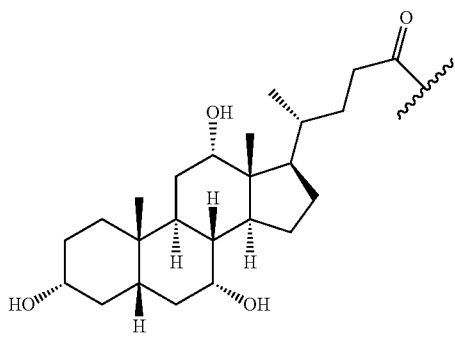

refers to a cholic acid group,

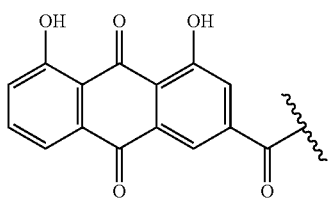 [SMILES: *C(=O)c1cc(O)c2c(c1)C(=O)c1cccc(O)c1C2=O]

refers to a rhein group,

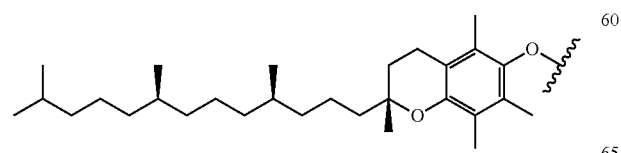

refers to a vitamin E group.

As used herein, unless otherwise stated, the term "moiety" refers to a chemical entity that has two or more termini that can be covalently bonded to other chemical species. Examples of moieties include, but are not limited to:

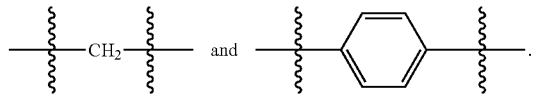

As used herein, the terms "dendritic polymer" and "dendritic polymer moiety" (e.g., $D^z$, $D^1$, and $D^2$) refer to branched polymers containing a focal point, a plurality of branched monomer units, and a plurality of end groups. The monomers are linked together to form arms (or "dendritic polymer moiety") extending from the focal point and terminating at the end groups. The focal point of the dendritic polymer can be attached to other segments of the compounds of the disclosure, and the end groups may be further functionalized with additional chemical moieties. The dendritic polymer can be composed of, for example, branched lysine and/or branched arginine moieties.

As used herein, the terms "nanocarrier" and "nanoparticle" refer to a micelle resulting from aggregation of dendrimer or telodendrimer conjugates of the present disclosure. The nanocarrier has a charged and/or hydrophobic core, which, optionally, comprises charged groups/moieties, and a hydrophilic exterior (e.g., a hydrophilic exterior with zwitterionic groups).

As used herein, the terms "monomer" and "monomer unit" refer to a diamino carboxylic acid, a dihydroxy carboxylic acid, or a hydroxyl amino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure. Monomers of the present disclosure can have a bond connectivity of, for example,

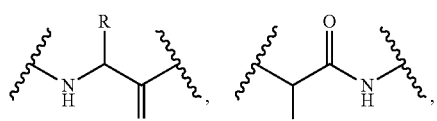

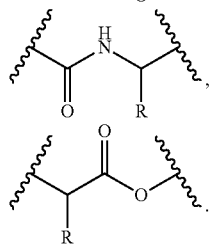

For example, when a monomer is defined as a lysine moiety, with a bond connectivity of A-Lys-B, where A and B are generic appendages, then it can be assumed that the structure can be any one of the following:

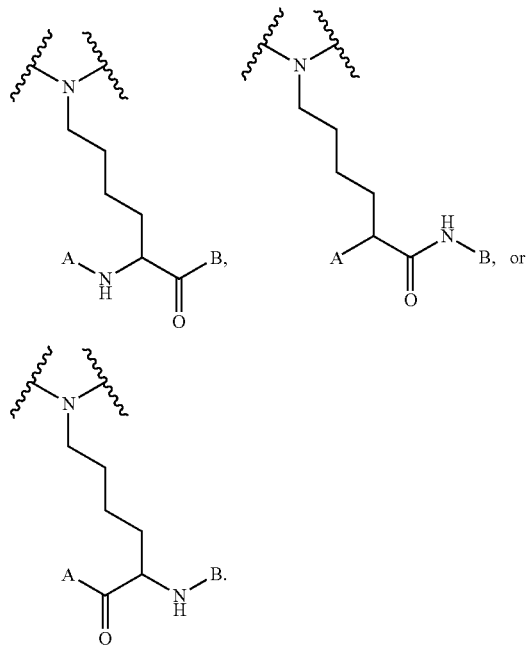

As used herein, the term "linker" refers to a chemical moiety that links (e.g., via covalent bonds) one segment (e.g., a reactive portion of a segment, such as, for example, an amine) of a dendritic conjugate to another segment (e.g., a reactive portion of another segment, such as, for example, a carboxylic acid) of the dendritic conjugate. In various examples, a linker is a chemical moiety that links (e.g., via covalent bonds) a dendron or fragment of a dendron or functional groups of a dendron. The types of bonds used to link the linker to the segments of the dendrimers include, but are not limited to, amides, amines, esters, carbamates, ureas, thioethers, thiocarbamates, thiocarbonate, and thioureas. For example, the linker (L, $L^R$, $L^Z$, $L^1$, $L^2$, $L^3$, and/or $L^4$), individually at each occurrence in the dendrimer, can be a polyethylene glycol moiety, polyserine moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker L, $L^R$, $L^Z$, $L^1$, $L^2$, L, and/or $L^4$ can be

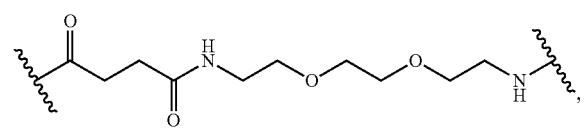

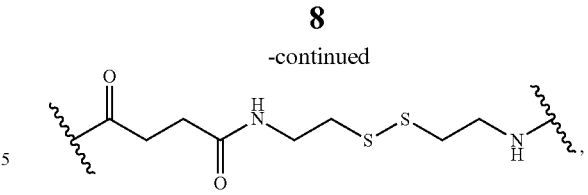

or a combination thereof, or other peptide sequence or spacer molecules (e.g., a glycine residue/moiety).

A linker may also refer to the functionality resulting from the reaction between at least two groups/moieties to result in a ZLG (e.g., an acylation reaction, "Click" reaction, and the like). Suitable reactions/methods will be known to those having skill in the art. Examples of linkers include, but are not limited to, esters (e.g., esters formed from a reaction of a carboxylic acid or the like with an alcohol), disulfides (e.g., disulfides formed from a reaction of two thiols), thioethers (e.g., thioethers formed from a reaction of a maleimide or the like and thiol or formed from a reaction of a thiol and halogenated aliphatic group (e.g., a brominated alkane)), thioesters (e.g., thioesters formed from a reaction of a carboxylic acid or the like and a thiol), amides (e.g., amides formed from a reaction between a carboxylic acid or the like and an amine), hydrazides (e.g., hydrazides formed from a reaction of a carboxylic acid or the like and a hydrazine), triazoles (e.g., a 1,2,3-triazole), which may be formed from a [3+2] cycloaddition between an alkyne and an azide, sulfur-carbon bonds (S—C bonds) and nitrogen-carbon bonds (N—C bonds) formed by a nucleophilic addition (e.g., such as through nucleophilic addition to an alpha-beta unsaturated ketone, such as in a Michael Reaction), and ring opening reactions (e.g., such as between a thiol with C═C bonds and epoxide)

As used herein, zwitterionic group (—ZD) or zwitterionic segment refers to a group formed from one or more zwitterionic dendrimer, linear zwitterionic group, zwitterionic polymer group, or combination thereof, that is covalently bound to an amphiphilic dendritic structure (e.g., covalently bound to a drug-binding dendron or a protein-binding dendron via a zwitterionic dendrimer linking group or linking group). For example, the structure of a zwitterionic group is

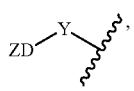

where Y is a zwitterionic linking group. In an example, a zwitterionic linking group is a "linker" as described herein.

As used herein, the term "reversible crosslinking group" refers to a chemical moiety that can be reversible reacted with another chemical moiety that will crosslink and decrosslink when exposed to certain conditions (e.g., different pH condition, chemical environments (e.g. sugar level), redox environments (concentration of glutathione) and UV light of varying wavelength). For example, a coumarin derivative moiety, can be photocrosslinked at >300 nm and decrosslinked (e.g., photolytically cleaved) at ~265 nm. Another example is catechol and boronic acid which form a boronate crosslinkage, which can be cleaved at acidic pH or with cis-diol containing sugar. Another example is disulfide formation, which can be cleaved under higher concentration of glutathione in vivo. The degree of crosslinking can be controlled by the density of crosslinking moieties and crosslinking conditions, e.g., the time of reversible photocrosslinkable groups are exposed to UV light.

As used herein, the term "reversible photocrosslinking group" refers to a chemical moiety that can be reversible reacted with another chemical moiety that will crosslink and decrosslink when exposed to certain conditions (e.g., UV light of varying wavelength). For example, a coumarin derivative moiety, can be photocrosslinked at >300 nm and decrosslinked at ~265 nm. The degree of crosslinking can be controlled by the amount of time the reversible photocrosslinkable groups are exposed to UV light.

As used herein, the term "oligomer" or "oligomer moiety" refers to fifteen or fewer monomers, as described above, covalently linked together. The monomers may be linked together in a linear or branched fashion. The oligomer may function as a focal point for a branched segment of a dendrimer.

As used herein, the term "hydrophobic group" refers to a chemical moiety that is water-insoluble or repelled by water. Examples of hydrophobic groups include, but are not limited to, alkanes (e.g., long-chain alkanes) and fatty acids, lipids, vitamins (e.g., vitamin E), natural compounds, herbal extracts, fluorocarbons, silicones, certain steroids such as cholesterol, bile acids, and certain polymers such as, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as, for example, PEG, PVA, and zwitterionic polymers.

As used herein, the term "amphiphilic compound" refers to a compound having both hydrophobic portions and hydrophilic portions. For example, the amphiphilic compounds of the present disclosure can have one hydrophilic part of the compound and one hydrophobic part of the compound, for example, bile acids, cholic acids, riboflavin, chlorgenic acid, etc.

As used herein, the term "polar compound" refers to a compound having a non-zero vector sum of its bond dipoles.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

In an aspect, the present disclosure provides zwitterionic linear compounds, zwitterionic polymers, and zwitterionic dendrimers. The zwitterionic linear compounds, zwitterionic polymers, and zwitterionic dendrimers can be discrete compounds or can be used to form one or more zwitterionic dendron groups on an amphiphilic dendrimer or amphiphilic telodendrimer. In various examples, the backbone of the zwitterionic linear compounds and/or zwitterionic dendrimers are formed from amide bonds, ester bonds, ether bonds, or a combination thereof.

In an example, the zwitterionic linear compounds are linear compounds comprising a linear polymer backbone comprising one or more pendant zwitterionic moieties/groups covalently bound to the polymer backbone (e.g., a linear polymer backbone comprising two or more branching monomers covalently bound to form a linear compound of branching moieties and one or more zwitterionic moieties groups covalently bound to a branching moiety or branching moieties). In an example, the branching monomer is lysine and the zwitterionic linear compound is linear polylysine with one or more zwitterionic moieties groups covalently bound to a lysine moiety or lysine moieties. In various other examples, the zwitterionic linear compounds are linear polymers comprising one or more pendant zwitterionic moieties/groups covalently bound to the polymer backbone.

Non-limiting examples of linear zwitterionic polymers and zwitterionic groups are shown in the following:

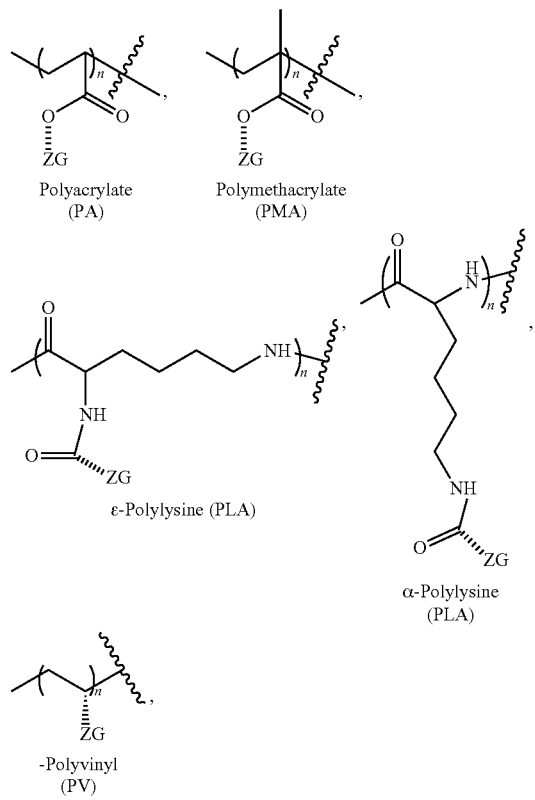

and the like, where n is, for example, 2-500, and the hashed line represents a bond, a linker (e.g., an ethylene glycol or a polyethylene glycol moiety with 2 or 3 ethylene glycol repeat units), or a spacer (e.g., a linker) and where ZG has the following structure:

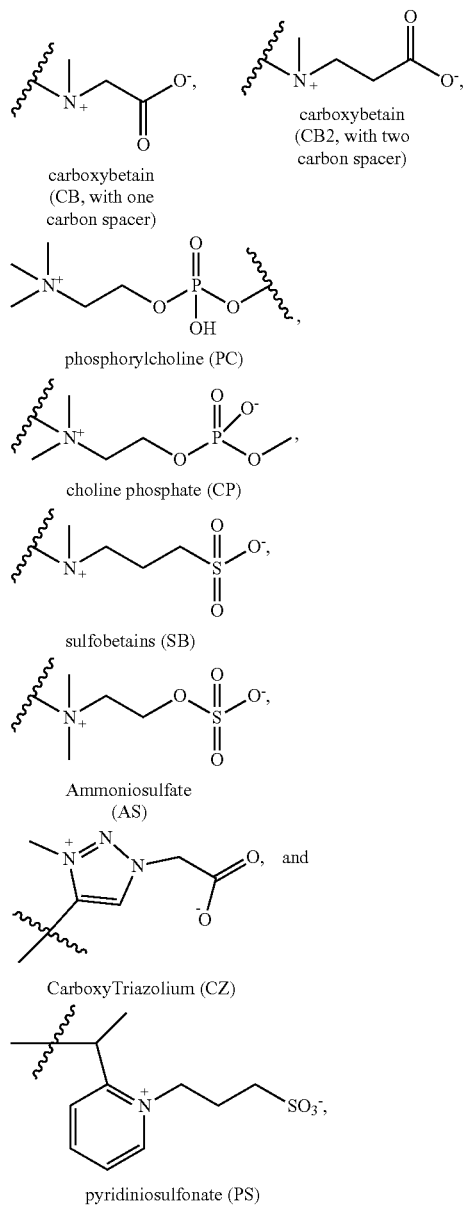

and the like.

In an example, the zwitterionic dendrimers are compounds of formula (A):

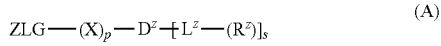

where ZLG is optionally present and is a zwitterionic dendron linking group; X is optionally present and is a branched monomer unit; each $L^z$ is independently optional and is a linker group; $D^z$ is a dendritic polymer moiety having one or more branched monomer units (X), and a plurality of end groups; $R^z$ is an zwitterionic end group of the dendritic polymer and is independently at each occurrence in the compound selected from the group consisting of carboxybetain (CB) groups/moieties, phosphorylcholine (PC) groups/moieties, choline phosphate (CP) groups/moieties, sulfobetaines (SB), targeting moieties and combinations thereof (with the proviso that at least one of the $R^z$ groups is a zwitterionic group); subscript s is an integer from 1 to 64; and subscript p is an integer from 1 to 32. In the case where the ZLG is not present, the dentritic polymer moiety or branched monomer unit (X) can be functionalized with various terminal groups. Examples of zwitterionic dendrons having formula (A) are shown, for example, in FIGS. 1, 2, 9 and 10.

Zwitterionic groups/moieties comprise a static positive charge and a negative charge and are overall neutral. The zwitterionic groups/moieties can be derived from zwitterionic compounds. For example; zwitterionic groups/moieties are $R^{(+)}$—$CH_2)_n$-$R^{(-)}$, where n is 1 to 3, $R^{(+)}$ is positively charged group/moiety such as, for example, quaternary amine groups/moieties, and $R^{(-)}$ is a negatively charged group/moiety such as, for example, carboxylate, sulfate, and, phosphate groups/moieties. In the case of a phosphate, the sequence of charge pair can be altered to be either PC or CP. Examples of zwitterionic groups/moieties include, but are not limited to carboxybetain (CB, with one carbon spacer) or CB2 (with two carbon spacer) groups/moieties, phosphorylcholine (PC) groups/moieties, choline phosphate (CP), sulfobetaines (SB), and combinations thereof. Examples of zwitterionic groups are shown above.

A zwitterionic linking group (ZLG) can be used to link a zwitterionic dendron to a dendrimer (e.g, via a $LG^Z$ group). The ZLG can have a terminal amino acid or terminal amino acid-$NH_2$ group (e.g., lysine group or terminal lys-$NH_2$ group). The ZLG can have a terminal group (e.g., an amine) that can be used to initiate dendrimer synthesis (e.g., a liquid phase dendrimer synthesis). Examples of zwitterionic linking groups include, but are not limited to, linkers as described herein. In an example, the zwitterionic linking group (ZLG) has the following structure:

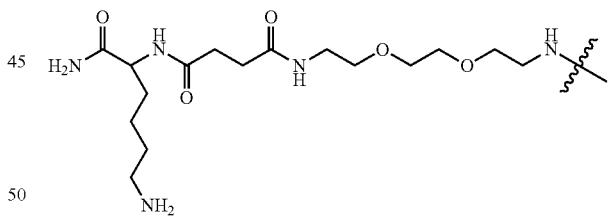

an analog thereof.

The zwitterionic linear compounds and zwitterionic dendrimers may comprise one or more targeting ligands covalently bound to the zwitterionic linear compound backbone (e.g., to the distal end of zwitterionic linear compound) or zwitterionic dendrimer (e.g., the periphery of a zwitterionic dendrimer) (e.g., $R^z$). Examples of targeting ligands include, but are not limited to, small molecules, peptides, proteins, and combinations thereof. Examples of suitable targeting ligands and conjugation methodologies are known in the art.

In an aspect, the present disclosure provides amphiphilic dendrimers and amphiphilic telodendrimers comprising one or more zwitterionic groups (e.g., zwitterionic linear compounds, zwitterionic polymers (e.g., zwitterionic linear polymers), or a combination thereof) and one or more other dendrons (e.g., drug-binding and/or protein-binding dendrons. The amphiphilic dendrimers can be hybrid dendrimers with two distinct dendrons. The dendrimers are also referred to herein as Janis-type amphiphiles. The amphiphilic dendrimers and/or amphiphilic telodendrimers can form nanocarriers (e.g., single or multi-layer dendrimer micelle structures). The nanocarriers can comprise a hydrophilic layer, which can be an external layer, that comprises one or more zwitterionic groups. In an example, amphiphilic dendrimers and/or amphiphilic telodendrimer do not comprise any polyethylene glycol (PEG) groups and/or PEG moieties.

Without intending to be bound by any particular theory, it is considered that incorporation of zwitterionic dendrons into dendrimer structures provides dendrimers having anti-fouling characteristics. For example, incorporation of zwitterionic dendrons into dendrimer structures provides dendrimers that do not exhibit observable nonspecific protein binding. Nonspecific binding can be observed by methods know in the art.

Amphiphilic dendrimers of the present disclosure can comprise one or more dendrons other than zwitterionic dendrons. The other dendrons can be drug-binding dendrons and/or protein binding dendrons. Examples of drug-binding dendrons and protein-binding dendrons can be found in the telodendrimer structures described in U.S. patent application Ser. No. 13/972,539 (published as US 2015/0056139), PCT Application Nos. PCT/US14/52076 (published as WO 2015/027054), PCT/US16/51266, PCT/US2012/070508, U.S. patent application Ser. No. 14/117,570, U.S. Pat. No. 9,579,400, U.S. patent application Ser. No. 13/803,878, the description of telodendrimers and telodendrimer structures therein is incorporated herein by reference.

An amphiphilic dendron can comprise a zwitterionic dendron covalently bound (e.g., via a linking group or zwitterionic linking group) to a drug-binding dendron and/or protein-binding dendron. For example, zwitterionic dendron(s) can be covalently linked to an amphiphilic dendrimer via a branched monomer unit (e.g., lysine moiety/group) of the dendrimer (or other dendron such as, for example, drug-binding dendron, protein-binding dendron, hydrophobic dendron, charged dendron) and/or a terminal amine of a zwitterionic dendron.

The drug binding dendron and/or protein-binding dendron, which can be derived from telodendrimer structures described herein, can comprise or more segments. The dendrons can comprise multiple segments (e.g., linear hydrophilic polymer segments, adjacent branched functional segments, interior dendritic drug-binding segments). As used herein the term "layer" when used in reference to dendrons refers to the corresponding segment in the dendron that corresponds to that layer in the nanocarrier.

In various examples, the drug binding dendron and/or protein-binding dendrons can be functional segregated dendrons having, for example, two or three functional segments. In an embodiment, the functional segments are a hydrophilic segment, an intermediate segment, and a hydrophobic segment. The intermediate segment can contain functional reactive moieties and reactive groups. The dendron may have one or more crosslinking groups (e.g., reversible photocrosslinking groups). In an embodiment, a plurality of crosslinking groups (e.g., reversible photocrosslinking groups) are crosslinked.

The intermediate layer, if present, contains for example, optional crosslinkable functional group(s), amphiphilic oligo-cholic acid, riboflavin, or chlorogenic acid and can further stabilize nanoparticle and cage drug molecules in the core of nanoparticle; the interior layer contains drug-binding building blocks, such as vitamins ($\alpha$-tocopherol, riboflavin, folic acid, retinoic acid, etc.) functional lipids (ceramide), chemical extracts (rhein, coumarin, curcumin, etc.) from herbal medicine to increase the affinity to drug molecules.

In an example, the dendrons are functional and spatially segregated dendrons having, for example, two or three functional segments. The dendrons can have one or more crosslinking groups (e.g., reversible photocrosslinking groups) and one or more functional reactive moieties (FRM).

In an example, the amphiphilic dendrimers or amphiphilic telodendrimers are compounds of formula (I):

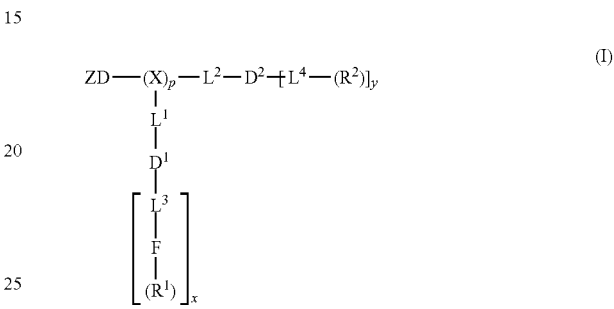

where ZD is a zwitterionic group comprising one or more zwitterionic dendron, zwitterionic linear group (which can be formed from a zwitterionic polymer, which is linear or branched), or a combination thereof (the group may be linked to the dendrimer via a linking group such as, for example, a lysine moiety); X is optionally present and is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), and a plurality of end groups; $D^2$ is a dendritic polymer moiety having one or more branched monomer units (X), and a plurality of end groups; F is independently optional a functional reactive moiety selected for specific drug conjugation/complexation via labile bonds, reversible complexes or charge interactions; $R^1$ is an end group of the dendritic polymer and is independently at each occurrence in the compound selected from the group consisting of the end groups of the dendritic polymer, hydrophobic group, a hydrophilic group, an amphiphilic group, a reversible photocrosslinking group, a drug, catechols, crosslinkable groups (boronic acid, cisdiols, amine, carboxylic acids, acryl groups, epoxide, thiol groups, malaimide, C=C double bond, azide, alkyne, coumarin and chlorogenic acid, etc.), boronic acids, carboxylic acids, acylhydrazines, hydroxyl, amines, thiols and ketones for labile bond formation, a positively charged moiety (e.g., primary, secondary or tertiary amines for gene delivery), amphiphilic groups (e.g. cholic acid, riboflavin, chlorogenic acid), chelating groups (e.g., amines, aromatic imines, and carboxylic acids), and thiol groups for metallic drug chelation); each $R^2$ is an end group of the dendritic polymer and is independently at each occurrence in the compound selected from the group consisting of positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups, such as sugars, peptides, and hydrophilic polymers), or hydrophobic groups, such as, for example, alkanes ($C_1$-$C_{50}$) (e.g., long-chain alkanes) and fatty acids ($C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine)), or amphiphilic groups (e.g. cholic acid, riboflavin, chlorogenic acid), a reversible photocrosslinking group, and a drug; subscript x is an integer from 1 to 64, subscript y is an integer from 1 to 64, and subscript p is an integer from 0 to 32 or 1 to 32. Examples of functional amphiphilic dendrimers and/or amphiphilic telodendrimers having formula (I) are shown, for example, in FIG. 2.

In an example, the amphiphilic dendrimers or amphiphilic telodendrimers have the following structure: $ZD(X)_p$-L-D—[ $L^R$-F—vR)]$_y$, wherein ZD is a zwitterionic group comprising one or more zwitterionic dendron, zwitterionic linear group (which can be formed from a zwitterionic linear dendron or zwitterionic polymer, where the polymer is linear or branched), or a combination thereof (the group may be linked to the dendrimer via a linking group such as, for example, a lysine moiety);

X is optionally present and is a branched monomer unit;

each L is independently optional and is a linker group;

each $L^R$ is independently optional and is a linker group;

D is a dendritic polymer moiety having one or more branched monomer units (X), and a plurality of end groups;

F is independently optional and a functional reactive moiety selected for specific drug conjugation/complexation via labile bonds, reversible complexes or charge interactions;

R is an end group of the D dendritic polymer moiety and is independently at each occurrence in the compound selected from the group consisting of the end groups of the dendritic polymer, hydrophobic group, a hydrophilic group, an amphiphilic group, a reversible photocrosslinking group, a drug, catechols, crosslinkable groups (e.g., boronic acid, cisdiols, amine, carboxylic acids, acryl groups, epoxide, thiol groups, maleimide, C=C double bond, azide, alkyne, coumarin and chlorogenic acid, etc.), boronic acids, carboxylic acids, acylhydrazines, hydroxyl, amines, thiols and ketones for labile bond formation, a positively charged moiety (e.g., primary, secondary or tertiary amines for gene delivery), amphiphilic groups (e.g. cholic acid, riboflavin, chlorogenic acid), chelating groups (e.g., amines, aromatic imines, and carboxylic acids), and thiol groups for metallic drug chelation); each $R^2$ is an end group of the $D^2$ dendritic polymer moiety and is independently at each occurrence in the compound selected from the group consisting of positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups, such as sugars, peptides, and hydrophilic polymers), or hydrophobic groups, such as alkanes (e.g., long-chain alkanes) (e.g., $C_1$-$C_{50}$) and fatty acids (e.g., $C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine)), or amphiphilic groups (e.g. cholic acid, riboflavin, chlorogenic acid), a reversible photocrosslinking group, and a drug;

subscript y is an integer from 2 to 64, and subscript p is an integer from 0 to 32.

In an embodiment, the reversible crosslinking group (e.g., $R^1$), if present, is a coumarin moiety, 4-methylcoumarin moiety, boronic acid moiety or derivative or analog thereof, catechol moiety or derivative or analog thereof, cis-diol moiety or derivative or analog thereof, cinnamic acid moiety or derivative or analog thereof, chlorogenic acid moiety or derivative or analog thereof, amine moiety or a derivative thereof, carboxylic acid or a derivative thereof, acyl group, or a derivative thereof, epoxide or a derivative thereof, thiol group or a derivative thereof, maleimide or a derivative thereof, alkene or a derivative thereof, azide or a derivative thereof, alkyne or a derivative thereof, coumarin or a derivative thereof, or a combination thereof.

In an embodiment, $R^2$ comprises two different end groups, where one half of the $R^2$ end groups are one of said group and one half of the $R^2$ end groups are a second of said group (e.g., $R^2$ or $R^3$ groups).

In an embodiment, the $R^2$ groups comprise at least one positively or negatively charged groups. The charged groups are positively charged groups or negatively charged groups. In an embodiment, all of the charged groups present are positively charged groups. In an embodiment, all of the charged groups are negatively charged groups. In an embodiment, the number of charged groups present in the dendrimer is 1-128, including all integer numbers of charged groups and ranges therebetween. In an embodiment, the number of charged groups present in the dendrimer is 2-64. In an embodiment, the number of charged groups present in the dendrimer is 4-16. In an embodiment, the number of charged groups present in the dendrimer is 4. In an embodiment, the number of charged groups present in the dendrimer is 8. In an embodiment, the guanidine portion of the arginine subunits are not part of $D_2$, but rather, the guanidine moiety is an $R^2$ group.

The charged group can be any group/moiety with a positive or negative charge. For example, the charged group has a positive or negative charge in aqueous solution at a certain pH (e.g., a pH of 6.8-7.6). In an embodiment, the charged group (e.g., $R^2$) is a moiety or derivative or analog of arginine, lysine, or guanidine. In an embodiment, the charged group (e.g., $R^2$) is a moiety or derivative or analog of an amine, amidine, tetrazole, hydroxyl, carboxyl, phosphate, sulfonate, sulfonamide (e.g., methanesulfonamide), oxalic acid, or similar functional groups.

In an example, a compound has sufficient hydrophobic groups to induce aggregation of a plurality of the compounds such that a nanoparticle (e.g., a micelle, nanoaggregate) is formed. The nanoparticle can be a nanocarrier.

In an embodiment, the neutral group is the moiety or derivative or analog of sugars, peptides, hydrophilic polymers, alkanes (e.g., long-chain alkanes) (e.g., $C_1$-$C_{50}$) and fatty acids (e.g., $C_1$-$C_{50}$), aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); amphiphilic groups, cholic acid, riboflavin, chlorogenic acid and natural compound extract and synthetic compounds.

When X is present, in an embodiment, at each occurrence in the compound, the branched monomer unit (X) in the compound of formula (I) is independently selected from the group consisting of a diamino carboxylic acid moiety, a dihydroxy carboxylic acid moiety, and a hydroxyl amino carboxylic acid moiety.

End groups (e.g., R, $R^z$, $R^1$, and $R^2$) are covalently bound to a dendritic polymer or linker. For example, a compound/molecule used to form an R group has one or more functional groups (e.g., carboxylic acid(s)/carboxylate(s)) that can react with a terminal functional group (e.g., amine) of a linker precursor or a terminal functional group of a dendritic group/moiety.

$R^2$ is covalently bonded to a dendritic polymer or linker. The $R^2$ groups may be end groups of a dendritic polymer. The $R^2$ groups may be linked to another $R^2$ group or $R^2$ end groups. $R^2$ groups may be directly bonded to the dendritic moiety (e.g. the guanidine portion of an argine moiety), or they may be attached through a linker. When $R^2$ is not an end group, each $R^2$ is linked to one of the end $R^2$ groups.

In an embodiment, the $R^2$ groups are independently at each occurrence in the compound selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof. In an embodiment, subscript y is an integer from 2 to 64, including all integer values and ranges therebetween. In an embodiment, subscript y is equal to the number of end groups on the dendritic polymer. In an embodiment, at least half the number y of $R^2$ groups are each independently selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof.

In an embodiment, the $R^2$ group(s) is/are independently at each occurrence in the compound selected from the group consisting of positively or negatively charged groups (e.g., arginine, lysine, guanidine, amine (e.g., secondary, tertiary or quaternary amines), amidine, tetrazole, hydroxyl, carboxyl, phosphate, sulfonate, methanesulfonamide, sulfonamide, or oxalic acid functional groups) and neutral groups (e.g., polar groups: sugars, peptides, hydrophilic polymers, or hydrophobic groups: alkanes (e.g., long-chain alkanes) (e.g., $C_1$-$C_{50}$) and fatty acids (e.g., $C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); or amphiphilic groups, cholic acid, riboflavin, chlorogenic acid). In an embodiment, at least one positively or negatively charged groups are present as $R^2$ groups. In an embodiment where at least one positively or negatively charged groups are present as $R^2$ groups, at least one $R^2$ group is a hydrophobic group/moiety. In an embodiment, all of the $R^2$ groups present in the charged dendrimer are charged groups or hydrophobic groups and the $R^1$ groups, if present, are hydrophobic and/or crosslinking groups.

$R^1$, if present, is covalently bonded to a functional reactive moiety, a dendritic polymer or a linker. The $R^1$ groups may be end groups. The $R^1$ groups may be linked to another $R^1$ group or $R^1$ end groups. $R^1$ and can include, for example: crosslinkable groups (boronic acid, cisdiols, amine, carboxylic acids, acryl groups, epoxide, thiol groups, malaimide, C=C double bond, azide, alkyne, coumarin, and chlorogenic acid, etc.). When $R^1$ is not an end group, each $R^1$ is linked to one of the end $R^1$ groups. $R^1$ can be end groups of the dendritic polymer and can include, for example: a hydrophobic group, a hydrophilic group, an amphiphilic group, a reversible photocrosslinking group, a drug, catechols, crosslinkable groups (boronic acid, cisdiols, amine, carboxylic acids, acryl groups, epoxide, thiol groups, malaimide, C=C double bond, azide, alkyne, coumarin and chlorogenic acid etc), catechol, boronic acids, carboxylic acids, acylhydrazines, hydroxyl, amine, thiol and ketone for labile bond formation; or positively charged moieties, e.g., primary, secondary or tertiary amines for gene delivery; or chelating groups, e.g., amines, aromatic imines and carboxylic acid, and thiol group, for, e.g., metallic drug chelation. Any appropriate therapeutic compound, e.g., drugs and prodrugs, can be conjugated to the intermediate layer, including DNA, RNA, SiRNA, peptide, cisplatin, oxaliplatin, Botezomib, doxorubicin, hydrophilic targeted inhibitors, etc.

In various embodiments, the amphiphilic dendrimer compound of the present disclosure has the following structure:

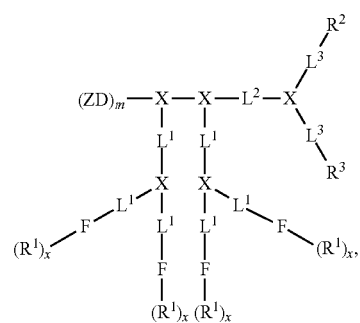

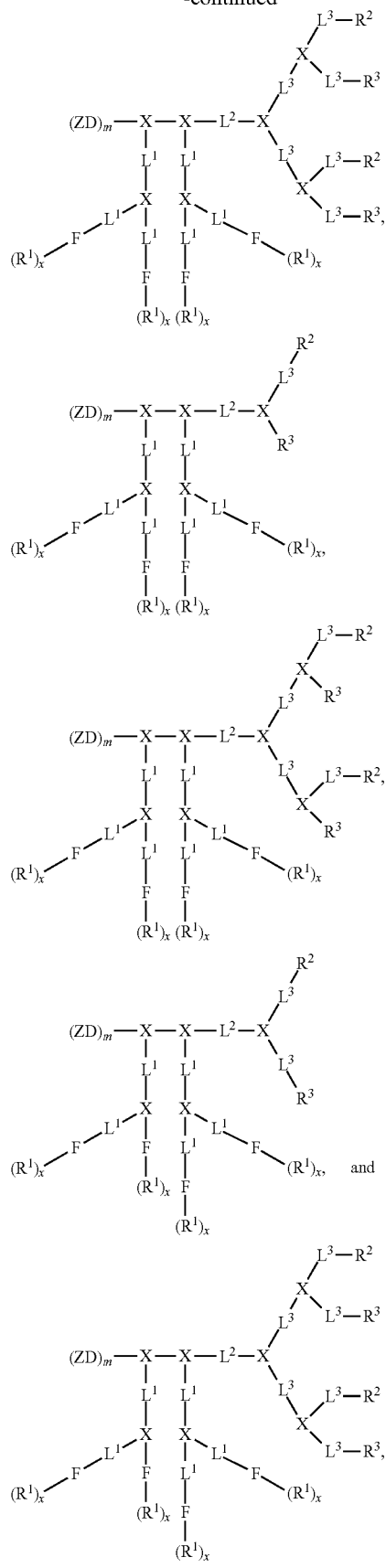

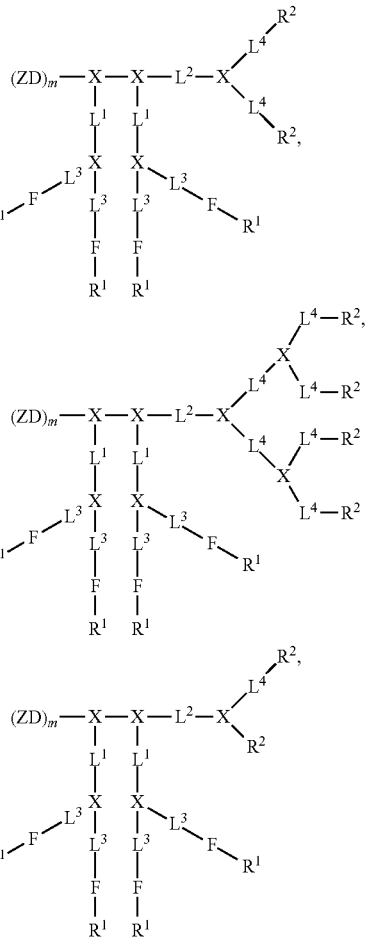

where each branched monomer unit may be a lysine moiety. In these structures, the arm of the amphiphilic dendrimer comprising the $(ZD)_m$ group/moiety is the hydrophilic segment, the branch(es) of the dendrimer comprising the $L^1$ moiety/moieties is/are the intermediate segment(s), and the branch(es) of the dendrimer comprising the $L^2$ moiety/moieties is/are the hydrophobic segment. $R^2$ is as defined herein and $R^3$ is an end group of the dendritic polymer and is selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof.

In various embodiments, the amphiphilic dendrimers or amphiphilic telodendrimers have the following structure:

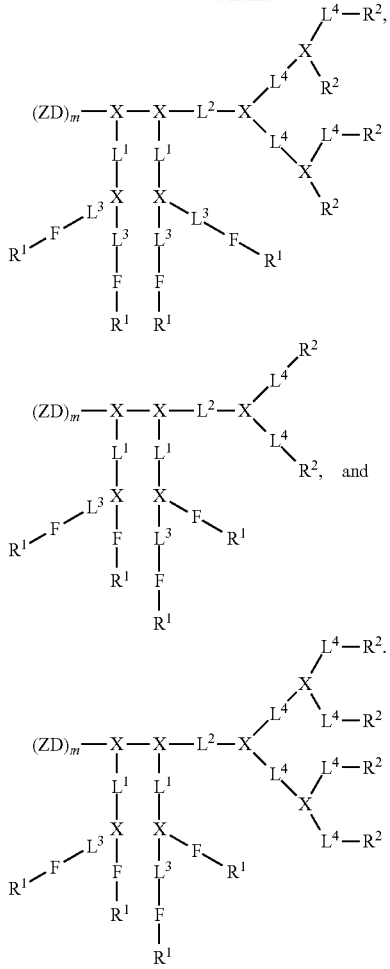

For example, each branched monomer unit is a lysine moiety.

In an embodiment, at each occurrence in the compound the linker $L^1$, $L^2$, $L^3$, and $L^4$ in the compound of formula (I) are independently at each occurrence selected from the group consisting of a polyethylene glycol moiety, polyserine moiety, enzyme cleavable peptide moiety, disulfide bond moiety, acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an embodiment, at each occurrence in the compound the linker $L^1$, $L^2$, $L^3$, and $L^4$ are independently at each occurrence selected from the group consisting of:

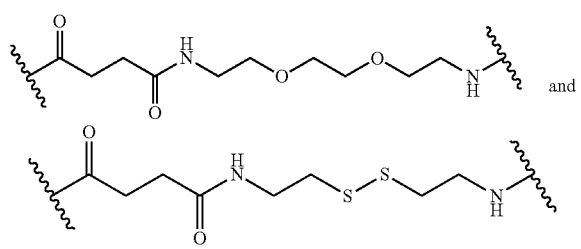

and in the compound of formula (I). In an embodiment, the linker $L^1$, $L^2$, $L^3$, $L^4$, or a combination thereof comprises a cleavable group in the compound of formula (I). In an embodiment, the cleavable group is a disulfide cleavable moiety in the compound of formula (I).

In an embodiment, the ZD portion of the amphiphilic dendrimer compound is selected from the group consisting of:

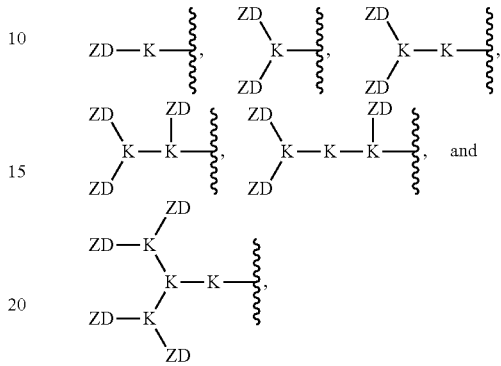

for example, where each K is lysine in the compound of formula (I).

In an embodiment, each $R^2$ and $R^3$ (there can be more than two different $R^2$ end groups), if present, is independently selected from an arginine, a lysine, a guanidine, an amine, an amidine, a tetrazole, a hydroxyl, a carboxyl, a phosphate, a sulfonate, a methanesulfonamide, a sulfonamide, an oxalic acid a polar group, such as a sugar, a peptide, a hydrophilic polymer, a rhein moiety or derivative or analog thereof, cholic acid moiety or derivative or analog thereof, moiety or derivative or analog thereof, coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, vitamin E moiety or derivative or analog thereof, D-α-tocopherol succinate moiety or derivative or analog thereof, vitamins, lipids, fatty acids, bile acids, naturally-isolated compound moieties, and drugs, and combinations thereof in the compound of formula (I). In another embodiment, each $R^2$ and $R^3$, if present, is a reversible photocrosslinking group. For example, the reversible photocrosslinking group is coumarin moiety, 4-methylcoumarin moiety, cinnamic acid moiety, chlorogenic acid moiety or derivative or analog thereof, or a combination thereof. $R^2$ and $R^3$ can be the same.

In an embodiment, each F is a functional reactive moiety of a dendrimer of the present disclosure with one or more (x) $R^1$ functional groups selected for specific drug conjugation/complexation via labile bonds, reversible complexes or charge interactions. In an embodiment, F may be a moiety of $R^1$. The reactive groups $R^1$ can include: catechol, boronic acids, carboxylic acids, acylhydrazines, hydroxyl, amine, thiol and ketone for labile bond formation; or positively charged moieties, e.g., primary, secondary or tertiary amines for gene delivery; or chelating groups, e.g., amines, aromatic imines and carboxylic acid, and thiol group for metallic drug chelation. $R^1$ can comprise more than one of such functional groups. Any appropriate therapeutic compound, drug and prodrug can be conjugated to the intermediate layer. Therapeutic agents such as, for example, hydrophilic therapeutic agents, hydrophobic therapeutic agents, amphiphilic therapeutic agents, polar therapeutic agents, non-polar therapeutic agents or combinations thereof can be conjugated to the intermediate layer. Examples of suitable therapeutic agents include DNA, RNA, SiRNA, peptide, cisplatin, oxaliplatin, Botezomib, doxorubicin, hydrophilic targeted inhibitors, etc. Examples of suitable therapeutic agents are disclosed herein.

In an embodiment, the amphiphilic dendrimer comprises one or more therapeutic agents (e.g., drugs). In an embodiment, the dendrimer comprises hydrophilic drug and hydrophobic drug molecules in the non-zwitterionic dendron(s) (e.g., drug-binding dendron(s)). In an embodiment, the dendrimer has one drug (e.g., cisplatin) and the drug is in the segment that forms the intermediate layer of the dendrimer micelle. The therapeutic agents (e.g., drugs) and/or non-therapeutic agent chemical compounds (e.g., imaging agents) are complexed and/or conjugated to the dendrimer.

The drug conjugation/complexation described herein has the advantage of allowing the delivery by a single micelle nanoparticle of hydrophobic therapeutic compounds with non-hydrophobic therapeutic compounds, including hydrophilic and amphiphilic drug compounds, heavy metal-containing therapeutic compounds, and polynucleotide reagents. It also allows for nanoparticles to be designed to achieve differential dosing and release timing of the hydrophobic compound and the non-hydrophobic compound to achieve synergistic effects on tumors. Conjugation of the therapeutic compound to the amphiphilic dendrimers or amphiphilic telodendrimers comprising the nanoparticle reduces dissipation of the therapeutic compound from the nanoparticle into the blood stream, thereby reducing toxicities associated to the compound. Three-layer amphiphilic dendrimer micelle nanoparticles were shown to be highly stable and preferentially targeting tumor sites, a high proportion of the drug conjugated/complexed to the intermediate layer is delivered to the tumor. One or more of the individual therapeutic agents in each combination therapy can be conjugated or complexed to the dendrimers of the present disclosure.

Examples of combination therapies (combinations of drugs) include: bleomycin and etoposide; carboplatin and methotrexate; carboplatin and etoposide; cisplatin and fluorouracil; cisplatin and topotecan; cisplatin and dexamethasone; cisplatin and cytarabine; dexamethasone and cytarabine; cisplatin, dexamethasone and cytarabine; docetaxel and carboplatin; epirubicin and cisplatin; epirubicin and fluorouracil; cisplatin and fluorouracil; epirubicin, cisplatin and fluorouracil; epirubicin and capecitabine; cisplatin and capecitabine; epirubicin, cisplatin and capecitabine; epirubicin and oxaliplatin; epirubicin and capecitabine; oxaliplatin and capecitabine; epirubicin, oxaliplatin and capecitabine; etoposide and cisplatin; methotrexate and mitoxantrone; oxaliplatin and capecitabine; paclitaxel and carboplatin; pemetrexed and cisplatin; vinorelbine and carboplatin; vinorelbine and cisplatin. Other combination therapies using two or more individual drugs or using individual or multiple drugs and drugs or other therapeutically useful are possible.

In an example, the amphiphilic dendrimers or amphiphilic telodendrimers comprise one or more charged dendrons, which can be derived from charged-telodendrimer structures described herein, and one or more zwitterionic dendrons. The charged amphiphilic dendrimers or amphiphilic telodendrimers comprise charged dendrons that are linear-dendritic copolymers. The charged dendrons are functional segregated dendrons having multiple segments, for example, two or three functional segments. In an embodiment, the functional segments are a hydrophilic segment and a hydrophobic segment. The hydrophilic segment comprises one or more charged groups. The charged dendrimers may comprise an intermediate layer. The charged dendrimers may have one or more crosslinking groups (e.g., boronic acid/catechol reversible crosslinking groups).

The charged amphiphilic dendrimers or amphiphilic telodendrimers comprise one or more zwitterionic groups. The intermediate layer, if present, contains for example, optional crosslinkable functional group(s), amphiphilic oligo-cholic acid, riboflavin, or chlorogenic acid and can further stabilize nanoparticle and cage drug molecules in the core of nanoparticle. The interior layer (i.e., hydrophilic layer) comprises positively or negatively charged moieties and may comprise, for example, protein-binding building blocks, such as vitamins (e.g., α-tocopherol, riboflavin, folic acid, retinoic acid, etc.), functional lipids (ceramide), and chemical extracts (e.g., rhein, coumarin, curcurmine, etc.), from herbal medicine to increase the affinity to drug molecules.

In an embodiment, the present disclosure provides charged dendrimers that are functional and spatially segregated dendrimers having 1 to 128 charged groups. The dendrimers may have one or more crosslinking groups (e.g., reversible boronate crosslinking groups). In an embodiment, the dendrimers are functional segregated dendrimers having three functional segments.

In various embodiments, the amphiphilic dendrimer of the present disclosure has the following structure:

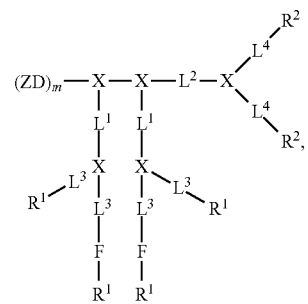

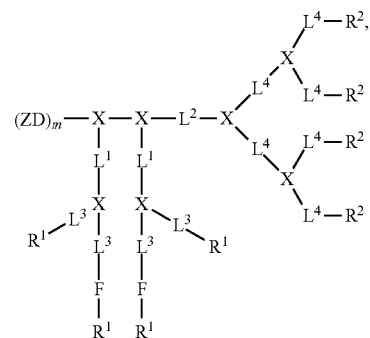

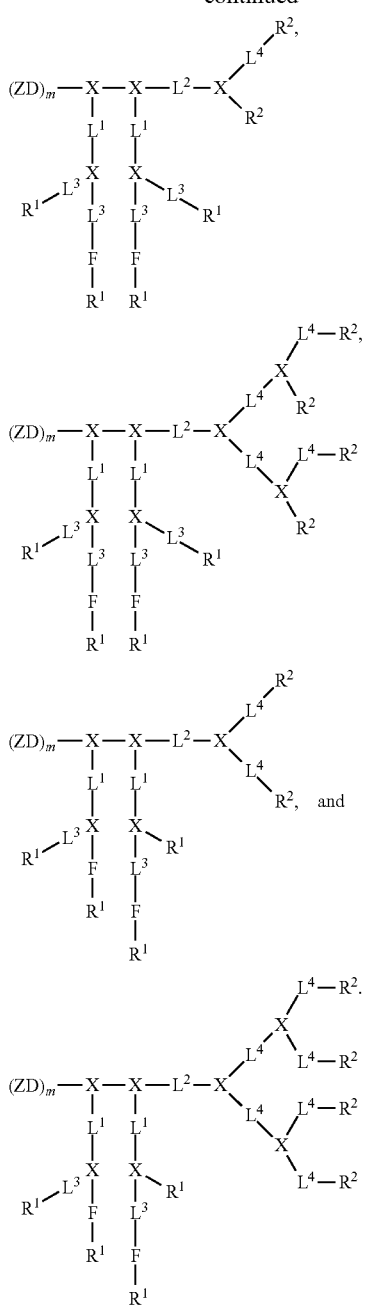

In various embodiments, the amphiphilic dendrimer of the present disclosure has the following structure:

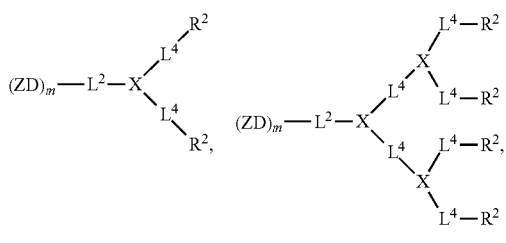

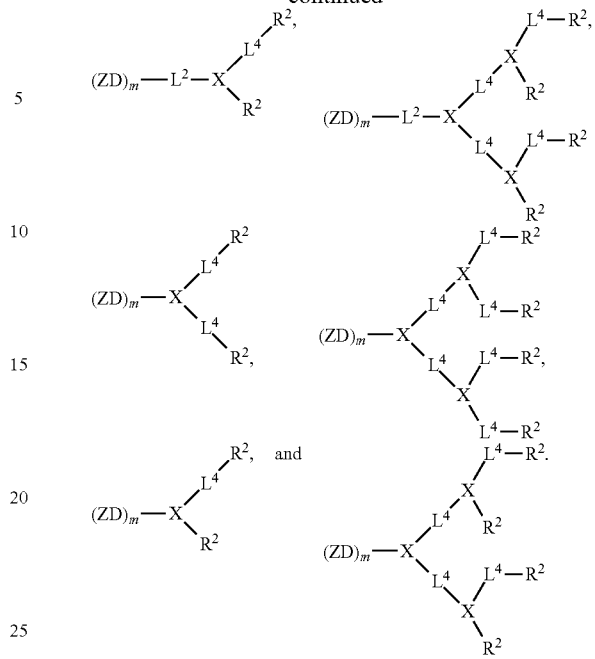

The dendritic moiety may comprise one or more amino acid moieties (e.g., lysine and/or arginine moieties). For example, it is a polylysine or polyarginine moiety. Amino acid side chains may further provide additional branches or an $R^1$ or $R^2$ group (e.g., a terminal $R^1$ or $R^2$ group). For example, in the case of a polylysine dendritic moiety, the nitrogen of the lysine side chain may further react to form additional branches, or may be an $R^2$ group. Different moieties (e.g., functional groups) may be selectively installed at selected end groups of the dendritic moiety using orthogonal protecting group strategies.

The charged amphiphilic dendrimers or amphiphilic telodendrimers may be used to stabilize proteins. The type of charge, the number of charged groups, the ratio of charged groups to hydrophobic groups (if present), the spatial orientation of the charged groups, and/or the density of the charged groups can be selected to stabilize a specific protein.

In an aspect, the present disclosure provides methods of making zwitterionic dendrimers and amphiphilic dendrimers or amphiphilic telodendrimers comprising one or more zwitterionic dendrons. In various examples, the methods comprise one or more solid-phase synthetic steps (e.g., one or more steps based on solid-phase peptide synthesis).

In an example, a method for making zwitterionic dendrimers comprises solid phase synthesis. Methods of solid phase synthesis are known to those skilled in the art. As an example, solid phase synthesis is performed using Rink resin and standard Fmoc methods where acylation uses activators (e.g., hydroxybenzotriazole/N, N'-diisopropylcarbodiimide (HOBt/DIC) activation). Additional activators include, but are not limited to, HBTU, PyBOP, HATU, HOAt, and the like. In another example, solid phase synthesis using Boc methods is used. In an example, solid phase synthesis using any monomer described herein (e.g., amino acid residue) or combinations thereof.

In another example, synthesis is performed using a polymeric resin, which may or may not have protected nucleophiles (e.g., Fmoc-protected Rink resin). In the case of polymeric resins having protected nucleophiles, the polymeric resin is deprotected (e.g., using 20% 4-methylpiperidine in dimethylformamide (DMF)). Following deprotection, if performed, the nucleophile (e.g., free amine) on the resin is coupled with an N-protected and R (side chain)-protected amino acid (e.g., Fmoc-Lys(Boc)-OH) using one or more activators in a solvent (e.g., HOBt and DIC in DMF). Following coupling, the protected N-terminus of the coupled amino acid is deprotected (e.g., the Fmoc group of the coupled Lys residue is removed using 20% 4-methylpiperidine in DMF). The free amine of the coupled amino acid (e.g., free amine of the lysine) is then coupled with a protected (e.g., spacer nucleophile is Fmoc protected) spacer (a portion of the linker) (e.g.,

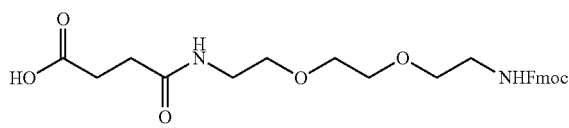

(1-(9H-fluoren-9-yl)-3,14-dioxo-2,7,10-trioxa-4,13-diaza-heptadecan-17-oic acid)) is coupled using HOBt and DIC). The N-terminal protecting (e.g., Fmoc group) is removed (the N-terminus is deprotected) from the linker (e.g., using the procedure described in FIG. 9). Following deprotection of the spacer, a free nucleophile (e.g., free amine) of the spacer is coupled with N-protected and R (side chain)-protected amino acid (e.g., Fmoc-Lys(Fmoc)-OH), which may be the same or different than the previously coupled amino acid, using one or more activators in a solvent (e.g., HOBt and DIC in DMF). Following this coupling, the process of deprotection and coupling of N-protected and R (side chain)-protected amino acid (e.g., Fmoc-Lys(Fmoc)-OH) is repeated a desired number of times. Following the final deprotection, the free nucleophiles (e.g., free amines) are coupled with zwitterionic group/moiety precursors (e.g.,

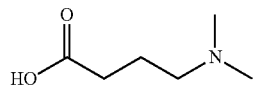

(4-(dimethylamino)butanoic acid) or) using one or more activators (e.g., HOBt and DIC). The dendrimers are then capped (e.g., using

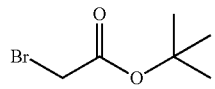

(tert-butyl 2-bromoacetate),

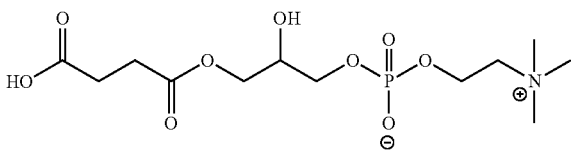 [SMILES: C[N+](C)(C)CCOP(=O)([O-])OCC(O)COC(=O)CCC(=O)O]

(2-methyl-3-((5-methylhexa-1,5-dien-2-yl)oxy)propyl (2-(trimethylammonio)ethyl)phosphoramidate) using one or more activators (e.g., HOBt and DIC). The zwitterionic dendrimers/dendrons are then cleaved from resin using a cleaving cocktail (e.g., using trifluoroacetic acid/triisopropylsilane/water (TFA/TIS/H$_2$O) (95/2.5/2.5, v/v/v)).

In an aspect, the present disclosure provides methods of amphiphilic dendrimers comprising one or more zwitterionic dendrons and one or more other dendrons (e.g., drug-binding and/or protein-binding dendrons). In various examples, the methods comprise one or more liquid-phase synthetic steps (e.g., one or more steps based on liquid-phase peptide synthesis). In various examples, the methods comprise one or more solid-phase synthetic steps (e.g., one or more steps based on solid-phase peptide synthesis), which are used for form zwitterionic dendrons, and one or more liquid-phase synthetic steps (e.g., one or more steps based on liquid-phase peptide synthesis).

In an example, the present disclosure provides methods of making amphiphilic dendrimers and amphiphilic telodendrimers comprising one or more zwitterionic dendrons and one or more other dendrons (e.g., drug-binding and/or protein-binding dendrons) comprising one or more liquid phase synthetic steps (e.g., one or more steps based on liquid-phase peptide synthesis).

In an example, a linker of a zwitterionic dendron is coupled with an N-protected and R (side chain)-protected amino acid (e.g., Fmoc-Lys(Fmoc)-OH) using one or more activators (e.g., HOBt and DIC in DMF). The protecting groups of the N-protected and R (side chain)-protected amino acid (e.g., Fmoc-Lys(Fmoc)-OH) are removed (e.g., using 20% 4-methylpiperidine in dimethylformamide (DMF)) and a second N-protected and R (side chain)-protected amino acid (e.g., Fmoc-Lys(Fmoc)-OH), which may be the same or different than the first coupled amino acid, is coupled using one or more activators (e.g., HOBt and DIC in DMF). Following the coupling of the second amino acid, the protecting groups of the second N-protected and R (side chain)-protected amino acid (e.g., Fmoc-Lys(Fmoc)-OH) are removed (e.g., using 20% 4-methylpiperidine in dimethylformamide (DMF)). Following deprotection, N-protected and R (side chain)-protected amino acid (e.g., Fmoc-Arg(Pbf)-OH)), which may be the same or different than the first and/or coupled amino acid, is coupled using one or more activators (e.g., HOBt and DIC in DMF). Following the coupling, the protecting groups are removed (e.g., using 20% 4-methylpiperidine in dimethylformamide (DMF)), and the amines are capped with a capping group (e.g.,

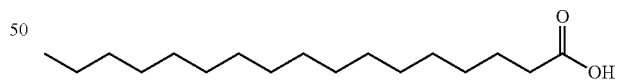

(heptadecanoic acid)). Following capping, all remaining protecting groups are removed (e.g., Pbf groups are cleaved using dichloromethane and TFA (50/50, v/v)), resulting in the completed zwitterionic amphiphile.

In another example, D-CB$_{16}$—NH$_2$ is coupled with Fmoc-Lys(Fmoc)-OH using HOBt and DIC in DMF as activators. The amines are deprotected as described above. Following deprotection, a second Fmoc(Lys(Fmoc)-OH is coupled using the same chemistry as described above. The amines are deprotected and the amines are coupled with Fmoc-Arg(Pbf)-OH. Fmoc groups are deprotected as described above, and the free amines are capped using heptadecanoic acid. The Pbf groups are cleaved using dichloromethane and TFA (50/50, v/v).

In various examples, a method of making a zwitterionic dendrimer or telodendrimers comprising one or more zwitterionic dendrons comprises one or more of the steps described above or in the examples described herein.

Nanocarriers. In an aspect, the present disclosure provides nanocarriers comprising amphiphilic dendrimers and/or amphiphilic telodendrimers. In an embodiment, a composition comprises an aggregate of a plurality of the amphiphilic dendrimers and/or amphiphilic telodendrimers that form a nanocarrier having a hydrophobic core and a hydrophilic exterior. The nanocarriers may comprise dendrimers having a plurality of cross-linked groups (e.g., photo-crosslinked groups). In an embodiment, a composition comprises an aggregate of a plurality of the dendrimers having a plurality of crosslinked groups (e.g., photo-crosslinked groups) that form a nanocarrier having a hydrophobic core and a hydrophilic exterior.

The nanocarrier may be a dendrimer micelle. A dendrimer micelle is a nanoconstruct formed by the self-assembly of dendrimer/dendrimers in aqueous solution. The dendrimer micelle can serve as a nanocarrier to load various types of therapeutics (e.g., drugs such as, for example, hydrophobic drugs, peptides, proteins, etc.).

The nanocarriers (e.g., dendrimer micelles) can have a multiple layer (e.g., three-layer) structure comprising an intermediate layer. In an embodiment, the intermediate layer comprises one or more therapeutic agents or non-therapeutic agent chemical compounds (e.g., imaging agents). In an embodiment, the intermediate layer does not comprise one or more therapeutic agents or non-therapeutic agent chemical compounds (e.g., imaging agents). The therapeutic agents (e.g., drugs) and/or non-therapeutic agent chemical compounds (e.g., imaging agents) are complexed and/or conjugated to the intermediate layer. The intermediate layer can comprise therapeutic agents such as, for example, hydrophilic therapeutic agents, hydrophobic therapeutic agents, amphiphilic therapeutic agents, polar therapeutic agents, non-polar therapeutic agents, or combinations thereof. Examples of suitable therapeutic agents are disclosed herein.

Empty nanocarriers were examined to be nontoxic in cell culture and the drug-loaded nanoformulations exhibited the similar potency in killing cancer cells in vitro, and better anticancer effects in vivo, due to the tumor targeted drug delivery. The resulting nanocarriers exhibit superior drug loading capacity and stability. The side toxicities of the chemodrugs were significantly reduced via nanoformulation. The optimized nanoparticle is able to target delivery of the payload chemo drugs to the cancer site. As a result, custom designed dendrimer nanotherapeutics significantly improve the anticancer effects in vivo.

Empty nanocarriers were examined to be nontoxic in cell culture and the protein-loaded nanoformulations exhibited the similar potency in killing cancer cells in vitro. The resulting nanocarriers exhibit superior protein loading capacity and stability. The optimized nanoparticle is able to targeted deliver the payload cytotoxic proteins to the cancer site.

The nanocarriers (e.g., dendrimer micelles) can have a multiple layer (e.g., a two-layer or three-layer) structure. The three-layer structure comprises an intermediate layer. The empty nanocarriers were examined to be nontoxic in cell culture and the protein-loaded nanoformulations exhibited the similar potency in killing cancer cells in vitro. The resulting nanocarriers exhibit superior protein loading capacity and stability. The optimized nanoparticle is able to targeted deliver the payload cytotoxic proteins to the cancer site.

The amphiphilic dendrimers and/or amphiphilic telodendrimers of the present disclosure can aggregate to form nanocarriers with a hydrophobic core, an intermediate layer (e.g., a functional reactive layer), and a hydrophilic exterior. In an embodiment, a plurality of dendrimers aggregate to form nanocarriers with a hydrophobic core and a drug-conjugated intermediate layer and a hydrophilic exterior. In an embodiment, the disclosure provides a nanocarrier having an interior and an exterior, the nanocarrier comprising a plurality of the dendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG) of each compound self-assembles on the exterior of the nanocarrier.

In an embodiment, the nanocarrier comprises a hydrophobic therapeutic agent (e.g., a hydrophobic drug) in the core and a therapeutic agent in the intermediate layer (e.g., a non-hydrophobic therapeutic agent). In an embodiment, the nanocarrier further comprises an imaging agent.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic therapeutic agents (e.g., a hydrophobic drugs) and non-hydrophobic therapeutic agents (e.g., a non-hydrophobic drugs) that are sequestered in the interior of the nanocarriers of the present disclosure.

The dendrimer micelles can be designed such that each of the therapeutic agents carried will have a different release profile. Examples of conditions that can affect the release profile of carried therapeutic agents include time and biological environment.

The nanocarrier may comprise two or more different dendrimer/drug constructs. Each of the two or more different dendrimer polymers can each be designed for a different drug combinations (i.e., the affinity layer of each dendrimer can be tuned to different drugs or different therapeutic agents can be conjugated to the intermediate layer of each dendrimer).

For example, each of the dendrimers can be associated (e.g., sequestered) with drugs (e.g., a different drug combinations) in separate reactions. Subsequently, the two or more dendrimer/drug combinations can be combined under such conditions that they form micelles containing a mix of dendrimer polymer/drug constructs. If, for example, the micelles contain 100 or so individual dendrimers, it is expected that the "mixed" micelles will contain stochastic mix of the two or more drugs. The average composition will depend upon the ratio of the 2 or more dendrimer polymer/drug constructs in the mixture. The "mixed" micelles can be used to deliver three or more drugs at the same time in a predetermined ratio (e.g., where the ratio is based on the relative starting amounts of the 3 or more drugs).

In the "mixed" micelle embodiment, it may be desirable that each dendrimer have two different end groups ($R^1$ and $R^2$), where $R^1$ is tuned for drug complexation and $R^2$ is tuned to provide drug affinity to make the various polymer/drug combinations compatible (for example, rhein for DOX; cholic acid for PTX, coumarin for SN-38 loading).

Drugs that can be sequestered in the nanocarriers or linked to the conjugates of the present disclosure include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure.

Other drugs useful in the present disclosure also include radionuclides, such as $^{67}Cu$, $^{90}Y$, $^{123}I$, $^{125}I$, $^{131}I$, $^{177}Lu$, $^{188}Re$, $^{186}Re$ and $^{211}At$. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

Some embodiments of the present disclosure provide nanocarriers wherein each amphiphilic compound $R^1$, $R^2$, is independently cholic acid, allocholic acid, pythocholic acid, avicholic acid, deoxycholic acid, or chenodeoxycholic acid.

In an embodiment, the nanocarrier comprises a plurality of charged dendrimer compounds. In an embodiment, the nanocarrier comprises one or more charged proteins. The nanocarriers comprising one or more charged proteins may have a diameter of 5 nm to 50 nm, including all integer nm values and ranges therebetween. In an embodiment, the nanocarriers comprising one or more charged proteins may have a diameter of 10 nm to 30 nm.

The dendrimers of the present disclosure can aggregate to form nanocarriers with a hybrid hydrophobic/polyelectrolic core, optionally, an intermediate layer (e.g., a reversible crosslinkable layer), and a hydrophilic exterior. In an embodiment, a plurality of dendrimers aggregate to form nanocarriers with a hydrophobic and polyelectrolic core and a hydrophilic exterior. In an embodiment, the disclosure provides a nanocarrier having an interior and an exterior, the nanocarrier comprising a plurality of the dendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG) of each compound self-assembles on the exterior of the nanocarrier. The dendrimers may encapsulate or form a layer on (e.g., a layer on at least a part of) one or more protein.

The dendrimers can be designed such that each of the proteins carried will have a different release profile. Examples of conditions that can affect the release profile of carried proteins include time and biological environment.

The nanocarrier may comprise two or more different dendrimer/protein constructs. Each of the two or more different dendrimer polymers can each be designed for a different protein combinations (i.e., the affinity layer of each dendrimer can be tuned to different proteins).

The nanocarrier can further comprise a polycation material. Examples of polycation materials include, but are not limited to, cationic polymers such as, for example, polyethylenimine (PEI), polylysine, or poly(dimethylaminoethyl methacrylate) (PDMAEMA). Combinations of polycation materials can be used. In various examples, a polycationic material (e.g., a polymer) has a molecular weight of 500 Daltons to 100 kiloDaltons, including all integer Dalton values and ranges therebetween. Various ratios of protein(s) to polycation material(s) can be used. For example, the ratio of protein(s) to polycation material(s) (mass ratio) is 1:1 to 1:40, including all ratios to 0.01 therebetween. In another example, the ratio of protein(s) to polycation material(s) (mass ratio) is 1:2. Various ratios of polycation material(s) to dendrimer(s) can be used. For example, the ratio of polycation material(s) to dendrimer(s) (mass ratio) is 1:0.05 to 1:20, including all ratios to 0.01 therebetween. In another example, the ratio of polycation material(s) to dendrimer(s) (mass ratio) is 1:1. In an example, the ratio of polycation material(s) to dendrimer(s) (mass ratio) is 1:1 to 1:40 and the ratio of polycation material(s) to dendrimer(s) (mass ratio) is 1:0.05 to 1:20.

The protein or protein mixtures can be dissolved in phosphate buffered saline, and dendrimer(s) in phosphate buffered saline are rapidly added into protein solution. The proteins will interact (e.g., be encapsulated) mainly by the dendrimers through electrostatic interaction, hydrogen bonding, and hydrophobic-hydrophobic interaction.

For example, each of the dendrimers can be associated with (e.g., encapsulate) proteins (e.g., a different protein combinations) in separate reactions. Subsequently, the two or more dendrimer polymer/protein combinations can be combined under such conditions that they form micelles containing a mix of dendrimer polymer/protein constructs. If, for example, the micelles contain 100 or so individual dendrimers, it is expected that the "mixed" micelles will contain stochiastic mix of the two or more proteins. The average composition will depend upon the ratio of the 2 or more dendrimer polymer/proteins constructs in the mixture. The "mixed" micelles can be used to deliver three or more proteins at the same time in a predetermined ratio (e.g., where the ratio is based on the relative starting amounts of the 3 or more proteins).

In the "mixed" micelle embodiment, it may be desirable that each dendrimer have two different end groups ($R^1$ and $R^2$), where $R^1$ is tuned for particle size, protein stability and hydrophobic interactions and $R^2$ is tuned to provide a charged protein interaction and stabilization.

Some embodiments of the present disclosure provide nanocarriers wherein each amphiphilic compound $R^1$, $R^2$, is independently cholic acid, allocholic acid, pythocholic acid, avicholic acid, deoxycholic acid, or chenodeoxycholic acid.

Protein-loaded dendrimer nanoparticles of the present disclosure are stable in particle sizes as detected by DLS analysis upon storage in PBS or saline at 4° C. and room temperature within the monitoring duration for 3 months. The activity of cytotoxic protein (DTAT13) and peptide-drug conjugates are remained the same as free therapeutics in cancer cell killing in cell culture.

Protein therapeutics can be released out from the complex via the competition by the high concentration of serum proteins in vivo. The release rate can be tuned by the adjusting the protein binding affinity of dendrimers. Therefore, protein-nanotherapeutics can be administrated directly for in vivo use without the need to purification of the released protein.

The dendrimers of the present disclosure can be used to, for example, encapsulate antibodies and other therapeutic proteins and increase the therapeutic index mainly in two-fold: (1) to improve the stability of the protein therapeutics, e.g., antitoxin antibodies, during storage even at room temperature for the possible applications at rural area and military use. They can be developed as onsite-care formulations for direct administration. Antibodies will be released upon serum albumin and IgG competition of nanocarrier. It is also useful to stabilize antibody drugs for routine use to prevent the denaturation due to aggregation. (2) An even broader application is to deliver protein and antibodies reagents into cells, for example, antibodies against intracellular proteins used in biochemistry assays or pathology detections, therefore becoming therapeutic to treat various diseases.

The charged dendrimers can be present in a composition. In an embodiment, the composition comprises one or more charged dendrimers. The composition may comprise a mixture of positively charged dendrimers, a mixture of negatively charged dendrimers, or a mixture of positively and negatively charged dendrimers. In an embodiment the composition further comprises one or more proteins. In an embodiment the composition further comprises one or more drugs. The composition can have a formulation as disclosed herein. For example, the composition can be a pharmaceutical composition as described herein.

Any charged protein can be used. For example, the protein is a positively charged or negatively charged protein. In an embodiment, the protein is an imaging agent-labeled protein. In an embodiment, the composition comprises or nanocarriers encapsulate an amount of protein(s) that is 30-200% of the dendrimer present in the composition or nanocarriers by weight, including all integer weight % values and ranges therebetween.

Examples of therapeutic proteins that can be used include nucleoproteins, glycoproteins, lipoproteins, immunotherapeutic proteins, porcine somatotropin for increasing feed conversion efficiency in a pig, insulin, growth hormone, buserelin, leuprolide, interferon, gonadorelin, calcitonin, cyclosporin, lisinopril, captopril, delapril, tissue plasminogen activator, epidermal growth factor, fibroblast growth factor (acidic or basic), platelet derived growth factor, transforming growth factor (alpha or beta), vasoactive intestinal peptide, tumor necrosis factor; hormones such as glucagon, calcitronin, adrecosticotrophic hormone, follicle stimulating hormone, enkaphalins, β-endorphin, somatostin, gonado trophine, α-melanocyte stimulating hormone. Additional examples include bombesin, atrial naturiuretic peptides and luteinizing hormone releasing (LHRH), substance P, vasopressins, $\alpha$-globulins, transferrins, fibrinogens, β-globulins, prothrombin (bovine), ceruloplasmin, $\alpha_2$-glycoproteins, $\alpha_2$-globulins, fetuin (bovine), albumin and prealbumin, bovine serum albumin, green fluorescent protein, diphtheria toxins, lysozyme, trypsin, cytochrome c, saporin, ribonuclease A, IgG, and antibodies.

The nanocarriers may comprise one or more drugs. The drugs can be therapeutic agents. The drugs may be sequestered in the nanocarriers (e.g., sequestered in one or more of the layers of a dendrimer) or linked to the conjugates of the present disclosure. Examples of drugs include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17alpha-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure.

In an aspect, the present disclosure provides uses of dendrimers comprising one or more zwitterionic dendrons of the present disclosure. The dendrimers can be used, for example, in methods of treatment.

Method of treating. The compositions of and nanocarriers of the present disclosure can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier. In an embodiment, compositions comprising the dendrimers are used in a method for treating a disease.

In some embodiments, the present disclosure provides a method of treating a disease, including administering to a subject in need of such treatment a therapeutically effective amount of a nanocarrier of the present disclosure, where the nanocarrier includes at least two drugs. The drugs can be a covalently attached to a conjugate of the nanocarrier. In some embodiments, the drugs are a hydrophobic drug, sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present disclosure can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present disclosure include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present disclosure are useful for the treatment of infection by pathogens such as viruses, bacteria, fungi, and parasites. Other diseases can be treated using the nanocarriers of the present disclosure.

Compositions or nanocarriers of the present disclosure can be used to treat any disease requiring the administration of a protein, such as, for example, by sequestering a protein in the interior of the nanocarrier, and delivering said protein to a target. The protein(s) can be delivered systemically or intracellularly. In an embodiment, compositions comprising the dendrimers are used in a method for treating a disease.

In some embodiments, the present disclosure provides a method of treating a disease, including administering to a subject in need of such treatment a therapeutically effective amount of a composition or nanocarrier of the present disclosure, where the nanocarrier includes an encapsulated protein.

The compositions or nanocarriers of the present disclosure can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the compositions or nanocarriers of the present disclosure include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the compositions or nanocarriers of the present disclosure are useful for the treatment of infection by pathogens such as viruses, bacteria, fungi, and parasites. Other diseases can be treated using the compositions or nanocarriers of the present disclosure.

Formulations. The nanocarriers of the present disclosure can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present disclosure (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

Pharmaceutical preparations useful in the present disclosure also include extended-release formulations. In some embodiments, extended-release formulations useful in the present disclosure are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present disclosure, the pharmaceutical compositions can be used alone, or in combination with other therapeutic or diagnostic agents.

Administration. The nanocarriers of the present disclosure can be administered as frequently as necessary, including hourly, daily, weekly or monthly. The compounds utilized in the pharmaceutical method of the disclosure are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present disclosure should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present disclosure, the pharmaceutical compositions can be used alone, or in combination with other therapeutic or diagnostic agents. The additional drugs used in the combination protocols of the present disclosure can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present disclosure, separately or at different times.

Method of imaging. In another embodiment, compositions comprising the dendrimers are used in imaging methods. In some embodiments, the present disclosure provides a method of imaging, including administering to a subject to be imaged, an effective amount of a nanocarrier of the present disclosure, wherein the nanocarrier includes an imaging agent. In other embodiments, the method of treating and the method of imaging are accomplished simultaneously using a nanocarrier having a hydrophobic therapeutic agent, a non-hydrophobic therapeutic agent and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present disclosure include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I $^{124}$I, $^{125}$I, $^{129}$I, $^{131}$I, $^{137}$CS, $^{177}$Lu, $^{186}$Re, $^{188}$Re, $^{211}$At, Rn, Ra, Th, U, Pu and $^{241}$Am.

The steps of the method described in the various embodiments and examples disclosed herein are sufficient to carry out the methods of the present disclosure. Thus, in an example, the method consists essentially of a combination of the steps of the methods disclosed herein. In another example, the method consists of such steps.

The following Statements provide embodiments and/or examples of compounds (e.g., an amphiphilic dendrimer or amphiphilic telodendrimer), nanocarriers, methods, and zwitterionic dendrons of the present disclosure:

Statement 1. A compound (e.g., an amphiphilic dendrimer or amphiphilic telodendrimer) having the following structure:

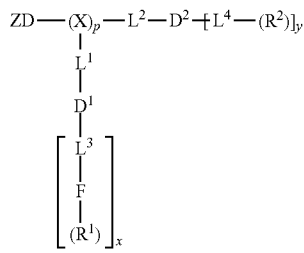
(I)

where ZD is a zwitterionic group comprising one or more zwitterionic dendron, zwitterionic linear group (which can be formed from a zwitterionic polymer, which is linear or branched), or a combination thereof (the group may be linked to the dendrimer via a linking group such as, for example, a lysine moiety); X is optionally present and is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), and a plurality of end groups; $D^2$ is a dendritic polymer moiety having one or more branched monomer units (X), and a plurality of end groups; F is independently optional a functional reactive moiety selected for specific drug conjugation/complexation via labile bonds, reversible complexes or charge interactions; $R^1$ is an end group of the dendritic polymer and is independently at each occurrence in the compound selected from the group consisting of groups formed from or groups comprising the end groups (e.g., unreacted end groups) of the dendritic polymer, hydrophobic group, a hydrophilic group, an amphiphilic group, a reversible photocrosslinking group, a drug (e.g., a hydrophobic drug), catechols, crosslinkable groups (e.g., boronic acid, cisdiols, amine, carboxylic acids, acryl groups, epoxide, thiol groups, maleimide, C═C double bond, azide, alkyne, coumarin and chlorogenic acid, etc.), boronic acids, carboxylic acids, acylhydrazines, hydroxyl, amines, thiols and ketones for labile bond formation, a positively charged moiety (e.g., primary, secondary or tertiary amines for gene delivery), amphiphilic groups (e.g. cholic acid, riboflavin, chlorogenic acid), chelating groups (e.g., amines, aromatic imines, and carboxylic acids), and thiol groups for metallic drug chelation); each $R^2$ is an end group of the dendritic polymer and is independently at each occurrence in the compound selected from the group consisting of groups formed from or groups comprising positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups, such as sugars, peptides, and hydrophilic polymers), or hydrophobic groups, such as, for example, alkanes (e.g., long-chain alkanes) (e.g., $C_1$-$C_{50}$) and fatty acids (e.g., $C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine)), or amphiphilic groups (e.g. cholic acid, riboflavin, chlorogenic acid), a reversible photocrosslinking group, and a drug; subscript x is an integer from 1 to 64 (e.g., 1, 2, 3, 4, 5, 6, 7, or 8), subscript y is an integer from 1 to 64 (e.g., 2, 3, 4, 5, 6, 7, 8, 9, 10, 11, 12, 13, 14, 15, or 16), and subscript p is an integer from 0 to 32, (e.g., 1, 2, 3, or 4) or 1 to 32 (e.g., 1, 2, 3, or 4).

Statement 2. A compound according to Statement 1 having the following structure:

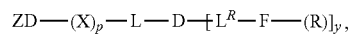

where ZD is a zwitterionic group comprising one or more zwitterionic dendron, zwitterionic polymer group (which can be linear or branched), or a combination thereof (the group may be linked to the dendrimer via a linking group such as, for example, a lysine moiety);
X is optionally present and is a branched monomer unit;
each L is independently optional and is a linker group;
each $L^R$ is independently optional and is a linker group;
D is a dendritic polymer moiety having one or more branched monomer units (X), and a plurality of end groups;
F is independently optional a functional reactive moiety selected for specific drug conjugation/complexation via labile bonds, reversible complexes or charge interactions;
R is an end group of the D dendritic polymer moiety and is independently at each occurrence in the compound selected from the group consisting of groups formed from or comprising: end groups (e.g., unreacted end groups) of the dendritic polymer, hydrophobic groups (e.g., groups formed from or groups comprising one or more steroid, alkane (e.g., long-chain alkane) (e.g., $C_1$-$C_{50}$), fatty acid (e.g., $C_1$-$C_{50}$), lipid (e.g., cholesterol, steroids, and the like), vitamins (e.g., vitamins E, D, K, and the like), naturally-occurring compound (e.g., bile acids, terpenoids, and the like), herbal extract (e.g., rhein, coumarin, curcumin, flavin, isoflavin, and the like), aromatic molecule (e.g., benzoic acids, histidine, tyrosine, and the like), esters (e.g., polylactide, polyglycolid acid, and the like), and polymer (e.g., PLGAs, polycaprolactones, polylactic acids, polyglycolic acids, polystyrenes, polyisoprenes, polyvinyl pyridines, and the like)), hydrophilic groups (e.g., groups formed from or groups comprising one or more sugar, polyphenol, heterocyclic molecule, carboxylic acid, and the like), amphiphilic groups (e.g., groups formed from or groups comprising one or more cholic acid, riboflavin, chlorogenic acid, and the like), drugs (e.g., groups formed from or comprising one or more doxorubicin, bortezomib, cisplatin, and the like) (e.g., hydrophobic drugs), crosslinkable groups (e.g., groups formed from or comprising one or more boronic acid, cis diol, amines, catechol, carboxylic acid, acryl group, epoxide, thiol group, maleimide, alkene (e.g., groups comprising one or more carbon-carbon double bond), azide, alkyne, coumarin, chlorogenic acid, acylhydrazine, hydroxyl, amine, thiol, ketone, and the like), a positively charged group/moiety (e.g., primary, secondary or tertiary amines, for example, for gene delivery), chelating groups (e.g., groups formed from or comprising one or more amine, aromatic imine, carboxylic acid, thiol group (for, for example, metallic drug chelation), and positively or negatively charged groups (e.g., groups formed from or comprising one or more arginine, lysine, guanidine, amine, heterocyclic molecule, amidine, tetrazole, hydroxyl, carboxylic acid, phosphate, sulfonate, methanesulfonamide, sulfonamide, oxalic acid, charged derivatives of each, and the like);

subscript y is an integer from 2 to 64 (e.g., 2, 3, 4, 5, 6, 7, 8, 9, 10, 11, 12, 13, 14, 15, or 16), and subscript p is an integer from 0 to 32 (e.g., 1, 2, 3, or 4).

Statement 3. A compound according to Statement 1 or 2, where ZD is selected from the group consisting of: zwitterionic polymers having the following structure:

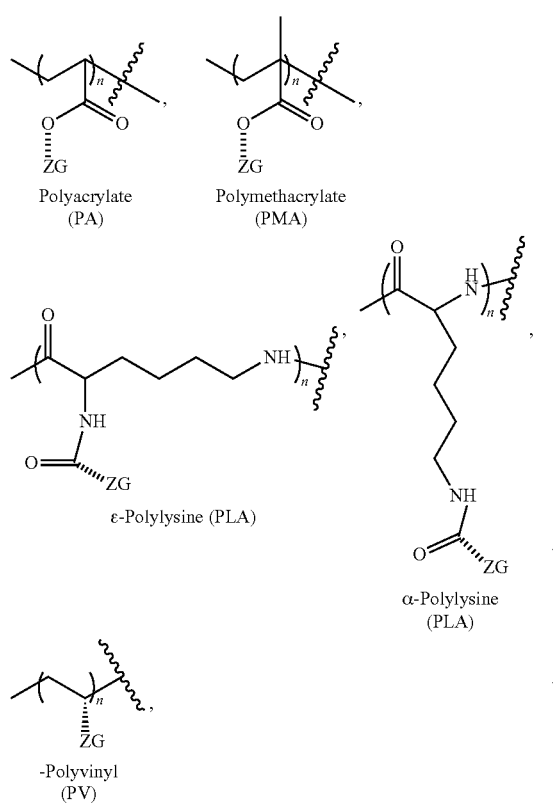

where n is, for example, 2-500, and at each occurrence in the polymer the hashed line is a spacer (e.g., a linker) or a bond, and ZG is selected from the group consisting of:

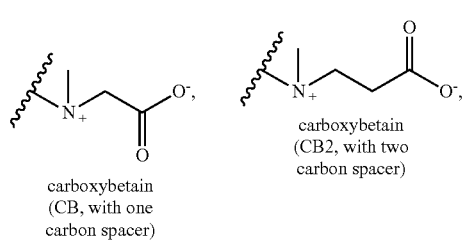

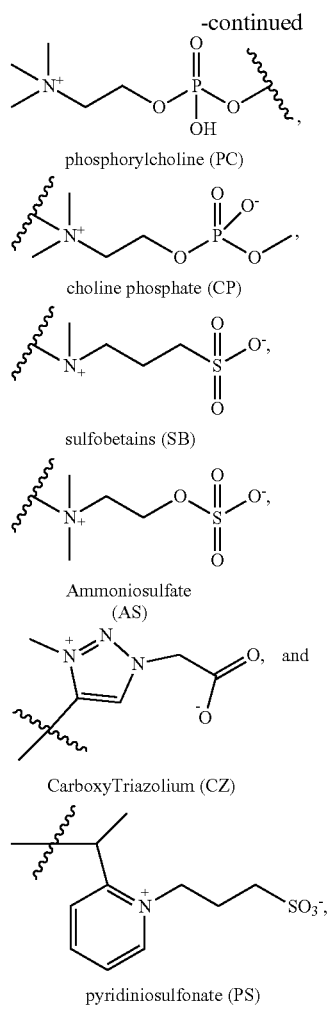

and
zwitterionic dendrimers having the following structure:

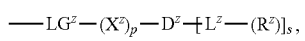

$$—LG^z—(X^z)_p—D^z—[L^z—(R^z)]_s,$$

where $LG^z$ is optionally present (and is a linking group covalently bonding the ZG group to an $X^z$ or $D^z$ and is formed by, for example, reaction of a ZLG and a reactive group (e.g., an carboxylic group) of an $X^z$ or $D^z$);

$X^z$ is optionally present and is a branched monomer unit;

each $L^z$ is independently optional and is a linker group;

$D^z$ is a dendritic polymer moiety having one or more branched monomer units ($X^z$), and a plurality of end groups ($R^z$);

$R^z$ is an zwitterionic end group of the dendritic polymer and is independently at each occurrence in the compound selected from the group consisting of carboxybetain (CB) groups/moieties, phosphorylcholine (PC) groups/moieties, choline phosphate (CP) groups/moieties, sulfobetaines (SB) groups/moieties, ammoniosulfate groups/moieties, carboxytriazolium groups/moieties, pyridiniosulfonate groups/moieties, targeting moieties and combinations thereof (with the proviso that at least one of the $R^z$ groups is a zwitterionic group);

subscript s is an integer from 1 to 64 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32); and subscript p is an integer from 1 to 32 (e.g., 1, 2, 3, or 4); and combinations thereof.

Statement 4. A compound of any of the preceding Statements, where all of the R groups are the same.

Statement 5. A compound of Statement 4, where the R groups are selected from hydrophobic groups and amphiphilic groups (e.g., groups formed from or comprising one or more cholic acid, riboflavin, chlorogenic acid, vitamin E, fatty acid, cholesterol, rhein, coumarin, isoflavin, and the like).

Statement 6. A compound of Statement 4 or 5, where the R groups are selected from groups formed from or comprising one or more cholic acid, riboflavin, and rhein.

Statement 7. A compound of any one of Statements 1-3, where at least one of the R groups is different than the other R groups.

Statement 8. A compound of Statement 7, where the R groups are selected from hydrophobic groups and amphiphilic groups (e.g., groups formed from or comprising one or more cholic acid, riboflavin, chlorogenic acid, vitamin E, fatty acids, cholesterol, rhein, coumarin, isoflavin, and the like).

Statement 9. A compound of Statement 7 or 8, where at least one R groups is:

i) one or more group formed from or group comprising cholic acid, and the remaining R groups are selected from groups formed from or comprising one or more riboflavin, chlorogenic acid, rhein, vitamin E, cholesterol, and combinations thereof;

ii) one or more group formed from or group comprising riboflavin, and the remaining R groups are selected from groups formed from or comprising one or more cholic acid, chlorogenic acid, rhein, vitamin E, cholesterol, and combinations thereof; or iii) one or more chlorogenic acid, and the remaining R groups are selected from groups formed from or comprising one or more cholic acid, riboflavin, vitamin E, cholesterol, and combinations thereof.

Statement 10. A compound of any one of Statements 1-3, where at least one of the R groups is a charged group (e.g., groups formed from or comprising one or more primary amine, carboxylate, phosphate, sulfonate, guanidium, oxalic acid and hydrophobic groups such as, for example, groups formed from or comprising one or more cholic acid, riboflavin, chlorogenic acid, vitamin E, fatty acids, cholesterol, rhein, coumarin, isoflavin, and the like).

Statement 11. A compound of Statement 10, where the R groups are selected from charged groups, hydrophobic groups, hydrophilic groups, amphiphilic groups, and combinations thereof.

Statement 12. A compound of Statement 10 or 11, where the at least one charged R group is a group comprising one or more guanidinium group, protonated amine, carboxylate, and combinations thereof (e.g., a group formed from the side-chain of an amino acid such as, for example, arginine, lysine, glutamic acid, aspartic acid, and the like)

Statement 13. A compound of any one of the preceding Statements, where at each occurrence in the compound the branched monomer unit (X) is independently selected from the group consisting of a diamino carboxylic acid moiety, a dihydroxy carboxylic acid moiety, and a hydroxyl amino carboxylic acid moiety.

Statement 14. The compound of any one of the preceding Statements, where at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

Statement 15. A compound of Statement 13 or 14, where the diamino carboxylic acid moiety is an amino acid moiety.

Statement 16. A compound of any one of Statements 13-15, where i) each branched monomer unit X is lysine moiety; or ii) the branched monomer units are at least one lysine, and at least one of arginine, aspartic acid, or glutamic acid.

Statement 17. A compound of any one of the preceding Statements, where at each occurrence in the compound the linker L, $L^R$, and $L^Z$ each are independently selected from the group consisting of a polyethylene glycol moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety.

Statement 18. The compound of Statement 17, where at each occurrence in the compound the linker L, $L^R$, and $L^Z$ are independently selected from the group consisting of:

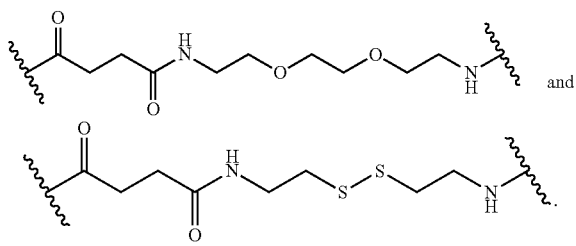

Statement 19. A compound of any one of the preceding Statements, where the compound further comprises one or more protein associated with the compound.

Statement 20. A compound of any one of the preceding Statements, where the compound further comprises one or more drug associated with the compound.

Statement 21. A nanocarrier comprising a plurality of compounds of any of the preceding claims.

Statement 22. A nanocarrier of Statement 21, where at least one of the compounds of the plurality compounds is structurally distinct from rest of the plurality of compounds.

Statement 23. A nanocarrier of any one of Statements 21 or 22, where the nanocarrier further comprises one or more biomolecule (e.g., nucleic acid, protein, peptide, or a combination thereof).

Statement 24. A nanocarrier of any one of Statements 21-23, where the nanocarrier further comprises one or more drug.

Statement 25. A nanocarrier of any one of Statements 21-24, where the nanocarrier further comprises an imaging agent.

Statement 26. A method of delivering a protein and/or drug to an individual (e.g., an individual in need of the protein and/or drug) comprising administering to the individual a compound of any one of Statements 1-20 or a nanocarrier of any one of Statements 21-25.

Statement 27. A zwitterionic dendron having the following structure:

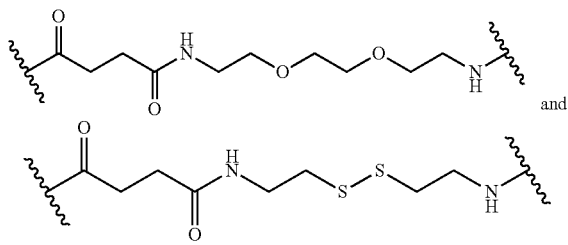

and where ZLG is optionally present and is a zwitterionic dendron linking group; X is optionally present and is a branched monomer unit; each $L^z$ is independently optional and is a linker group; $D^z$ is a dendritic polymer moiety having one or more branched monomer units (X), and a plurality of end groups; $R^z$ is an zwitterionic end group of the dendritic polymer and is independently at each occurrence in the compound selected from the group consisting of carboxybetain (CB) groups/moieties, phosphorylcholine (PC) groups/moieties, choline phosphate (CP) groups/moieties, sulfobetaines (SB), targeting moieties and combinations thereof (with the proviso that at least one of the $R^z$ groups is a zwitterionic group); subscript s is an integer from 1 to 64 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32); and subscript p is an integer from 1 to 32 (e.g., 1, 2, 3, or 4). In the case where the ZLG is not present, the dentritic polymer moiety or branched monomer unit (X) can be functionalized with various terminal groups.

The following examples are presented to illustrate the present disclosure. The examples are not intended to limiting in any manner.

Example 1

The following is an example of the preparation, characterization, and use of charged dendrimers of the present disclosure.

We describe the development of Janus-type dendritic macromolecules which integrate the contradicting protein binding and non-fouling properties into a single entity. The asymmetric polylysine-based dendritic amphiphile is composed of a zwitterionic dendron and a therapeutic binding dendron, which self-assembles into a nanoparticle as delivery vehicle with a zwitterionic surface and a therapeutics-loaded core. A combination of solid-phase and liquid-phase peptide syntheses was adopted for the polylysine polymer production. Carboxybetain (CB) and phosphorylcholine (PC) zwitterionic moieties were selected to decorate one-side dendron surface to afford anti-fouling property, which improve the stability of nanoparticle. Another half dendron was asymmetrically functionalized with therapeutics binding moieties, which were rationally designed and tailored to provide demanding affinities to either protein or small molecular drugs. These amphiphilic Janus-type amphiphiles self-assemble with therapeutics into <50 nm micelles. Zwitterionic layers provide nanoparticle stealth surfaces, which show high resistance to the nonspecific binding of biological molecules in physiological conditions. The protein loading in our zwitterionic nanoparticles was investigated in vitro by DLS, TEM, BLI, electrophoresis and FRET assay. We further demonstrated the intracellular delivery of protein by the nanoparticles into SKOV-3 cells.

We prepared an asymmetrical dendrimer using polylysine backbone by orthogonal amine-protecting chemistry. Protein or drug binding moieties will be introduced on the periphery of one-half dendron; and zwitterionic fragments will be decorated on the periphery of another-half dendron. The resulting dendrimer has distinct both chemical asymmetry and the functional disparity, e.g. protein binding v.s. anti-fouling properties, which defines such dendrimer with a deserved "Janus" character.

Stepwise and repeated solution-phase reactions ensure the precise control over the well-defined chemical structure of dendrons. However, the tedious purifications are highly demanded and time consuming for dendrimer synthesis. Therefore, we combine solid-phase and solution phase peptide chemistry to prepare an asymmetric amphiphilic polylysine-based Janus dendrimers with zwitterionic pheripheral and drug binding functionalities for improved therapeutics delivery.

Materials. All chemicals were used as received unless otherwise specified. Rink resin was ordered from JenKem Technology USA Inc. (Allen, TX). (Fmoc)-Lys(Boc)-OH, (Fmoc)-Lys(Fmoc)-OH, trifluoroacetic acid (TFA) and Glycerylphosphorylcholine were obtained from Chem-Impex International, Inc. (Wood Dale, IL). (Fmoc)-Lys(Dde)-OH and (Fmoc)-Arg(Pbf)-OH were purchased from AnaSpec Inc. (San Jose, CA). N,N'-diisopropylcarbodiimide (DIC), N-hydroxybenzotriazole (HOBt), Succinic anhydride, 4-Dimethylaminopyridine (DMAP) and N,N-dimethylformamide, anhydrous (DMF, 99.8%) were received from Acros Organics (Belglum, NJ). N-hydroxysuccinimide (NHS), triethylamine (TEA) and all other chemicals were purchased from Sigma-Aldrich (St. Louis, MO). Tetrazolium compound [3-(4,5-dimethylthiazol-2-yl)-5-(3-carboxymethoxyphenyl)-2-(4-sulfophenyl)-2H-tetrazolium, MTS] and phenazine methosulfate were purchased from Promega (Madison, WI). Lipophilic fluorescent dye, Doxorubicin hydrochloride (DOX) and rhein were ordered from AvaChem Scientific LLC (San Antonio, TX).

Spectroscopic characterization. $^1$H and $^{13}$C NMR spectra were recorded on a 600 MHz Bruker AVANCE NMR spectrometer. Solvents employed were $D_2O$ and DMSO-$d_6$. Matrix-assisted laser desorption/ionization time-of-flight mass spectrometry (MALDI-TOF MS) spectra were collected on a Bruker Autoflex III system equipped with a Smart beam II laser source and acquired in positive, linear mode for polymers and positive, reflector mode for small compounds. Samples were prepared by depositing 1 μL aliquots of a premixed solution of sample and matrix (α-Cyano-4-hydroxycinnamic acid for small molecules and 2,5-dihydroxybenzoic acid for polymers) onto a MTP 384 target plate, polished steel TF (Bruker). Transmission electron microscopy (TEM) characterization of nanoparticle was performed on JEOL JEM-1400 operated at 80 kV. Samples were prepared by applying aliquots of a nanoparticle solution on a glow discharged carbon-coated copper grids (CF300-CU, 300 mesh, Electron Microscopy Sciences).

Negative staining was achieved using uranyl acetate solution (1%). The hydrodynamic sizes of nanoparticles were acquired by dynamic light scattering (DLS) using particle analyzer (Microtrac) equipped with equipped with 780 nm laser diode. Each apparent hydrodynamic size reported is an average of three measurements.

Synthesis of carboxyl acid derivative of glycerylphosphorylcholine (GPC-COOH). Glycerylphosphorylcholine (1.014 g, 3.93 mmol), DMAP (4-Dimethylaminopyridine, 122.17 g/mol, 253 mg, 2.07 mmol), were dissolved in 50 mL DMSO. Succinic anhydride (431 mg, 4.30 mmol) in 10 mL DMSO was added dropwise to the solution. Initially, the GPC is partially insoluble and becomes soluble when converted to GPC—COOH. The reaction mixture was vigorously stirred at room temperature for 24 h. The reaction was monitored complete by MALDI-TOF and the reaction mixture was then precipitated with cold ethyl acetate for three times. The product was dried in vacuo to yield a white solid with a mass of 1.068 g (yield, 74%). MS (MALDI-TOF MS): calculated for $C_{12}H_{24}NO_9P$ $[M]^+$: m/z=357.119. Found: $[M+H]^+$: m/z=358.882.

Synthesis of folate-lysine derivative (FA-Lys-$NH_2$). Rink amide resin was coupled with Fmoc-Lys(Boc)-OH and folic acid in a sequential produce. The Boc-deprotection and cleavage of folate-lysine derivative from resin were conducted simultaneously in TFA/$H_2O$/TIS (95/2.5/2.5). $^1$H NMR (600 MHz, DMSO) δ 8.65 (s, 1H), 8.36-8.26 (m, 1H), 8.24-8.04 (m, 1H), 8.02-7.79 (m, 1H), 7.66 (d, J=7.5 Hz, 2H), 7.40-7.18 (m, 2H), 7.03-6.90 (m, 2H), 6.66 (d, J=8.7 Hz, 2H), 4.56-4.45 (m, 2H), 4.35 (m, 1H), 4.17 (m, 1H), 3.63 (d, J=2.7 Hz, 2H), 2.80-2.72 (m, 2H), 2.37-2.16 (m, 2H), 2.14-2.02 (m, 1H), 1.91 (m, 1H), 1.67 (m, 1H), 1.57-1.43 (m, 3H), 1.36-1.23 (m, 2H). MS (MALDI-TOF MS): calculated for $C_{25}H_{32}N_{10}O_6$ $[M]^+$ m/z=568.25, Found: $[M+H]^+$ m/z=569.290, $[M+Na]^+$ m/z=591.289, $[M+K]^+$ m/z=607.302.

Synthesis of asymmetric dendrimers by SPPS. Rink amide resin. Specifically, (Fmoc)-Lys(Dde)-OH, PEG-linker-Fmoc, (Fmoc)-Lys(Fmoc)-OH were coupled sequentially following the standard peptide synthesis procedures. For the synthesis of CB dendrons, 4-(dimethylamino) butyric acid (DMBA) was initially attached at the periphery of polylysine dendron followed by the reaction with t-butyl bromoacetate in DMF at 50° C. for 72 h. For the synthesis of PC dendrons, GPC—COOH obtained above was directly added to the amine-containing dendron.

Dde-protecting group was removed by the treatment of 2% hydrazine to release free amine for the initiation of therapeutic-binding dendron synthesis. Two consecutive coupling of (Fmoc)-Lys(Fmoc)-OH yielded four branches for the attachment of therapeutic-binding moieties. Rhein was activated by EDC/DIC for the conjugation to dendrons.

Agarose gel electrophoresis assay. The electrophoresis was carried out in 1.5% agarose gel (tris-borate-EDTA (TBE) buffer) at constant current of 20 mA for 2 h. The gel was imaged by a Bio-Rad Universal Hood II Imager (Bio-Rad Laboratories, Inc.) under SYBR Green mode.

Bio-layer interferometry (BLI) study. The protein adsorption of zwitterionic polymers was investigated by BLI study using BSA as model protein. The assay was performed on Octet-RED 96 (ForteBio) using 96-well plate (Greiner Bio-One part no. 655209) at 37° C. Following the programmed steps, amine reactive biosensors (part no. 18-5029) were hydrated, activated by EDC/NHS for 300 s, immobilized with polymer of PEG, CB and GPC (pH 6, 1000 μg/mL) for 800 s, respectively, quenched by ethanolamine (pH 8.5) for 400 s, washed in PBS for 800 s. The protein adsorption was conducted with BSA in PBS at 200 μg/mL for 1000 s followed by dissociation in PBS for 1000 s.

Protein binding kinetics was conducted using Amine-Reactive Second Generation Dip and Read Biosensors (AR2G). Following defined steps, tips were hydrated and activated for 300 s in EDC/sulfo-NHS solutions (20 mM/10 mM) in $H_2O$. Next, tips were immobilized with BSA at a concentration of 50 μg/mL in acetate buffer (pH 6.0) for 1200 s followed by subsequent quenching for 300 s in a 1 M ethanolamine solution at pH 8.5. The associations of BSA with polymers were monitored at concentrations of 50, 100, 200, 300, and 400 nM for 2000 s. Dissociation of polymer was monitored for 2000 s in BSA (5 mg/mL) in PBS. Baseline-adjusted sensograms were processed by Global fit to a 1:1 binding model using ForteBio analysis software.

Results and discussion. The Janus-type zwitterionic macromolecules were constructed by a combination of SPPS and LPPS. Two zwitterionic surfaces were exploited to prevent protein adsorption. The unique zwitterionic amphiphiles were designed to integrate the seemly contradicting protein binding and protein repelling properties. Dendritic wedges with available multiple surface functionalities allows for the introduction of therapeutic binding moieties for intended delivery purpose.

Figure 10:
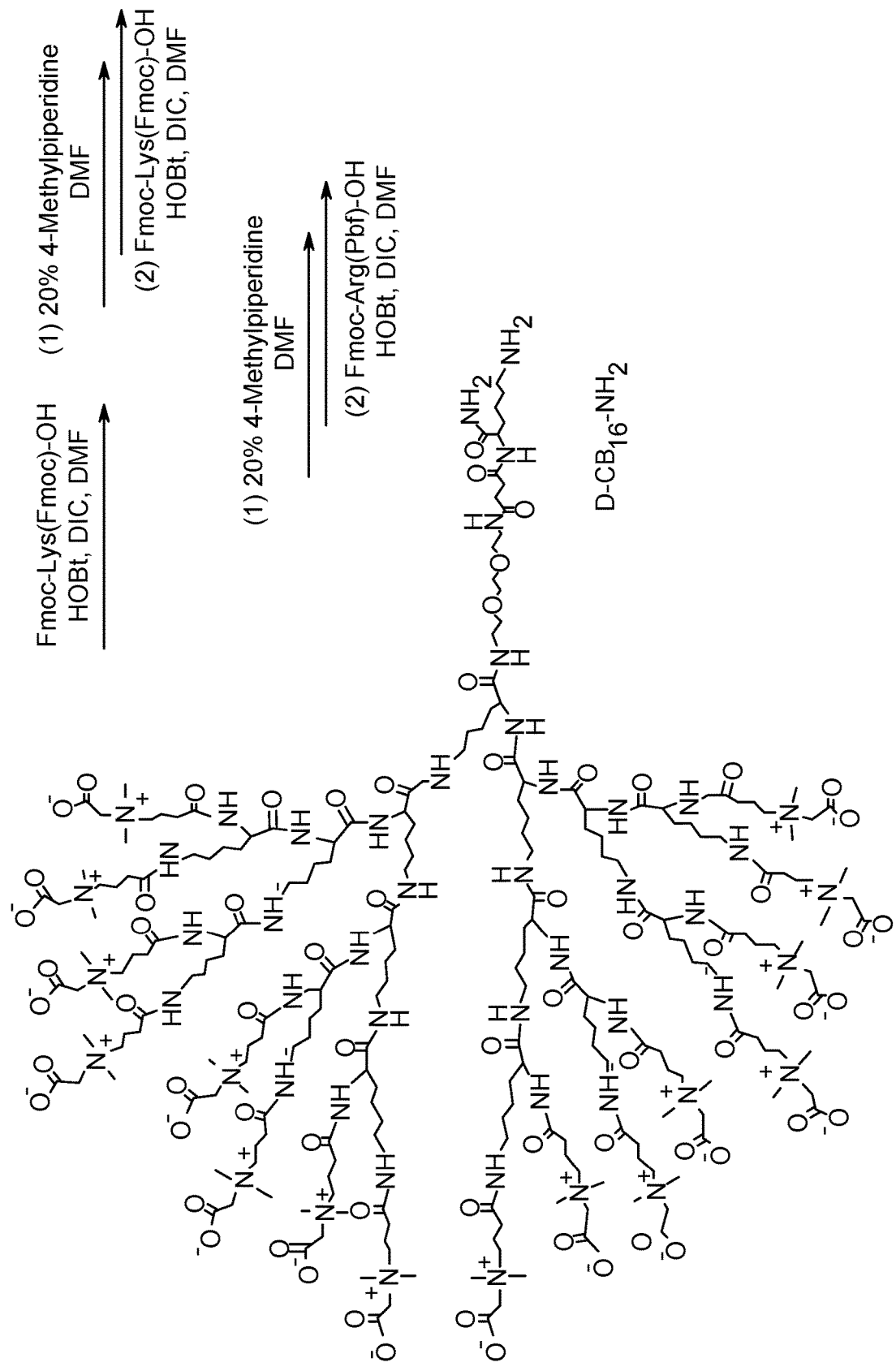
FIG. 10 shows an example of a liquid-peptide synthesis of a Janus-type dendrimer, $CB_{16}$-$Arg_4C17_4$.
Figure 10:
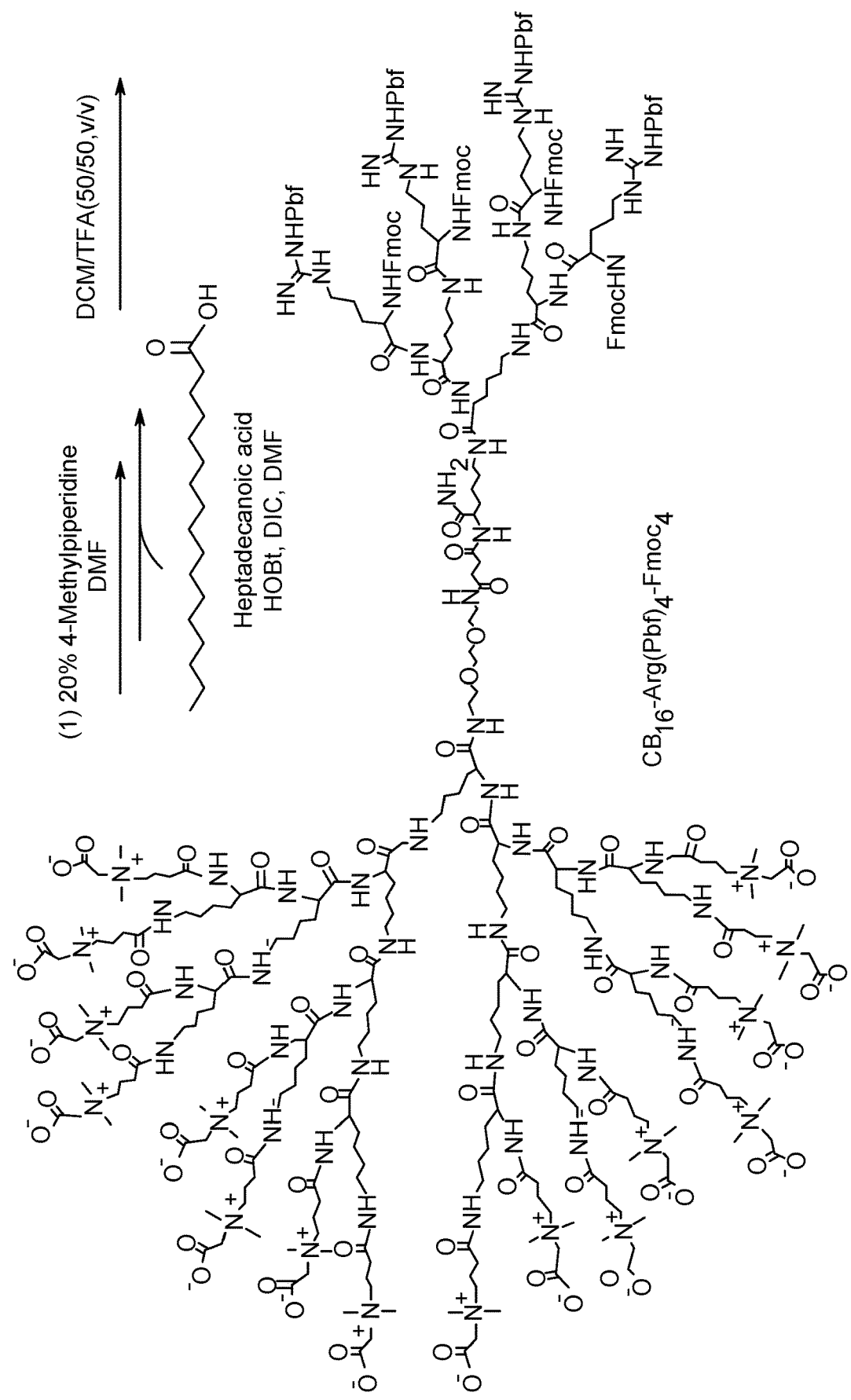
Figure 10:
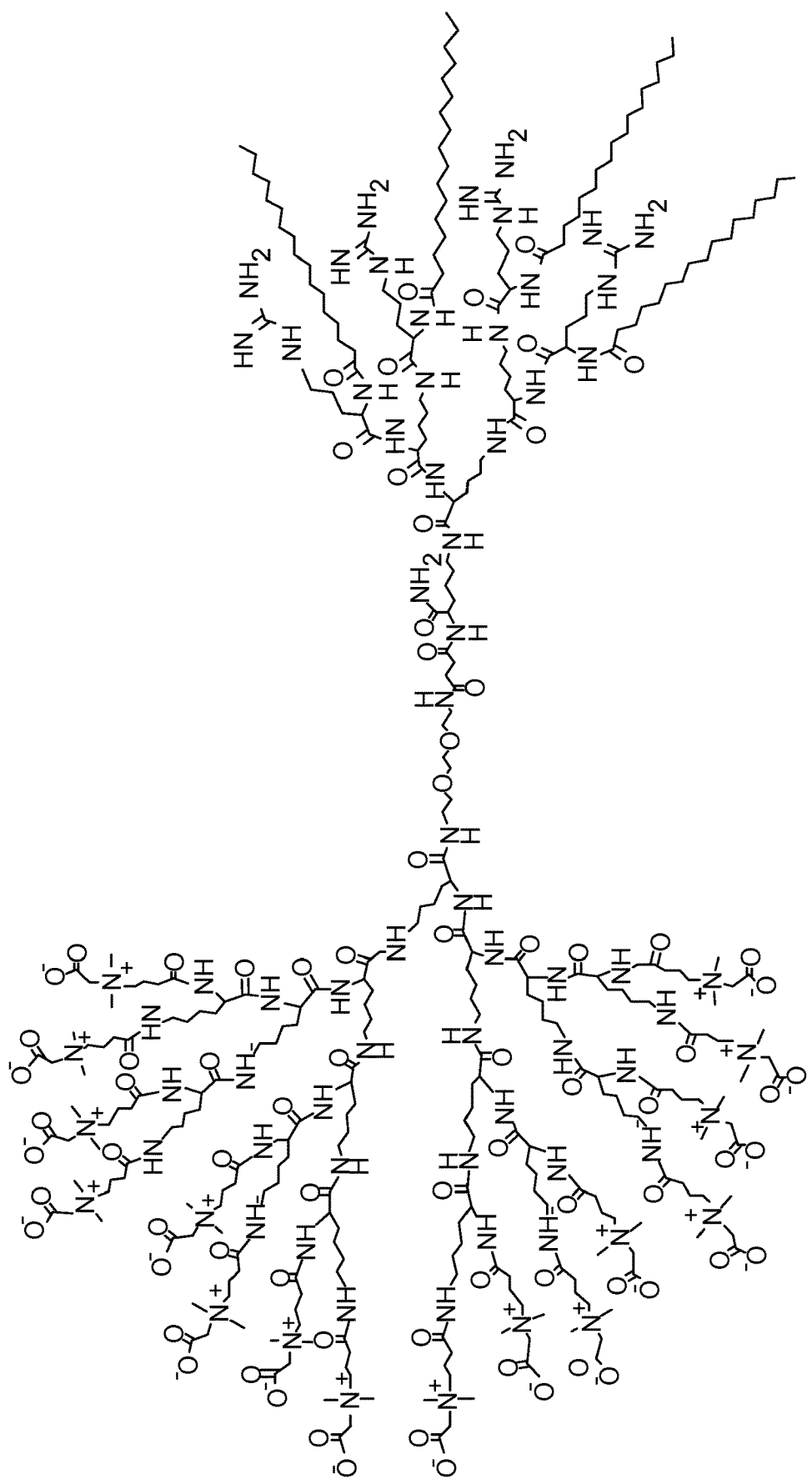
Figure 11A:
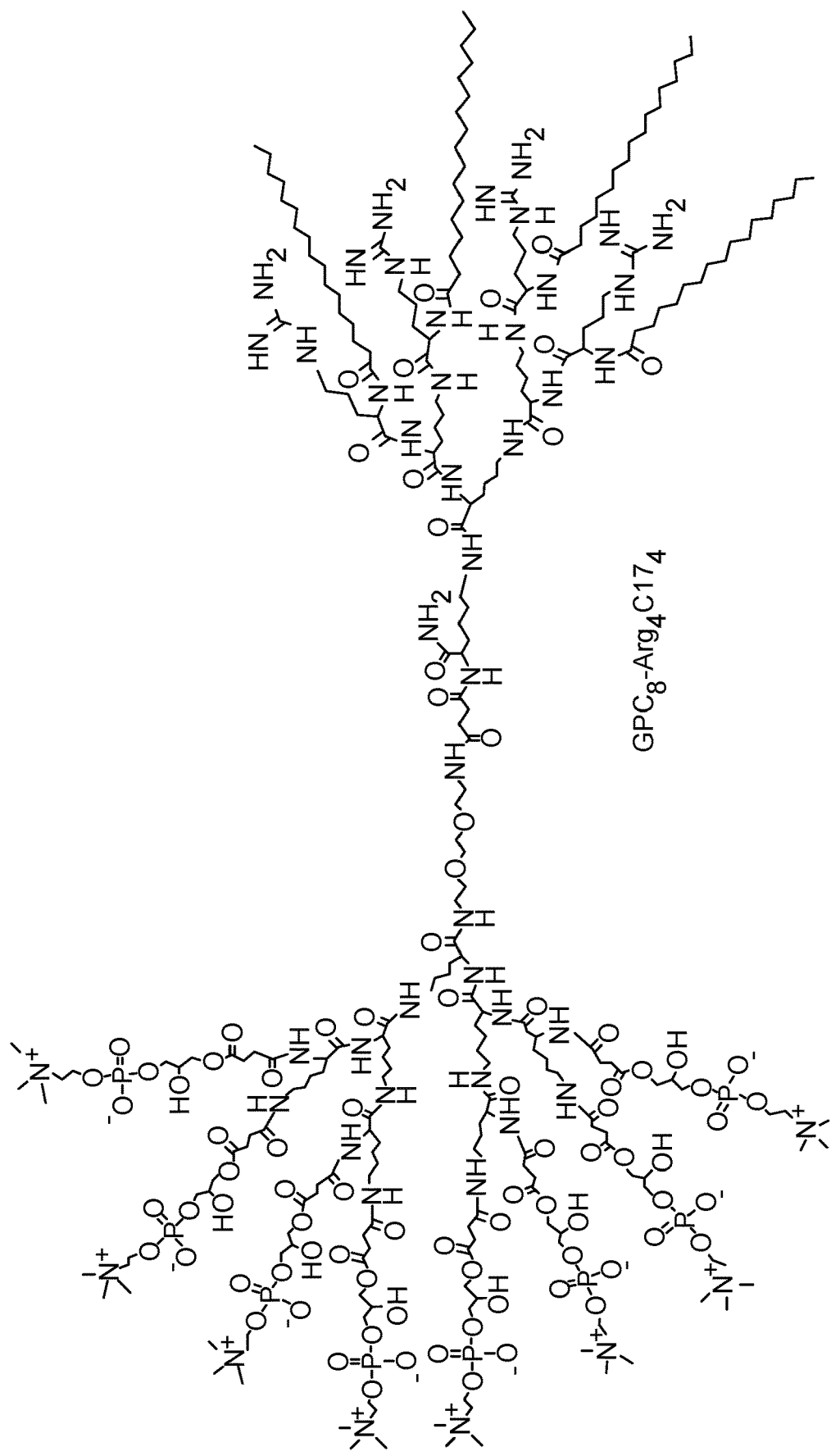
FIG. 11 shows examples of Janus-type zwitterionic amphiphilies for protein and drug binding.
Figure 11A:
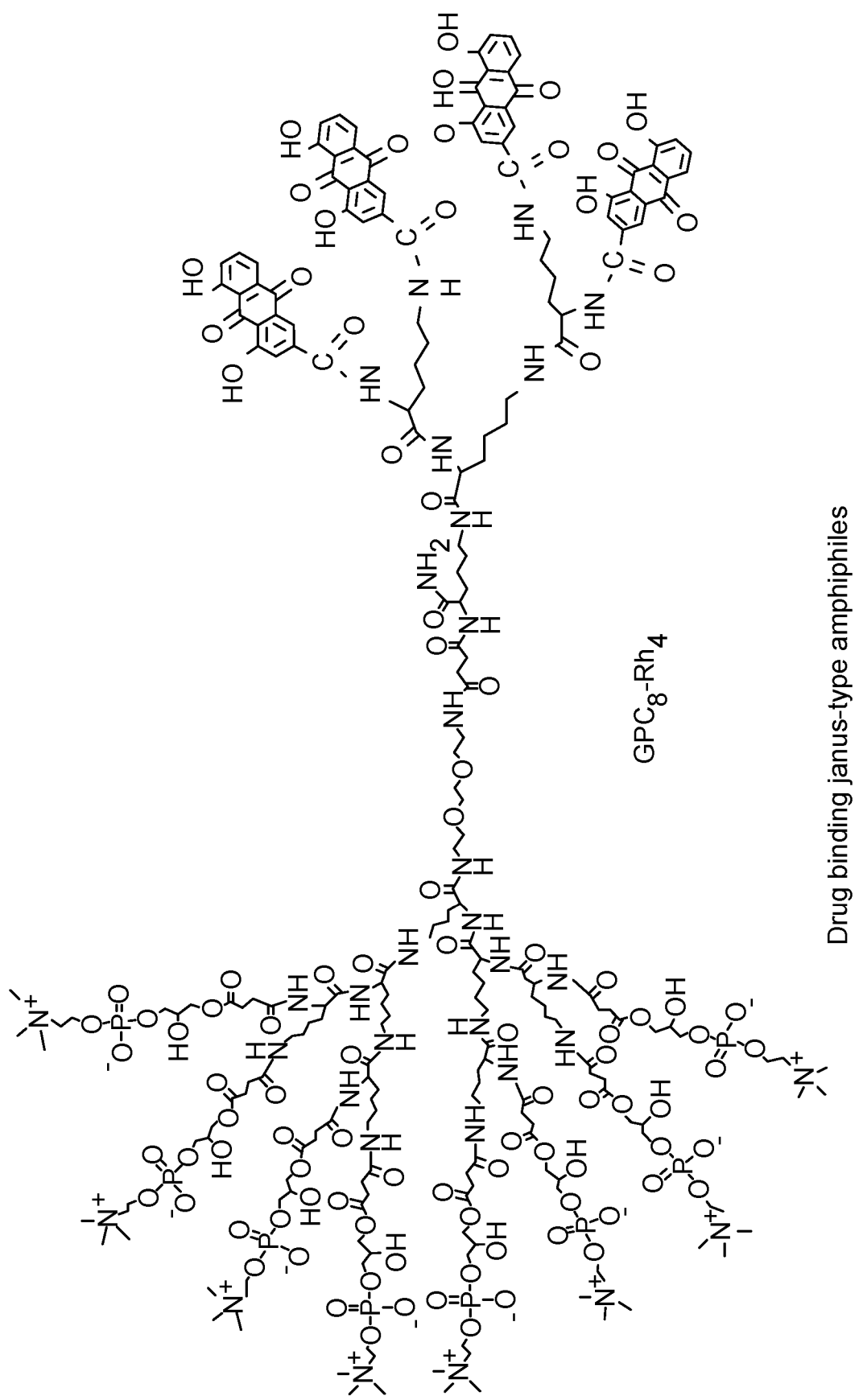
Figure 11A:
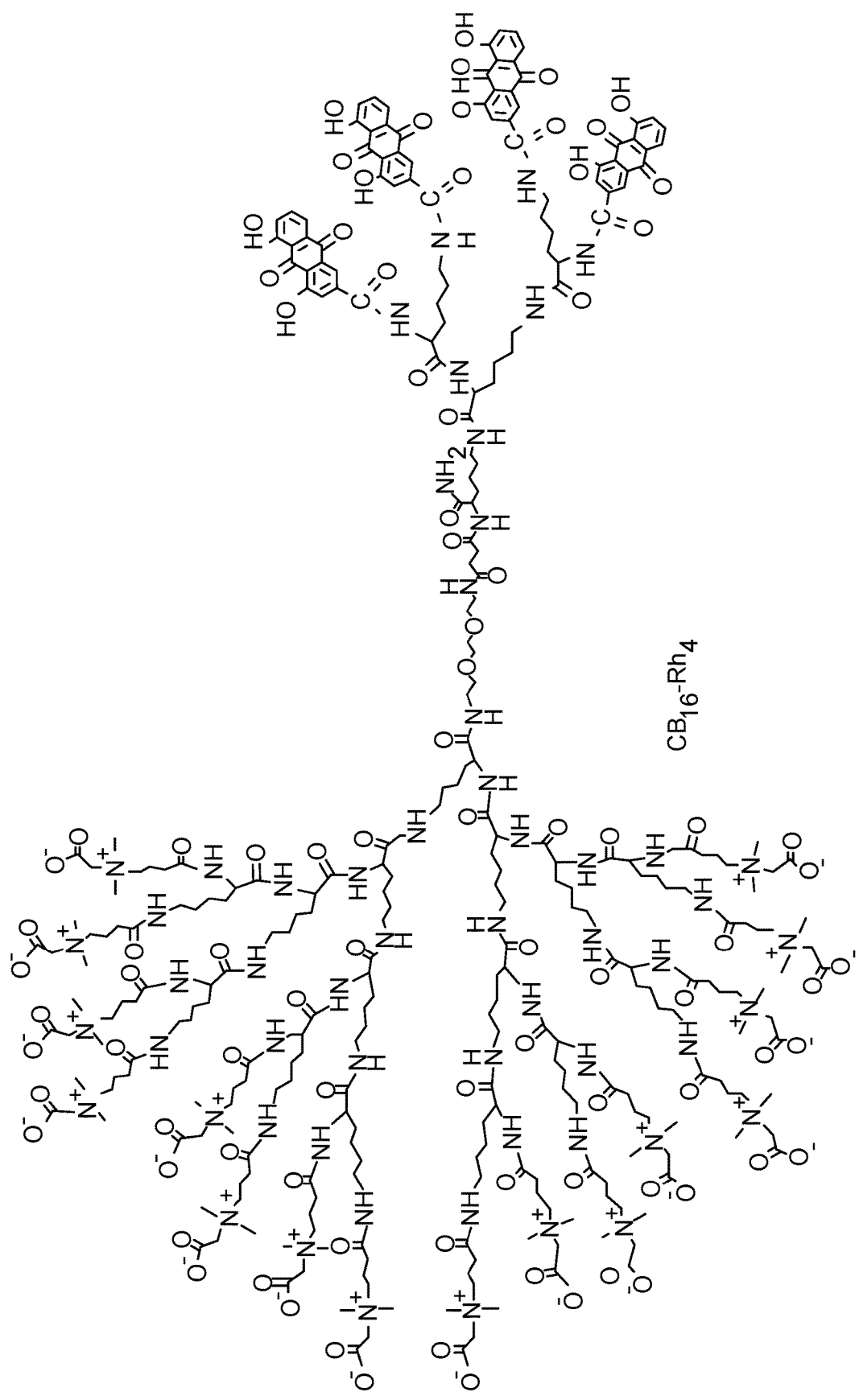
Figure 11B:
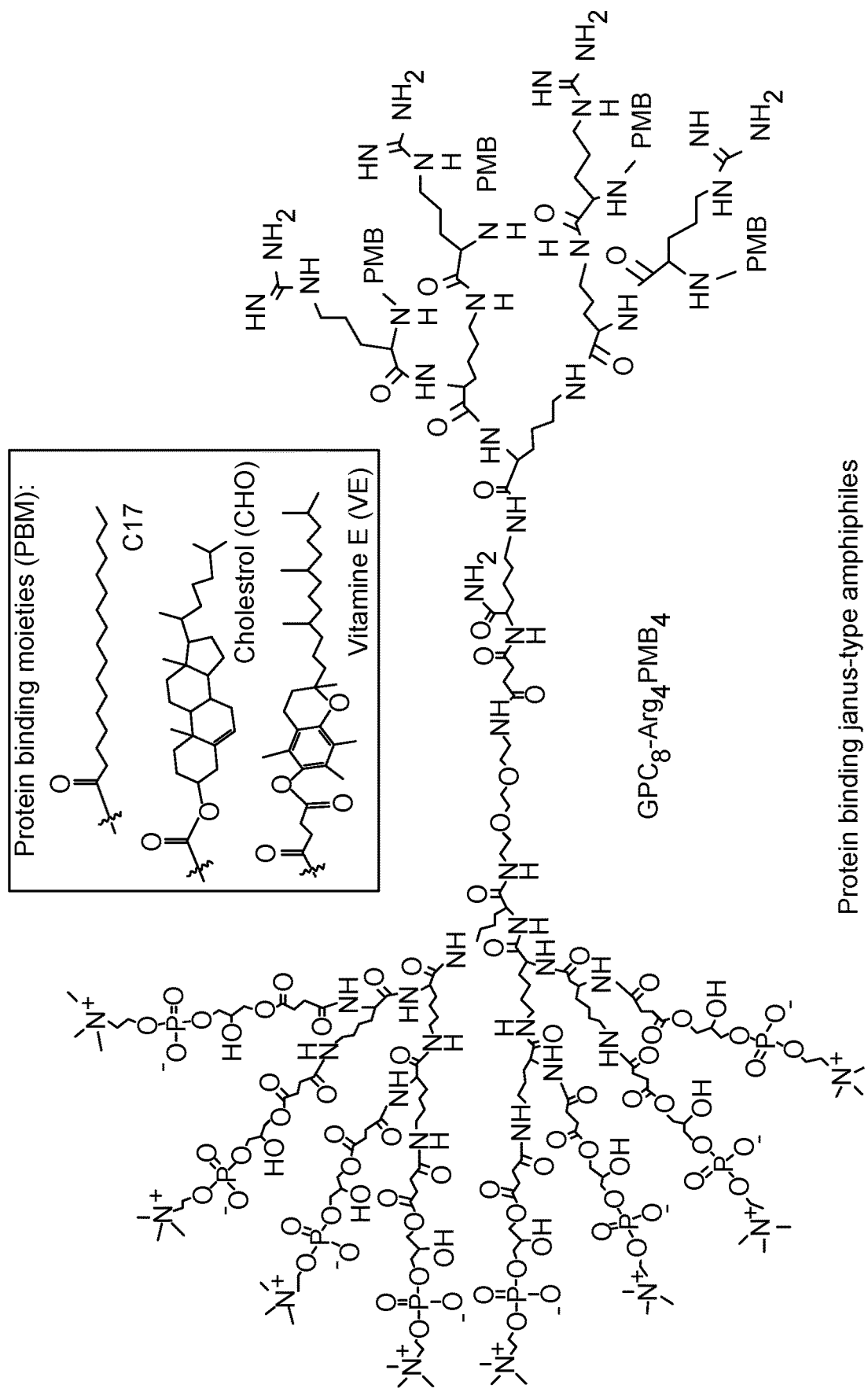
Figure 11B:
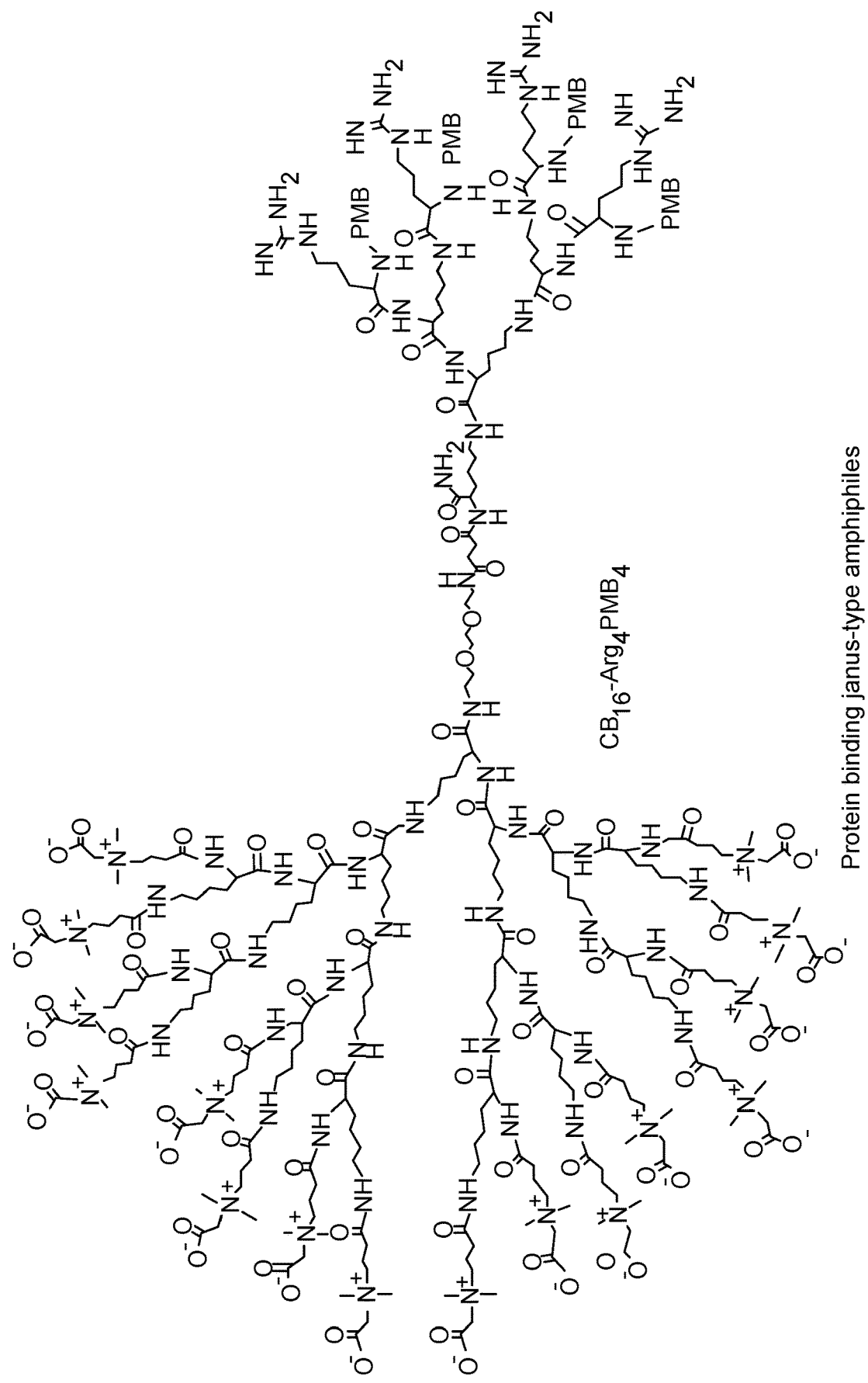
Figure 11B:
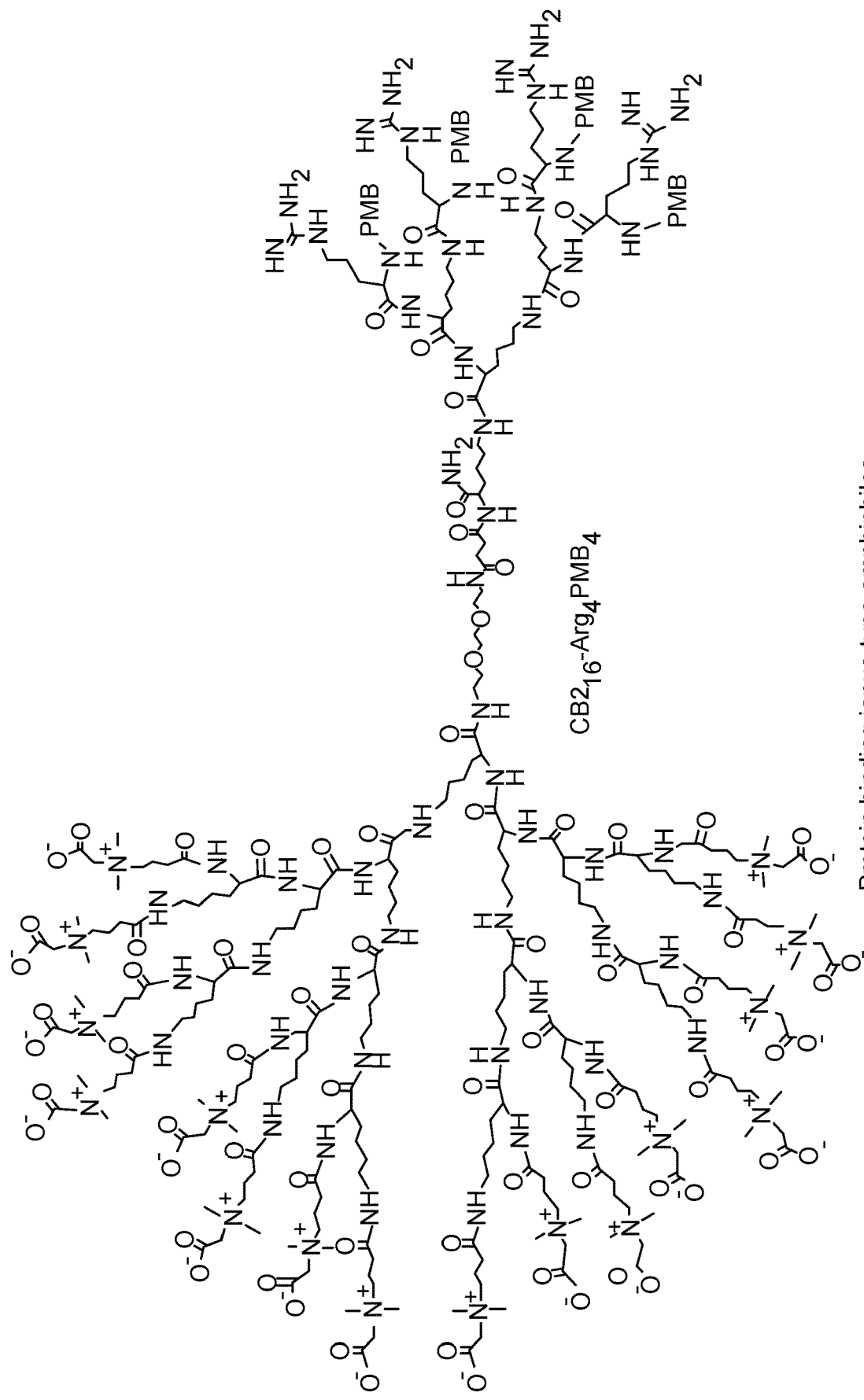
Figure 11C:
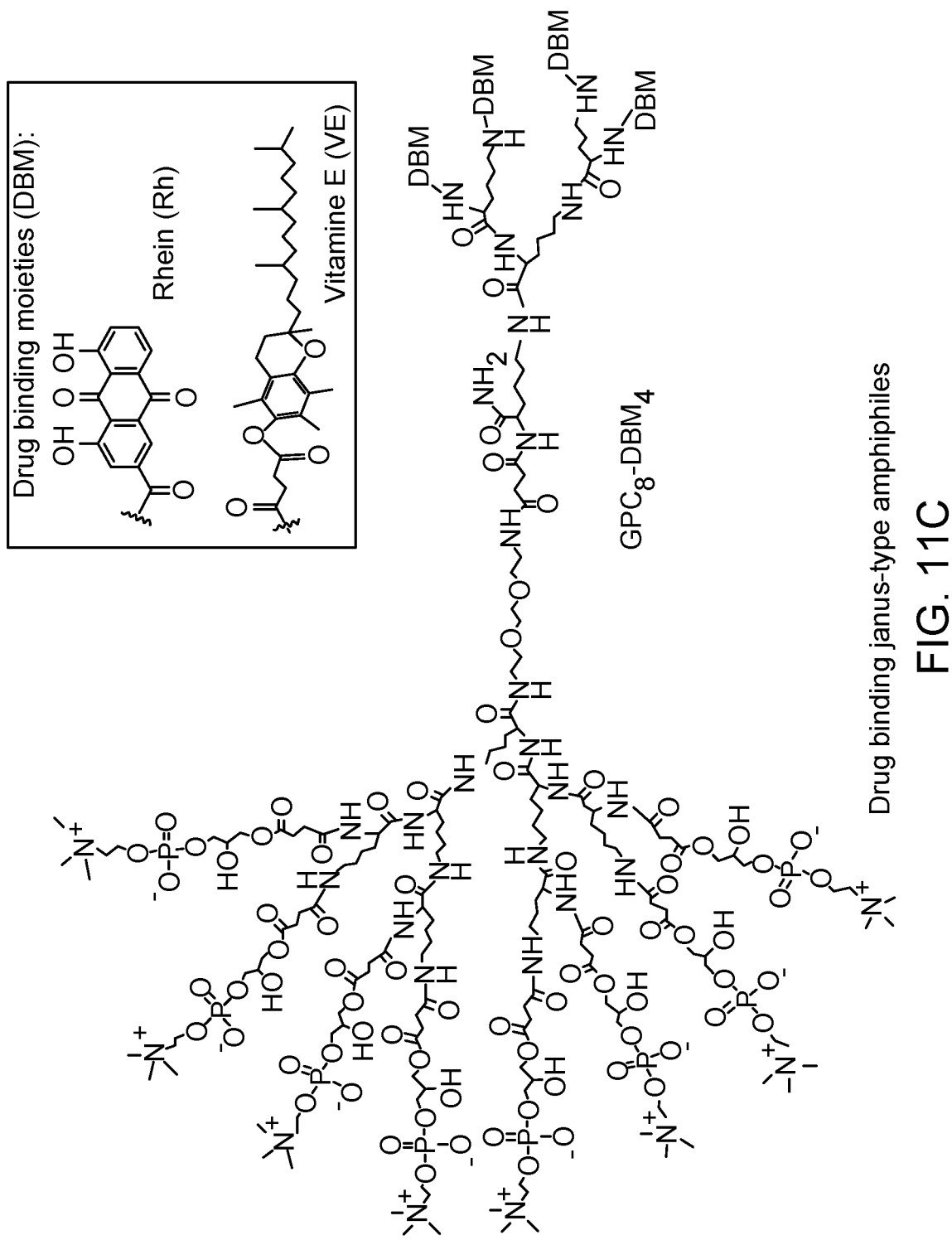
Figure 11C:
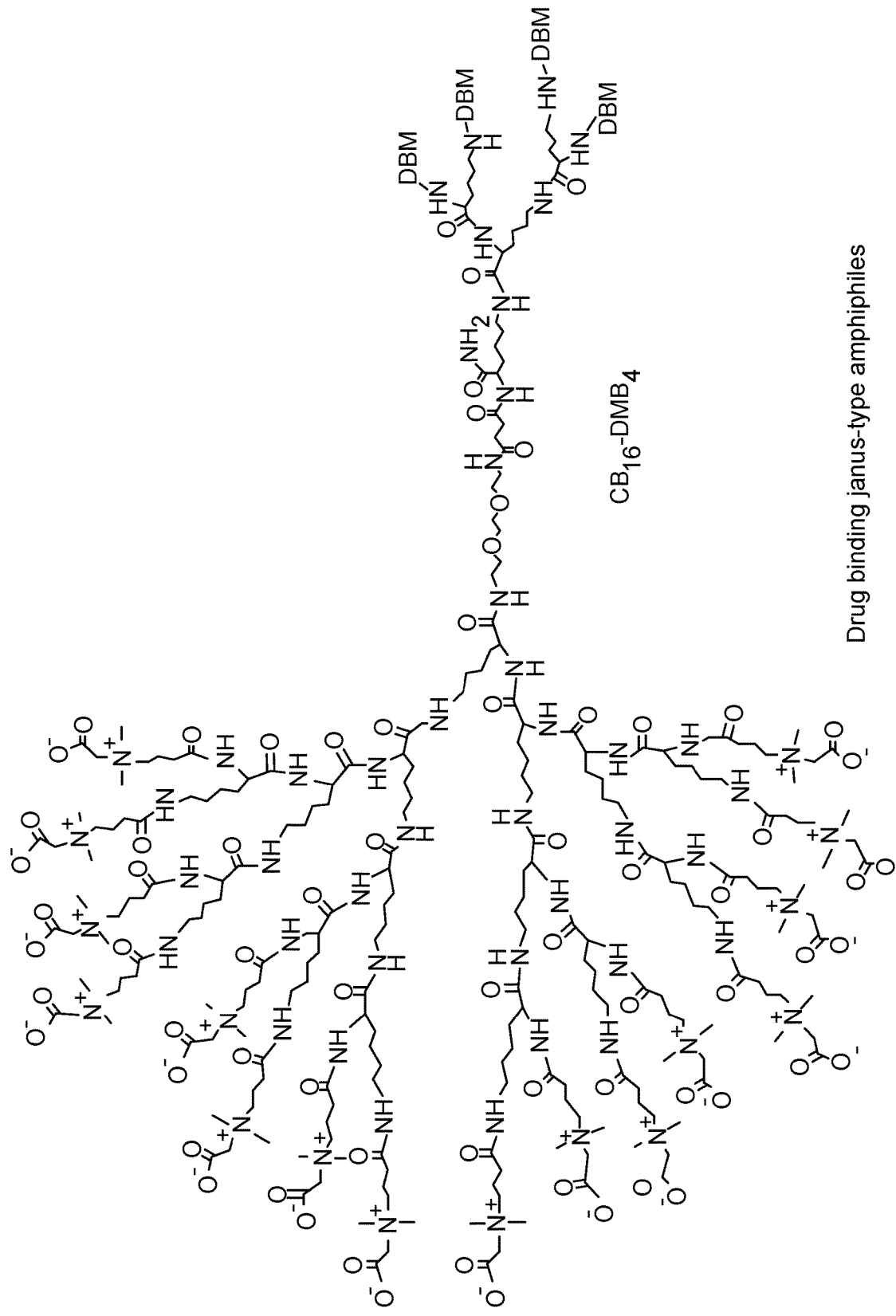
Figure 11C:
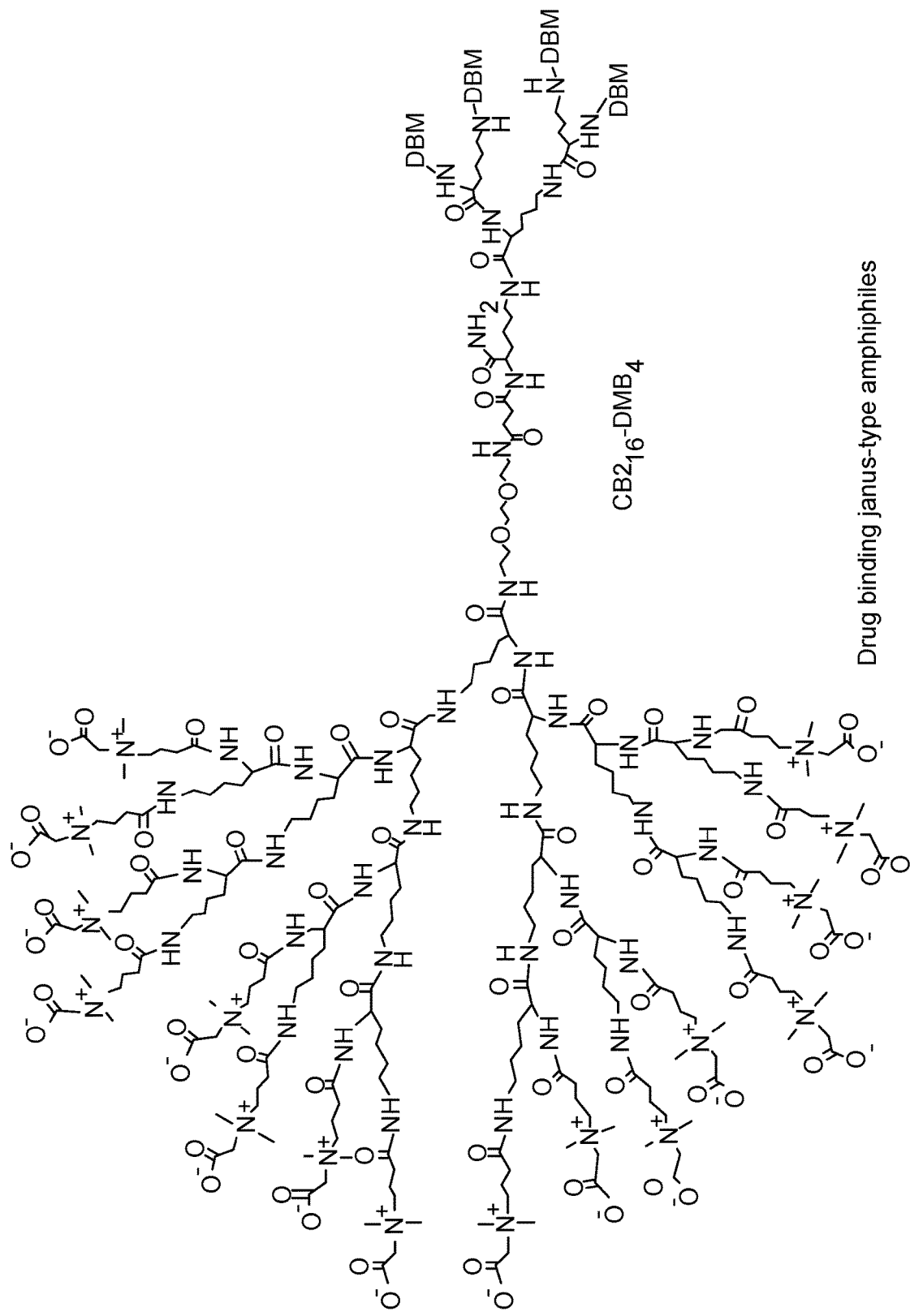

Synthesis of zwitterionic polylysine dendrons and Janus-type dendritic polymers. Solid-phase peptide synthesis (SPPS) was utilized to generate dendrons with zwitterionic peripheries in a divergent approach using amide linker as a backbone. A stepwise synthetic pathway is shown in FIGS. 9 and 10. Starting from rink amid resin, Boc-protected lysine (Fmoc-Lys(Boc)-OH) was initially conjugated and remain as the protected functional group throughout the SPPS. Subsequently, Fmoc-Lys(Fmoc)-OH serves as AB2 monomer for high yielding polylysine dendron growth utilizing interactive amide formation and deprotection chemistry. The deprotection step was carried out by the treatment of 20% 4-methylpiperidine in DMF. Site-specific modifications of dendrons with zwitterionic moieties were conducted at the peripheries of polylysine dendrons. Carboxybetain (CB) and glycerylphosphorylcholine (GPC) were the two choices of zwitterionic moieties for dendron functionalization (dendrons were denoted as D-$CB_n$ and D-$GPC_n$ respectively, where n indicates the numbers of periphery functional groups). GPC was converted carboxylic acid functional group by reacting to succinic anhydride. The cleavage of zwitterionic dendron from the rink resin offers reactive free amine at focal point to initiate the asymmetric dendrimers growth via liquid-phase peptide synthesis (LPPS). The chemical compositions of zwitterionic dendrons were elucidated by $^1$H NMR analysis. As shown in FIG. 1A, signal integration values indicated near quantitative synthesis of the zwitterionic dendron by comparing the N-methyl protons of the CB (d, 2.68 ppm) and the methylene units of the oligo-ethylene glycol (8-13, 3.18-3.80 ppm). Similarly, well-defined structure of D-$GPC_8$—$NH_2$ was highlighted by $^1$H NMR (recorded in $D_2O$, FIG. 1B), showing the quantitative number methyl proton (1, 3.29 ppm) on quaternary nitrogen relative to methylene protons (e.g., 13, 3.04 ppm).

The dendrons with multiple zwitterionic moieties possessing charge pair are less likely to facilitate the electron attachment for ionization in MALDI-TOF measurement. Therefore, the absolute molecular weight of D-$DMBA_{16}$-$NH_2$ was analyzed instead, exhibiting the sodium adduct $[M+Na]^+$ at m/z 4130.894. The obtained zwitterionic dendrons are well soluble in water and a range of polar organic solvent including methanol, DMSO and DMF, which greatly benefit the further synthesis performed via LPPS.

Figure 3:
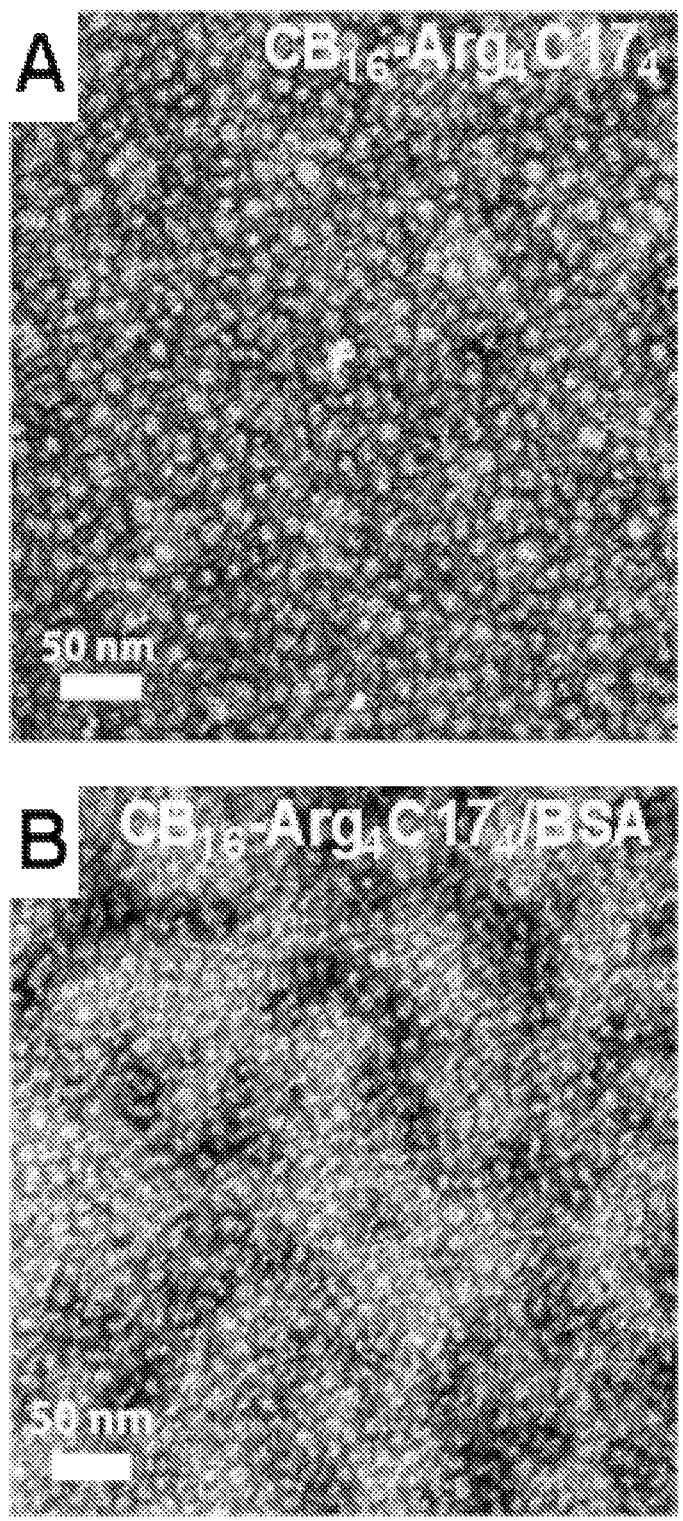
FIG. 3 shows hydrodynamic sizes of zwitterionic amphiphiles and their protein assemblies. Representative TEM images of (A) $CB_{16}$-$Arg_4C17_4$ and (B) BSA loaded $CB_{16}$-$Arg_4C17_4$ nanoparticle.

Self-assembly characterization of zwitterionic nanocarrier. The size, morphology, hydrodynamic diameter, and polydispersity of nanoparticles formed by zwitterionic amphiphiles were measured using TEM and DLS. The possession of both therapeutic binding moieties and zwitterionic functionalities confer Janus-type polymers with amphiphilic property, enabling their spontaneous self-assembly in aqueous solutions into nanoparticles. TEM and DLS results show that $CB_{16}$-$Arg_4C17_4$ forms spherical micelles with a size of 9.7±2.5 nm and BSA loaded $CB_{16}$-$Arg_4VE_4$ maintained the size and morphology (FIG. 3 and Table 1).

TABLE 1

Physicochemical properties of zwitterionic amphiphiles.

| Polymer | Molecular weight (theo.) Da | Hydrodynamic size ($D_h$) (nm) | $D_h$ with DOX loading (nm) | $D_h$ with BSA loading | $^a$DLE % |
| --- | --- | --- | --- | --- | --- |
| $CB_{16}$-$Arg_4C17_4$ | 7056.15 | 8.1 ± 2.1 | NA | 11.0 ± 3.8 | NA |
| $CB_{16}$-$Rh_4$ | 6473.41 | 42.5 ± 12.5 | 13.3 ± 3.7 | NA | 98% |
| $GPC_8$-$Arg_4C17_4$ | 6003.46 | 9.2 ± 2.4 | NA | 11.3 ± 3.3 | NA |
| $GPC_8$-$Rh_4$ | 5434.16 | 34.7 ± 12.5 | 25.6 ± 7.6 | NA | 99% |

$^a$DLE was measured by fluorescence analysis at a drug loading content (DLC) of 10%.

Figure 4:
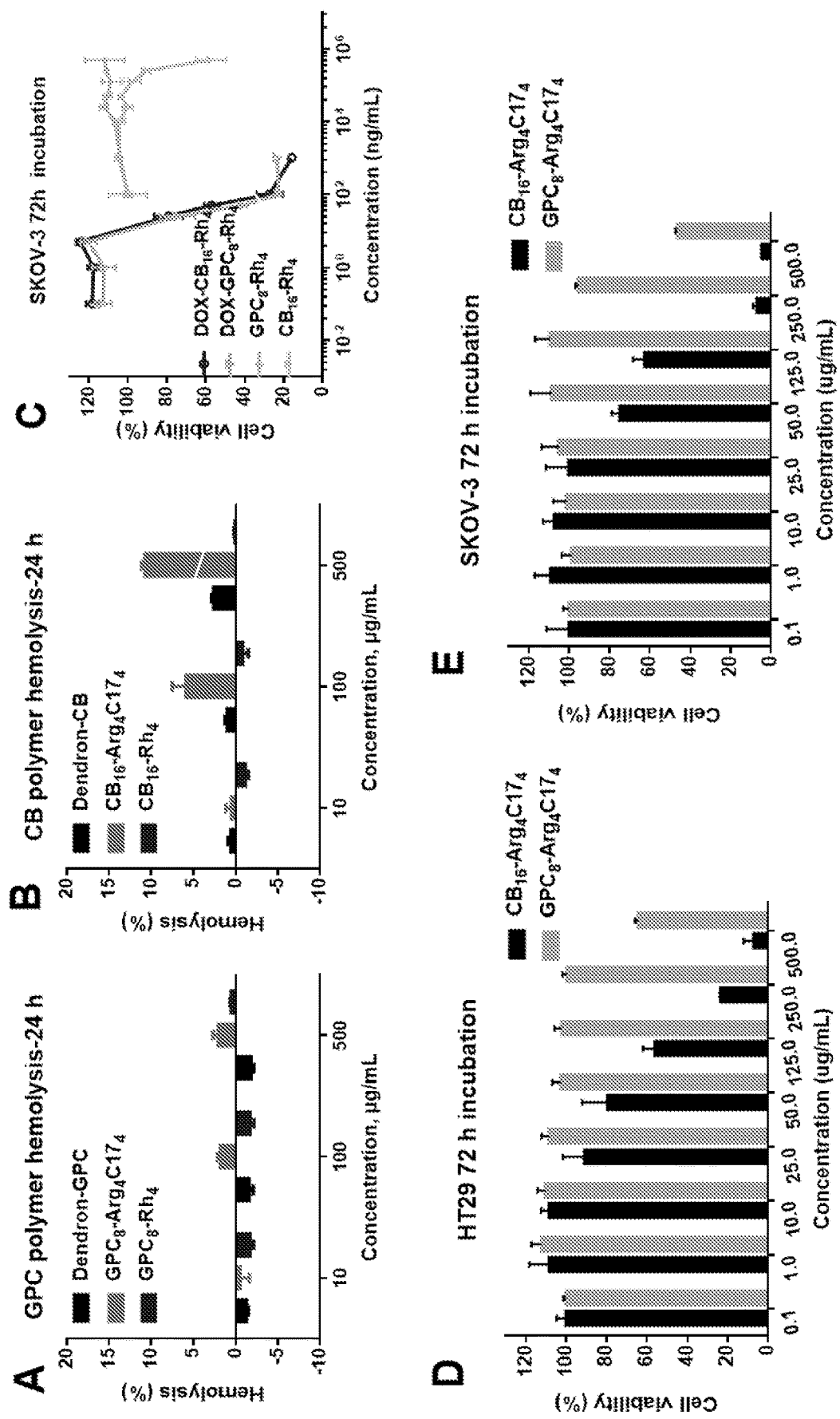
FIG. 4 shows in vitro hemolytic activities and cytotoxicity of zwitterionic polymers towards red blood cells after 24 h (h=hours) incubation at different concentrations. (A) GPC polymer (Dendron-GPC, $GPC_8$-$Arg_4C17_4$, and $GPC_8$-$Rh_4$) hemolysis after 24 h; and (B) CB polymer (Dendron-CB, $CB_{16}$-$Arg_4C17_4$, $CB_{16}$-$Rh_4$) hemolysis after 24 h) at 37° C.; in vitro cytotoxicity of zwitterionic polymer against HT-29 and SKOV-3 cell lines measured by MTS assay. (C) SKOV-3 after 72 h incubation with DOX-$CB_{16}$—$Rh_4$, DOX-$GPC_8$-$Rh_4$, $GPC_8$-$Rh_4$ and $CB_{16}$—$Rh_4$; (D) HT-29 after 72 h incubation with $CB_{16}$-$Arg_4C17_4$ and $GPC_8$-$Arg_4C17_4$; (E) SKOV-3 after 72 h incubation with $CB_{16}$-$Arg_4C17_4$ and $GPC_8$-$Arg_4C17_4$.

The in vitro cytotoxicity of the obtained zwitterionic polylysine polymers was examined against HT29 and SKOV-3 cell lines by MTS assay. $GPC_8$-$Arg_4C17_4$ shows no cytotoxic effect up to a concentration of 250 μg/mL for 72 h incubation with both HT-29 and SKOV-3. More than 75% viable cells were detected after incubation with $CB_{16}$-$Arg_4C17_4$ up to a concentration of 50 μg/mL. Varying zwitterionic polymers and their corresponding functionalities was incubated with red blood cell in the range of 10-500 μg/mL for 24 h. Results in FIG. 4C show that $CB_{16}$-$Arg_4C17_4$ caused up to 12% hemolysis at concentration of 500 μg/mL. Zwitterionic amphiphiles with GPC surface are demonstrated to be more haemocompatible, indicating no significant disturbance of the red blood cell membranes. The GPC surface as a mimic of extracellular surfaces of the lipid bilayer is expected to be more biocompatible in addition to the zwitterionic property.

Zwitterionic amphiphiles-protein interactions. Protein absorption resistance of polymer surface by BLI study. The protein adsorption reduction of the zwitterionic polymers was investigated by BLI study using BSA as a serum protein mimic. Amine reactive (AR) sensor tips were activated by EDC/NHS and immobilized with PEG-$NH_2$ (Mw=~5 kDa), D-$CB_{16}$—$NH_2$ and D-$GPC_8$—$NH_2$ in solution. Real-time immobilizations of the polymers were monitored by the surface thickness changes using Fortebio software. Polymer functionalized sensor tips were then exposed to BSA for adsorption behavior studies. Sensor tips functionalized by PEG, CB and GPC polymers show BSA depositions with 0.071, 0.026, and 0.015 nm changes in film thickness, respectively, while sensor without polymer functionalization showed a 0.117 nm change in thickness from BSA adsorption. The BLI study indicates that the both CB and GPC functionalized sensor tips exhibit higher resistance to non-specific protein adsorption than PEG.

Figure 5:
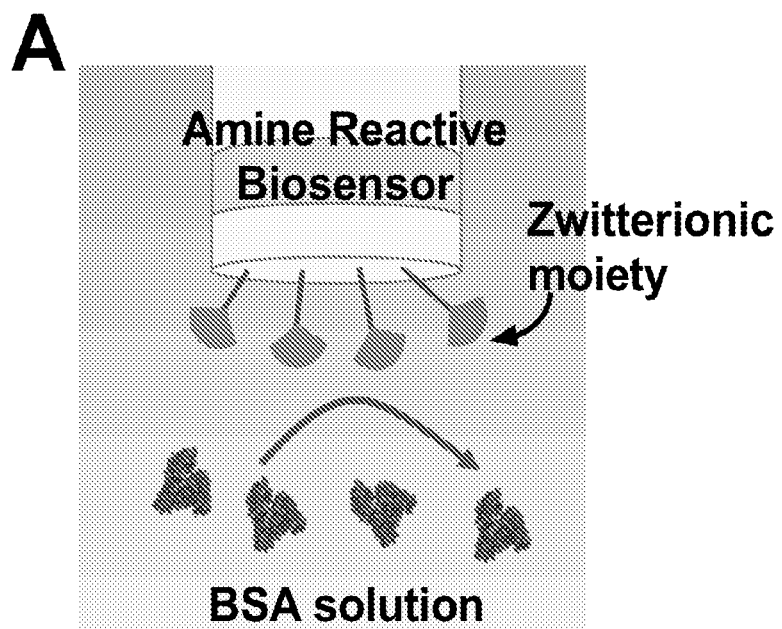
FIG. 5 shows (A) schematic illustration of the BSA adsorption on polymer immobilized amine reactive biosensor. (B) BLI profiles for association of BSA on biosensors immobilized with $PEG^{5k}$-$NH_2$, D-$CB_{16}$—$NH_2$ and D-$GPC_8$—$NH_2$ and the following dissociation in PBS.
Figure 5:
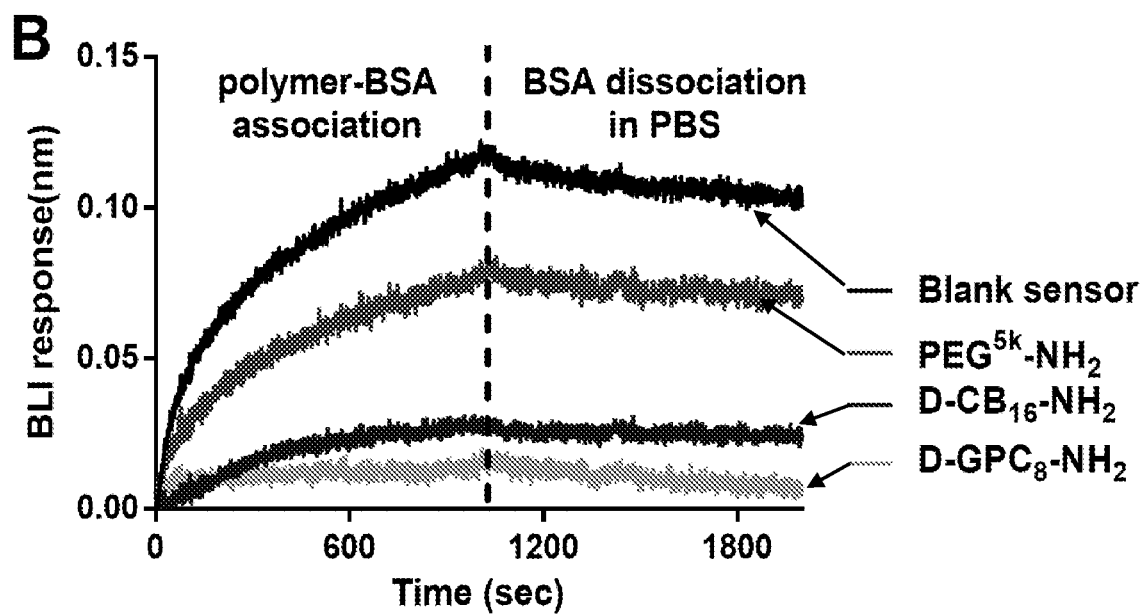
Figure 6:
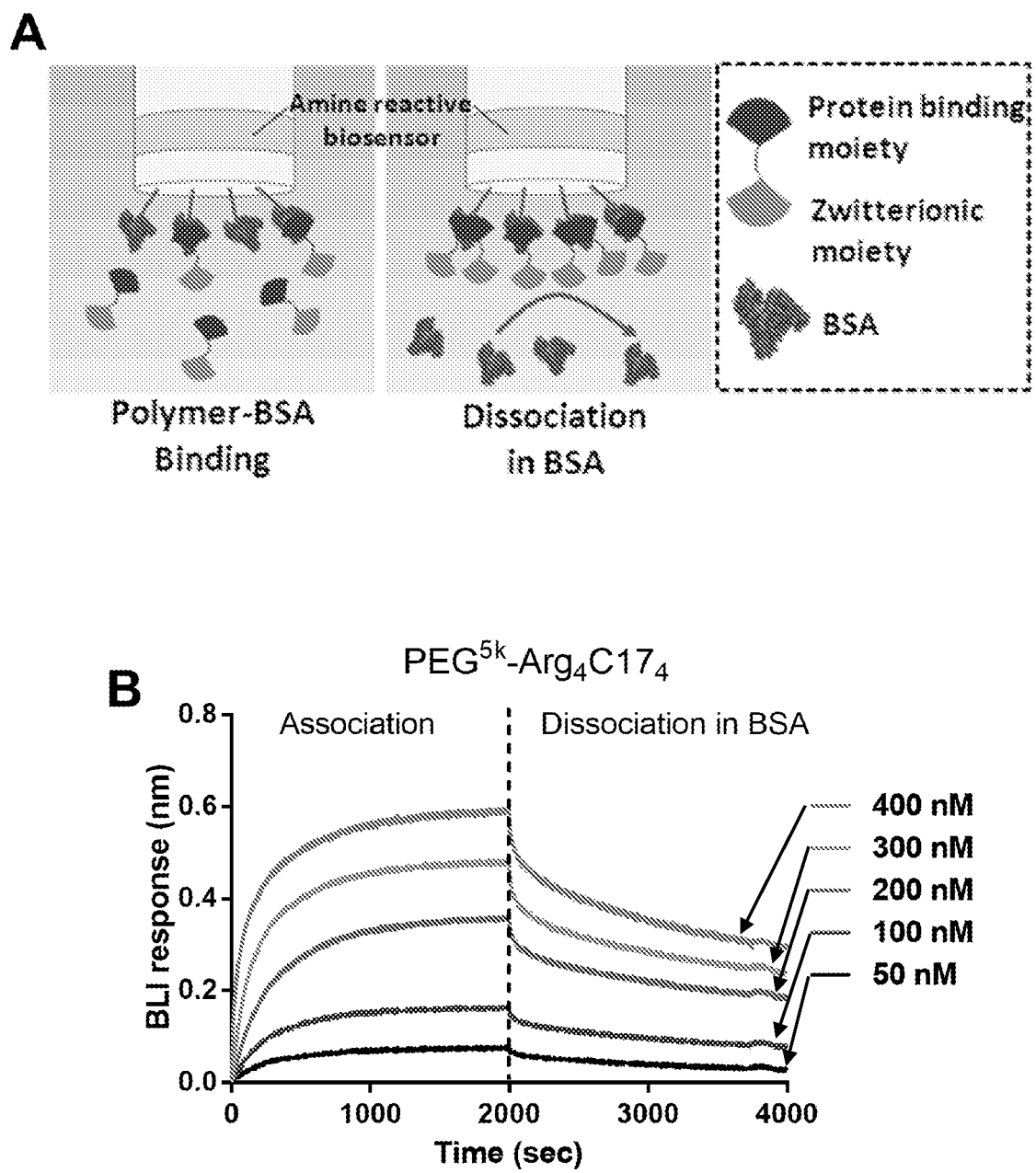
FIG. 6 shows (A) schematic illustration of the association in amphiphilic polymer solution (left) and dissociation in BSA solution (right) for the amine reactive biosensors immobilized with BSA. (B-D) BLI kinetics assays for association in $PEG^{5k}Arg_4C17_4$ (B), $CB_{16}$-$Arg_4C17_4$ (C), and $GPC_8$-$Arg_4C17_4$ (E) solutions in the range of 50-400 nM and dissociation in BSA solutions (5 mg/mL).
Figure 6:
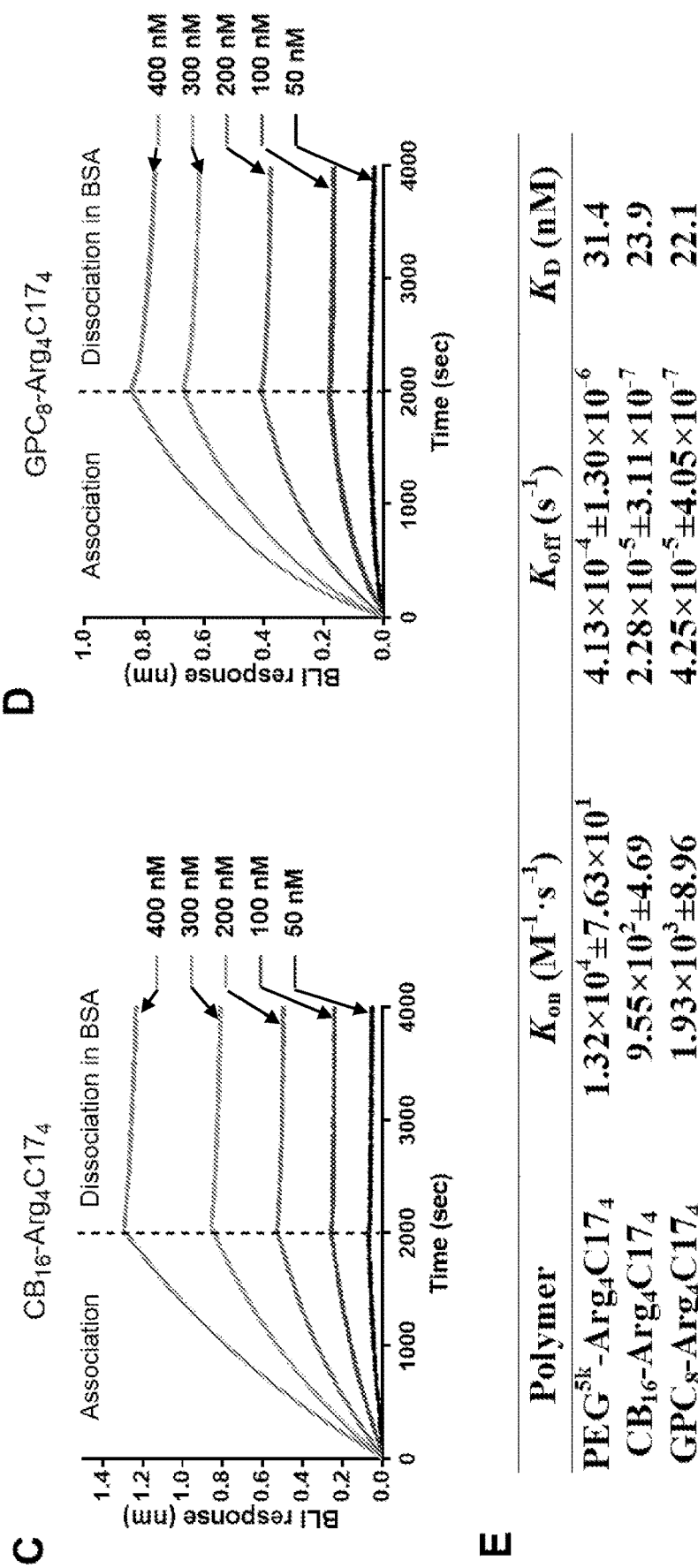
Figure 7:
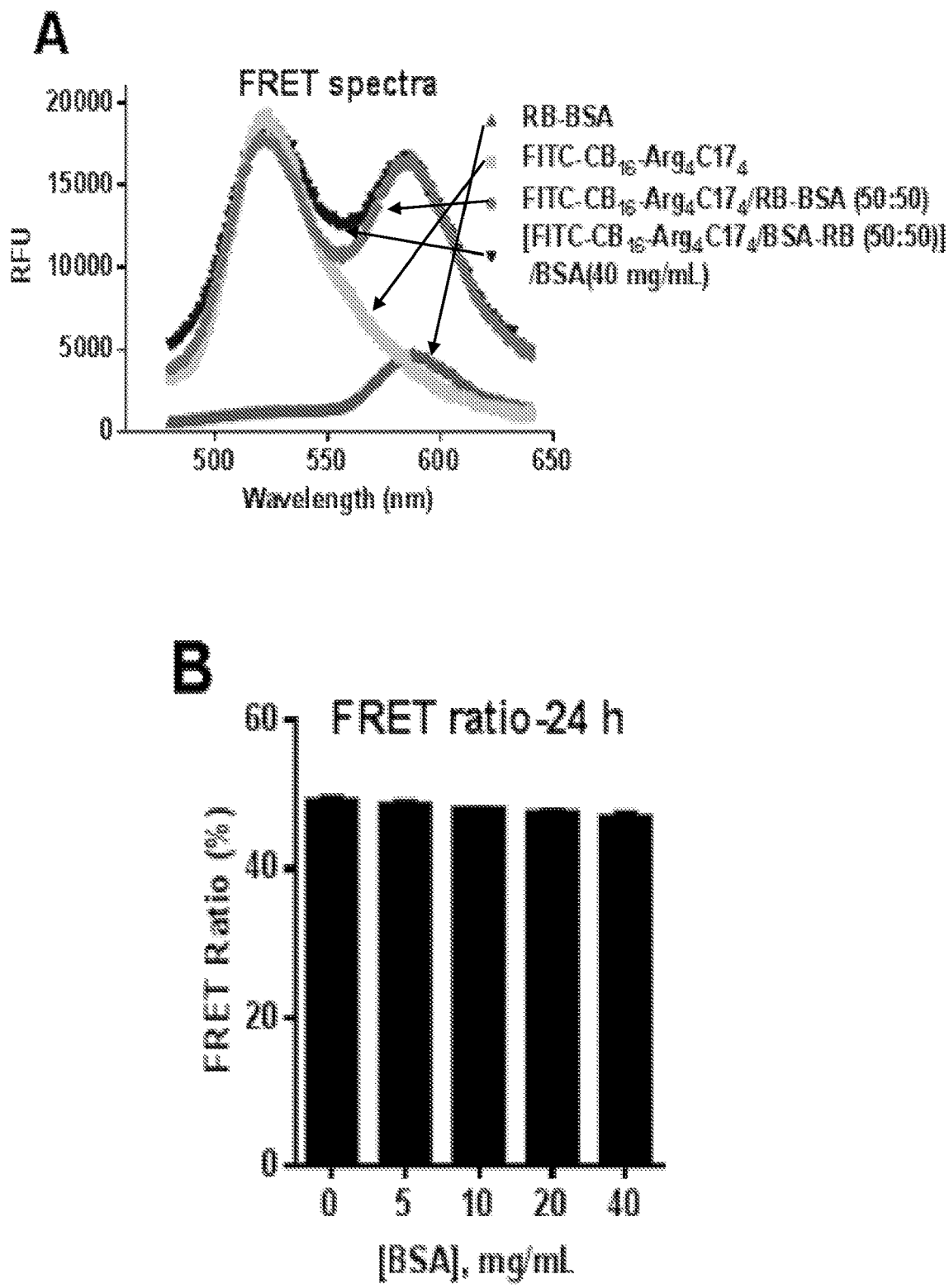
FIG. 7 shows protein loading studies of zwitterionic dendrimers with protein binding moieties using BSA as model protein. Fluorescence emission spectra of RB-BSA, FITC-$CB_{16}$-$Arg_4C17_4$ and their mixture (50:50) with and without external BSA at 40 mg/mL. Excitation λex=439 nm. (B) FRET ratios of 50/50 (w/w) mixtures of RB-BSA and FITC-FITC-$CB_{16}$-$Arg_4C17_4$ after incubation with BSA solutions at different concentrations. Loading capacity of protein binding zwitterionic polymers for FITC-BSA determined by an agarose gel retention assay. (C) Loading assay of $CB_{16}$-$Arg_4C17_4$; (D) Loading assay of $GPC_8$-$Arg_4C17_4$.
Figure 7:
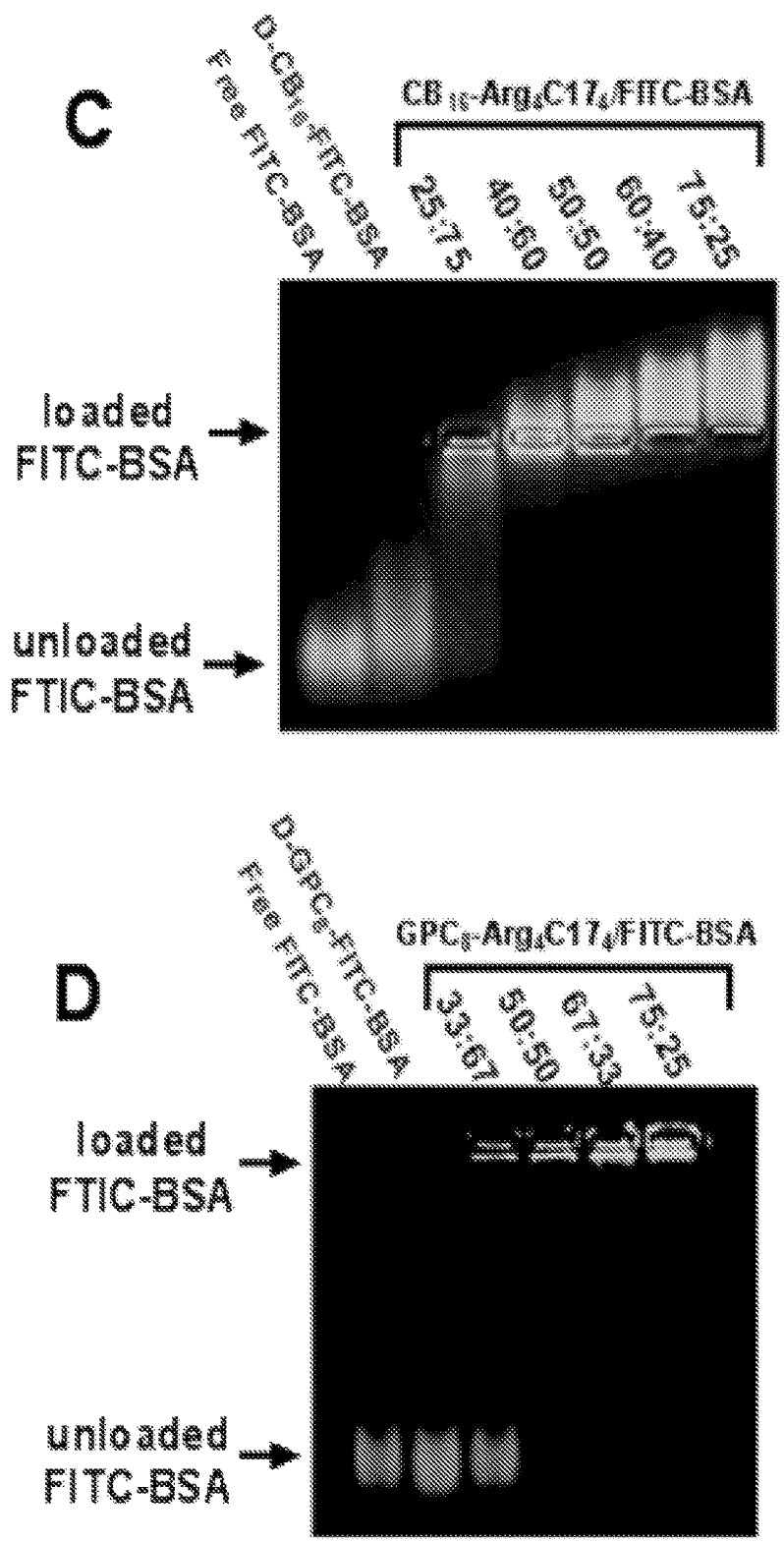
Figure 8:
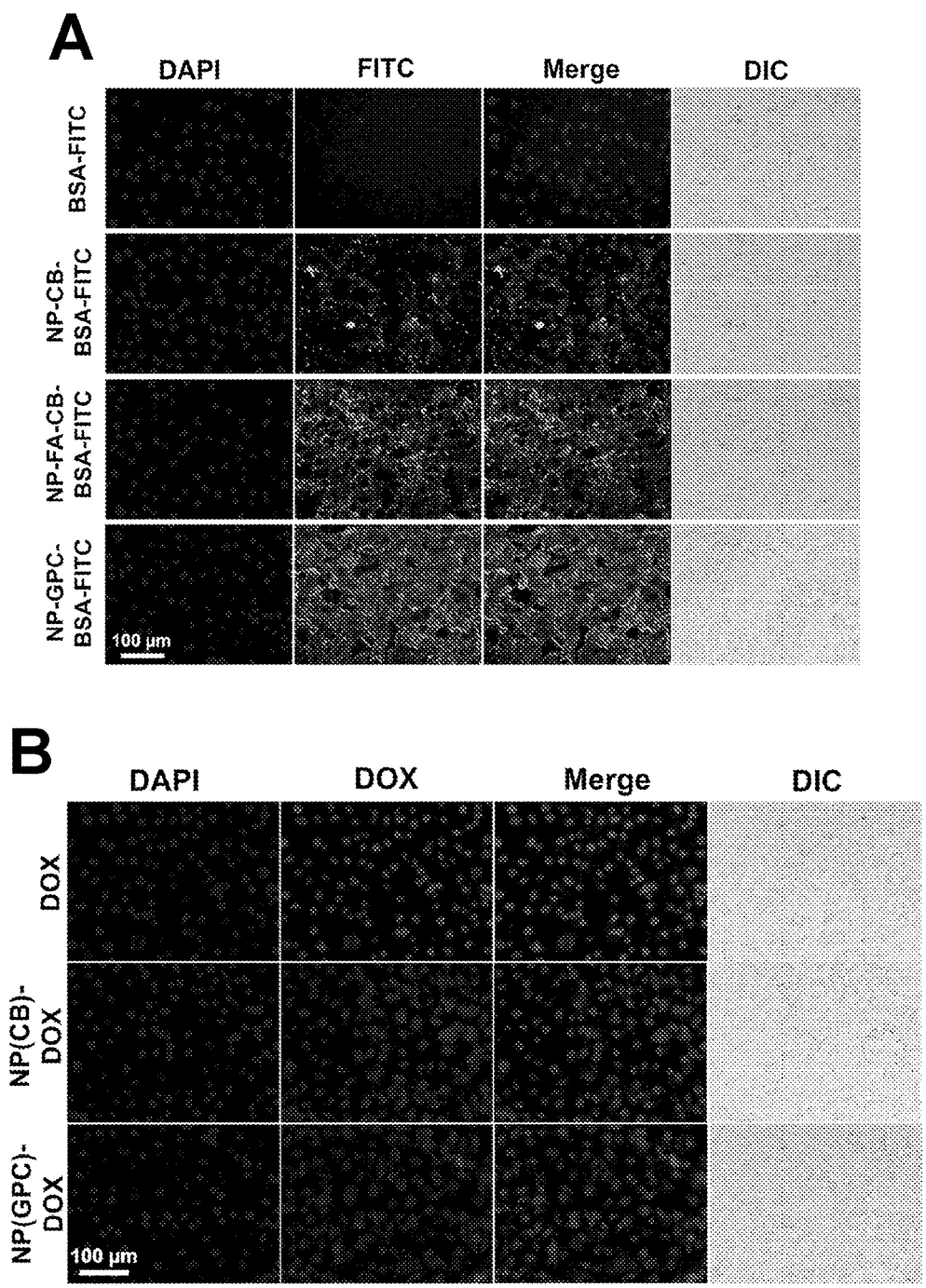
FIG. 8 shows (A) cellular uptake of FITC-BSA-loaded nanoparticles by SKOV-3 cells. (B) Cellular uptake of DOX-loaded nanoparticles by SKOVE-3 cells.
Figure 9A:
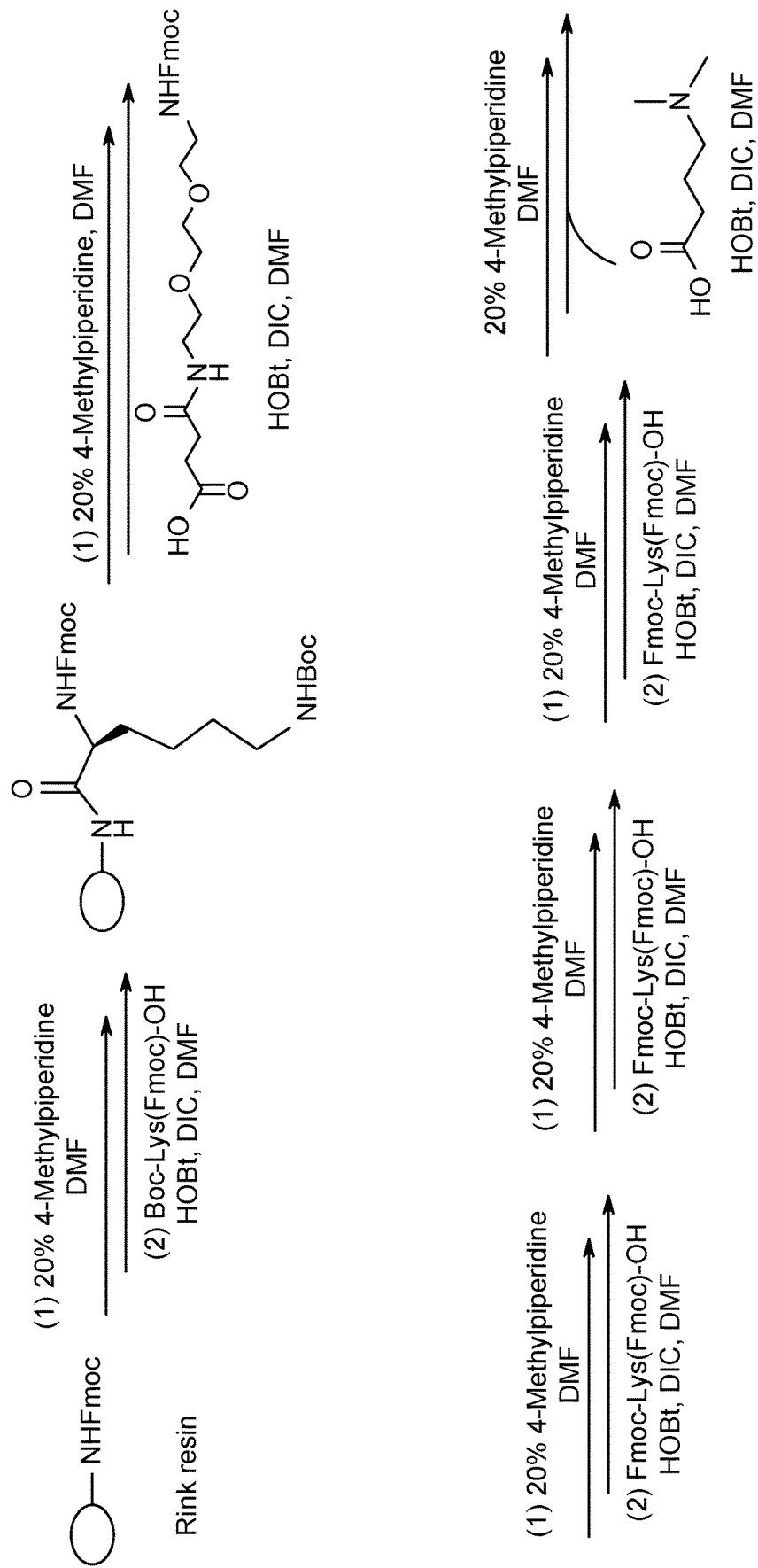
FIG. 9. Solid-peptide synthesis of zwitterionic dendrons. (A) Zwitterionic dendron (D-$CB_{16}$—$NH_2$) with carboxybetain (CB) moiety. (A) Zwitterionic dendron (D-$GPC_8$—$NH_2$) with glycerylphosphorylcholine (GPC) moiety.
Figure 9A:
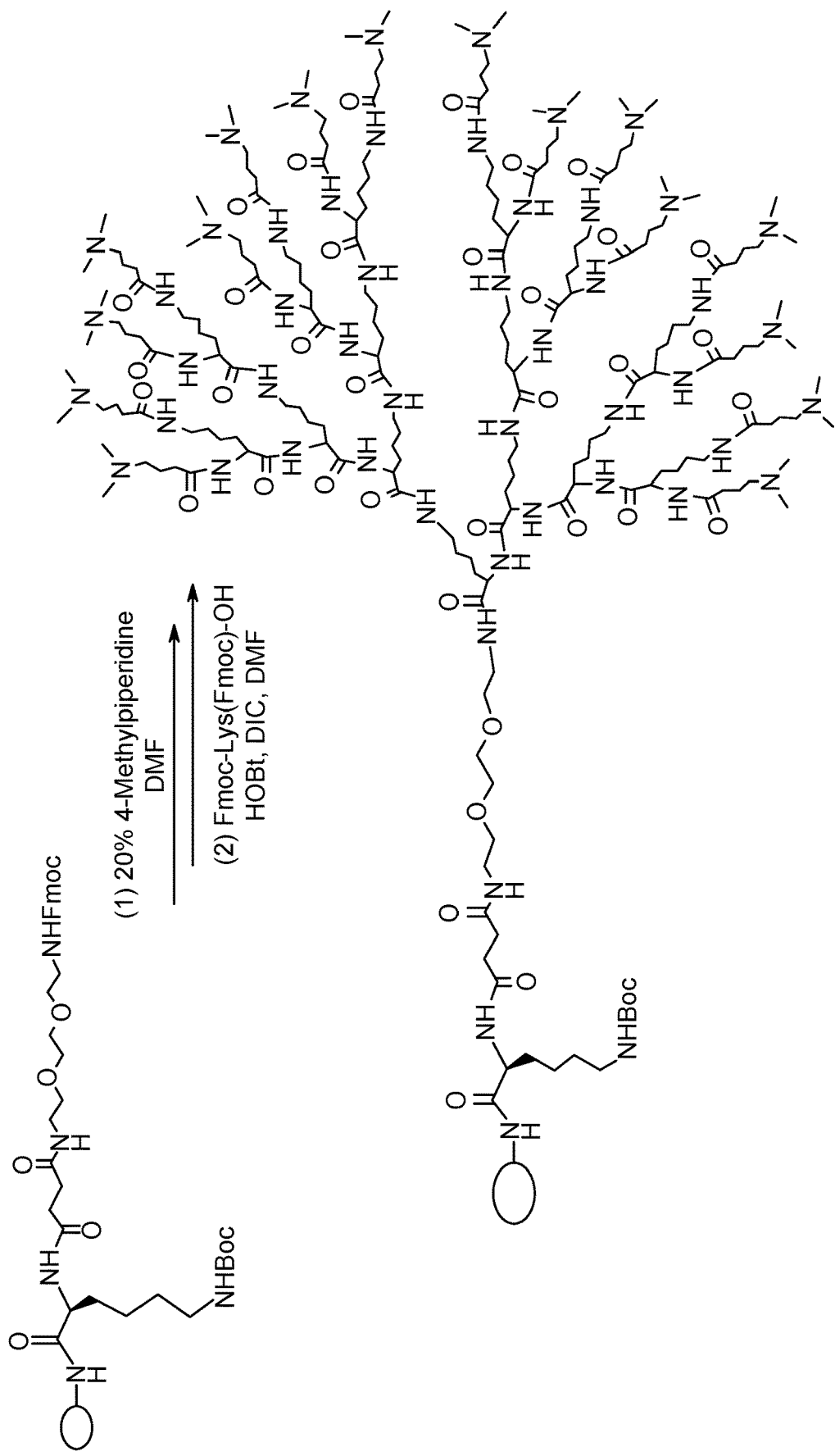
Figure 9A:
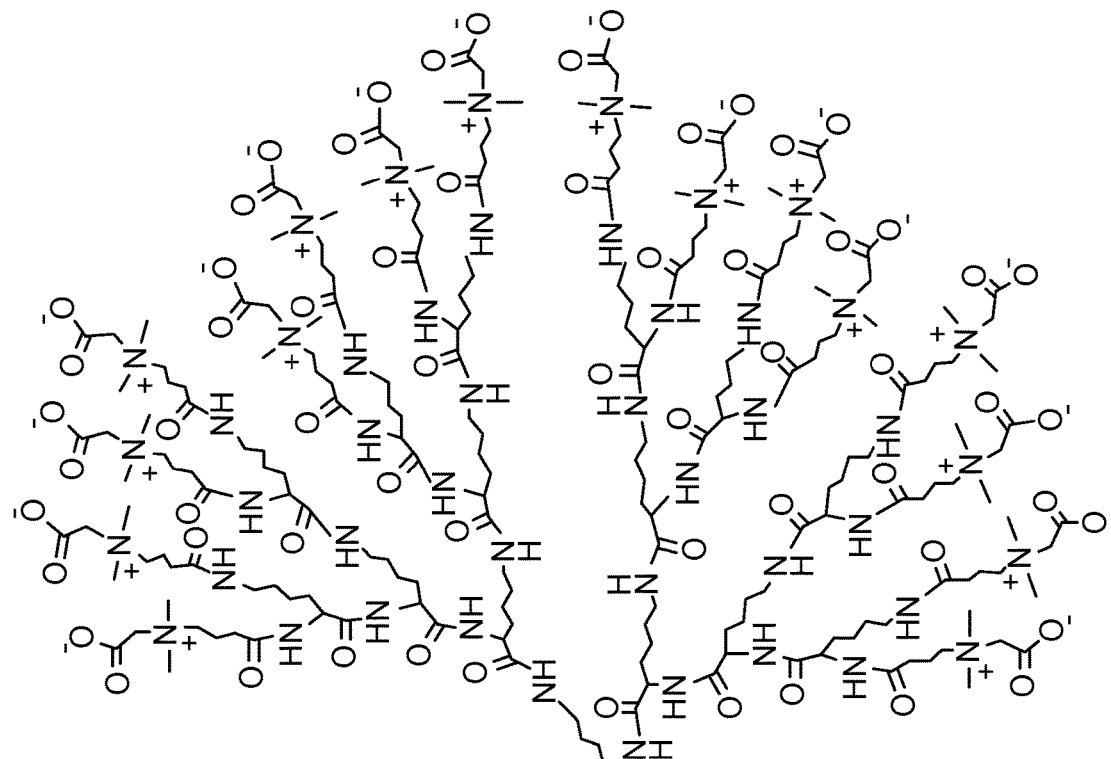
Figure 9B:
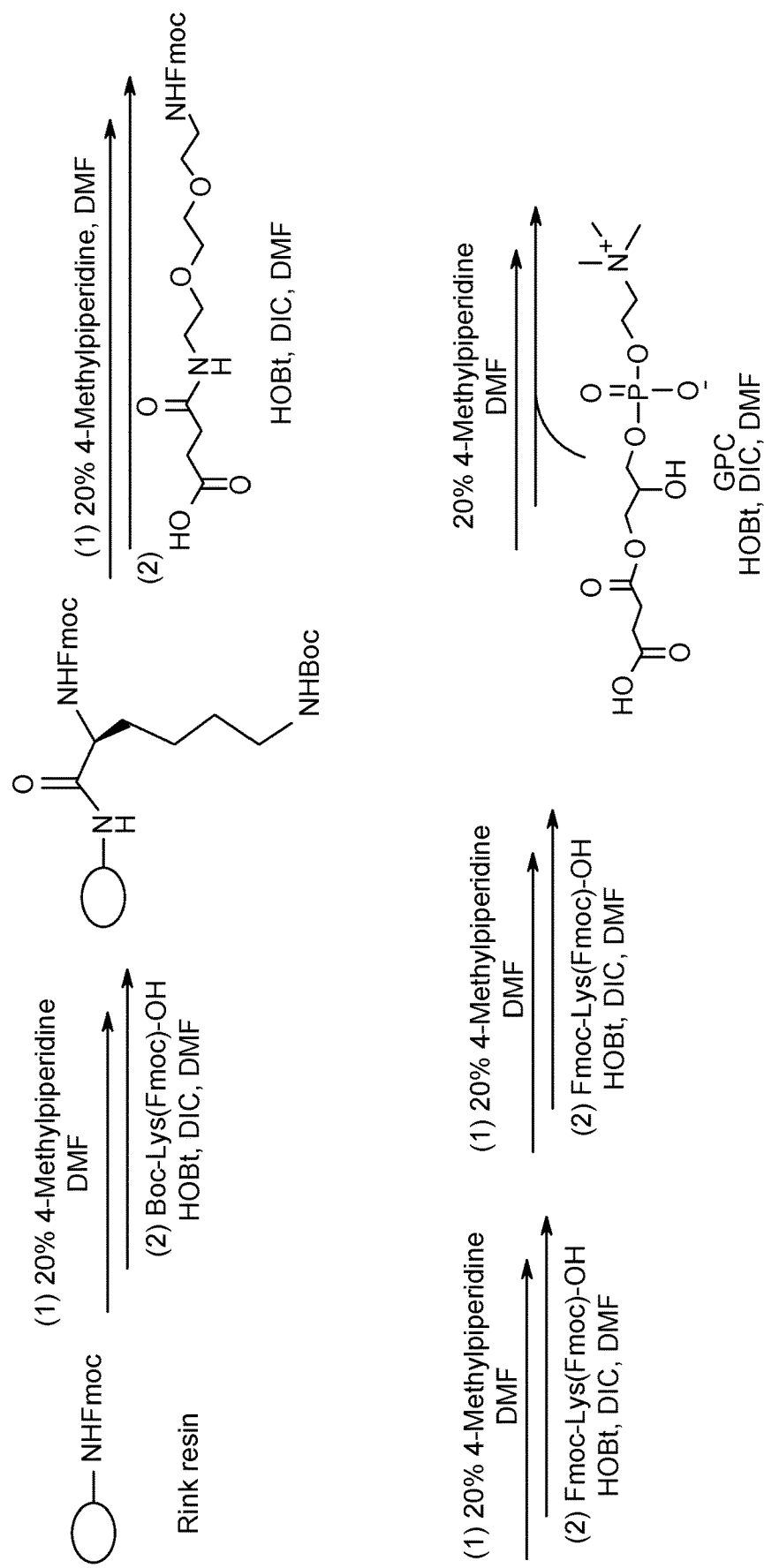
Figure 9B:
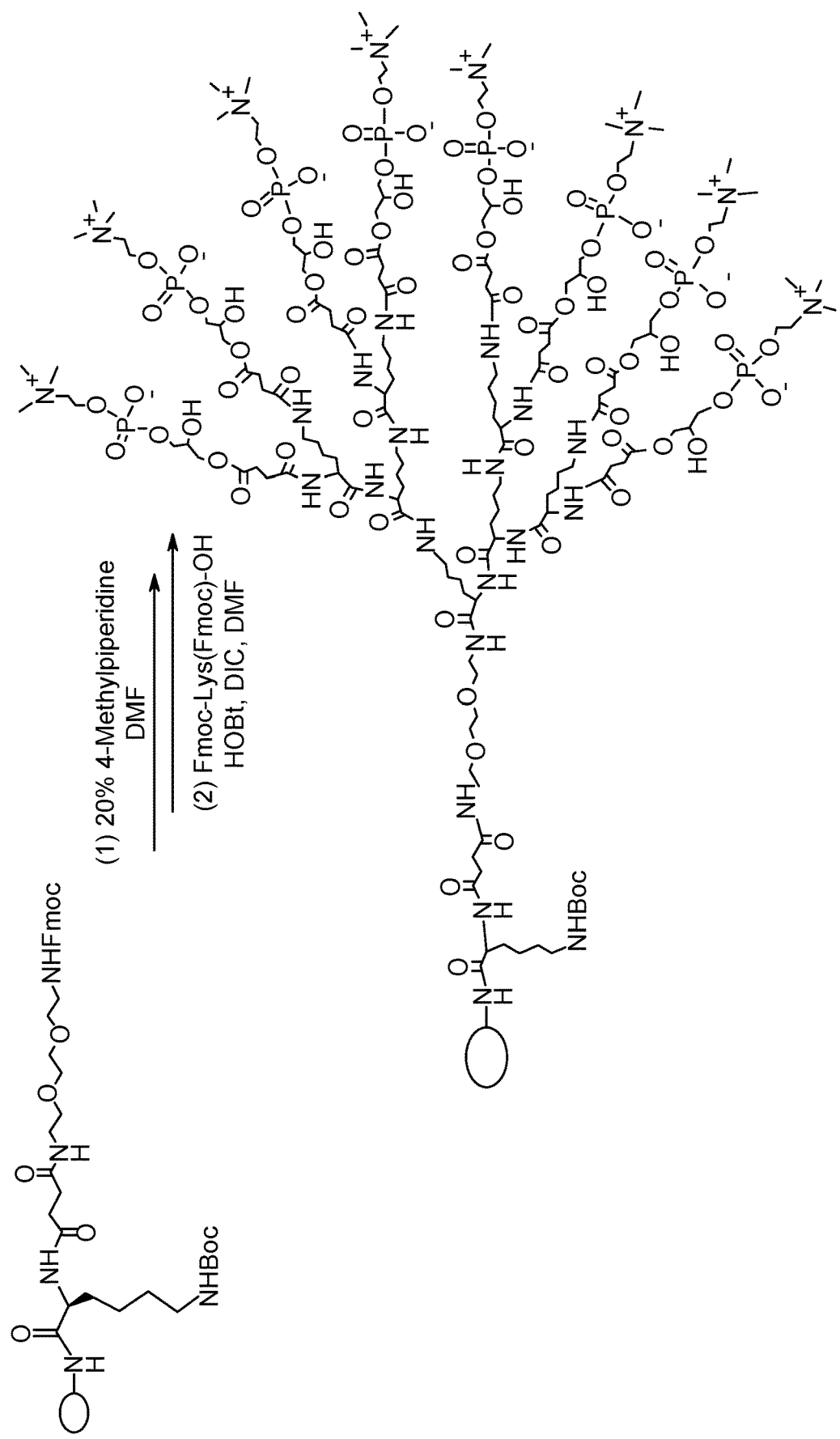
Figure 9B:
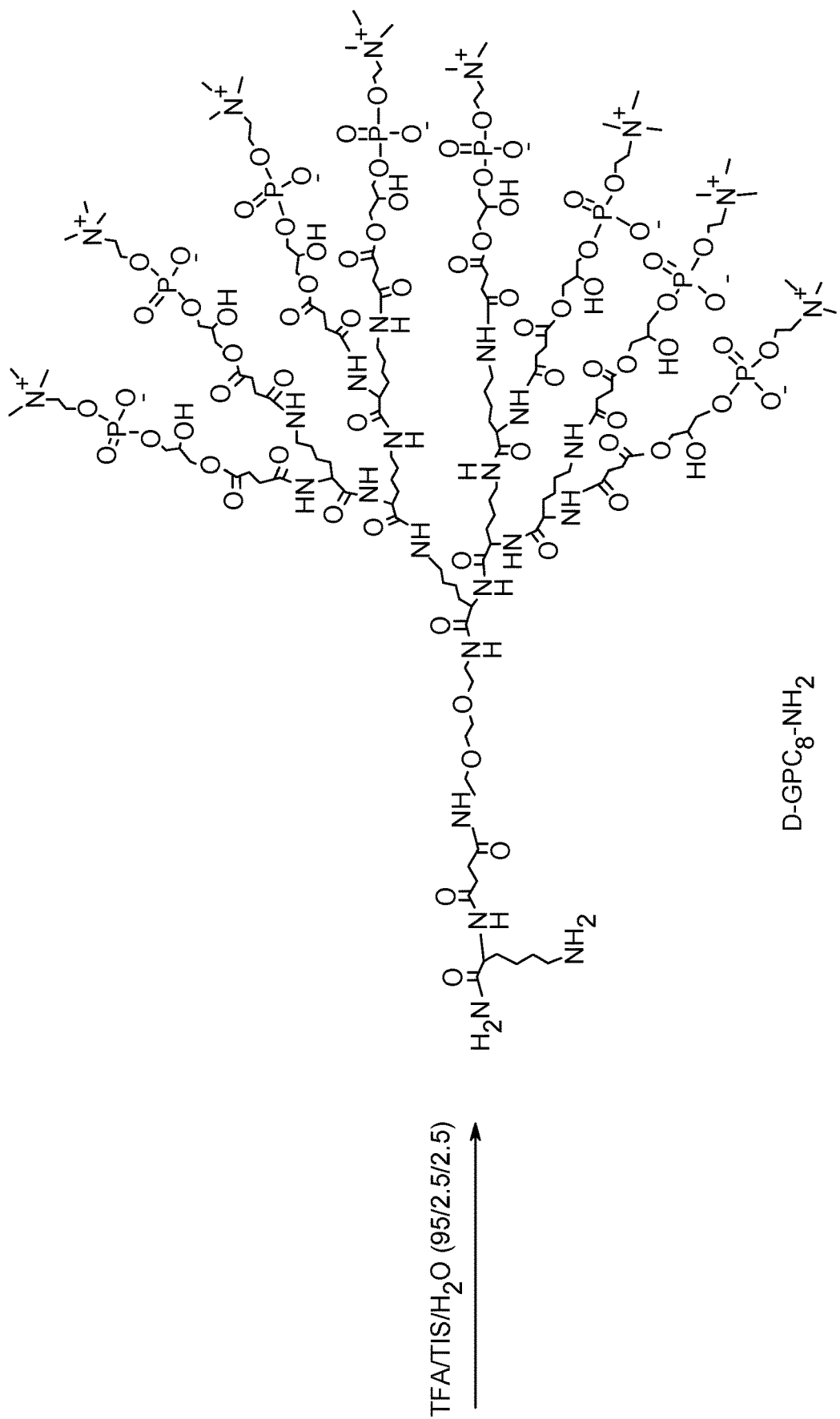

We utilized BLI assay to study the integrated protein binding and non-fouling properties of Janus-type amphiphilies as illustrated in FIG. 6A. Amine reactive biosensor immobilized with BSA was immersed in polymer solution with varying concentrations for kinetic binding study followed by dissociation kinetic assay in BSA solution (5 mg/mL). As shown in FIG. 5 B-D, $CB_{16}$-$Arg_4C17_4$ and $GPC_8$-$Arg_4C17_4$ exhibit dramatically slower association as compared to PEG analogue of $PEG^{5k}$-$Arg_4C17_4$, which is likely attributed to the zwitterionic component of the polymers that resist to diffusion to BSA surface. Notably, the slow dissociation was observed for $CB_{16}$-$Arg_4C17_4$ and $GPC_8$-$Arg_4C17_4$, indicating the prevention of competing binding of bulk BSA under sink condition due to the low fouling of zwitterionic surface that stabilize the polymer coating on biosensor. Polymers with the exact protein binding partner and different hydrophilic surface demonstrated different binding behaviors, showing association constants ($K_{on}$) of $1.32 \times 10^4 \pm 7.63 \times 10^1$, $9.55 \times 10^2 \pm 4.69$, and $1.93 \times 10^3 \pm 8.96$ for polymers with PEG, CB and GPC surface respectively.

FRET and agarose gel electrophoresis studies of BSA loading by zwitterionic nanoparticles. The encapsulation of protein by zwitterionic polymer was investigated by establishing a FRET system using FITC-labeled $CB_{16}$-$Arg_4C17_4$ and RB-labeled BSA (RB-BSA). The fluorescence spectra were collected at an excitation wavelength of 439 nm for emitter FITC and the appearance of emission maximum at 584 nm characteristic of RB indicate FRET occurrence. Significant FRET signal was detected by mixing polymer and BSA at ratio of 50/50 (w/w) (as shown in FIG. 6A), which suggests that the encapsulation of RB-BSA by polymer brings two fluorochroms in close proximity for efficient energy transfer. We further assessed the stability of the polymer/BSA complex upon the exposure to varying concentration of BSA. The addition of BSA can induce the dissociation of FITC-$CB_{16}$-$Arg_4C17_4$/RB-BSA assembly, leading to the change in FRET ratio. The result indicates that slight decrease in FRET ratio change was observed in the presence of BSA ranging from 5 to 40 mg/mL.

We further applied agarose gel retention assay to study the loading of FITC-BSA by zwitterionic dendrimers. Positively charge FITC-BSA migrates on agarose gel from original under electrophoresis. Zwitterionic dendron of both D-$GPC_8$ and D-$CB_{16}$ show no capability to retain the FITC-BSA migration. In comparison, zwitterionc dendrimer possess both guanidine and hydrophobic functionalities can effectively sustain FITC-BSA migration, which is primarily attributed to two factors: (1) the larger size of polymer/BSA aggregates; (2) neutralization of positively charged BSA with negatively charged polymer.

Cellular uptake of protein/drug delivered by zwitterionic nanocarriers. The internalization of protein/drug loaded zwitterionic nanocarrier was studied against SKOV-3 cancer cell. As shown in Figure XA, no fluorescence signal was observed in cells exposed to free FITC-BSA for 1 h, indicating that FITC-BSA alone is not capable of crossing cell membrane. When loaded in $CB_{16}$-$Arg_4VE_4$ NPs, FITC-BSA was translocated into the cytoplasm. Folate targeting group modification facilitates FITC-BSA-loaded NP—CB internalization into cells compared to non-targeted NP—CB. Notably, dramatic intracellular uptake was observed in FITC-BSA loaded $GPC_8$-$Arg_4C17_4$ (Figure XB). The ability of NPs to deliver drug into cells was studied using DOX as model drug by taking advantage of its intricate fluorescence. Figure XB shows the cellular uptake of free DOX and DOX loaded in CB—$Rh_4$ and GPC-$Rh_4$. Strong fluorescence and absolute presence of DOX in nucleus suggest the fast diffusion of free DOX incubated with cell for 2 h. Both DOX-loaded zwitterionic NPs show weak cell uptake through the endocytotic pathway.

Conclusion. Polylysine-based Janus-type amphiphiles were designed and synthesized to display both protein binding and nonfouling properties. Protein binding segment interacts and encapsulates protein through hybrid noncovalent hydrophobic and charge interactions, resulting in the formation of therapeutic loaded self-assemblies. Zwitterionic dendrons are therefore exposed to the surface, rendering the nanoparticle with antifouling property to resist nonspecific protein binding in biological environment. The zwitterionic nanoparticles feature improved stabilities when challenged by external proteins, which is expected to be useful as therapeutic delivery vehicle for in vivo applications.

Example 2

The following is an example of the preparation, characterization, and use of zwitterionic dendrons of the present disclosure.

FIGS. 9 and 10 provides an example of the synthesis of zwitterionic dendrons of the present disclosure.

Example 3

The following provides examples of dendrimers comprising one or more zwitterionic dendrons of the present disclosure and protein and drug binding of the dendrimers.

Figure 12:
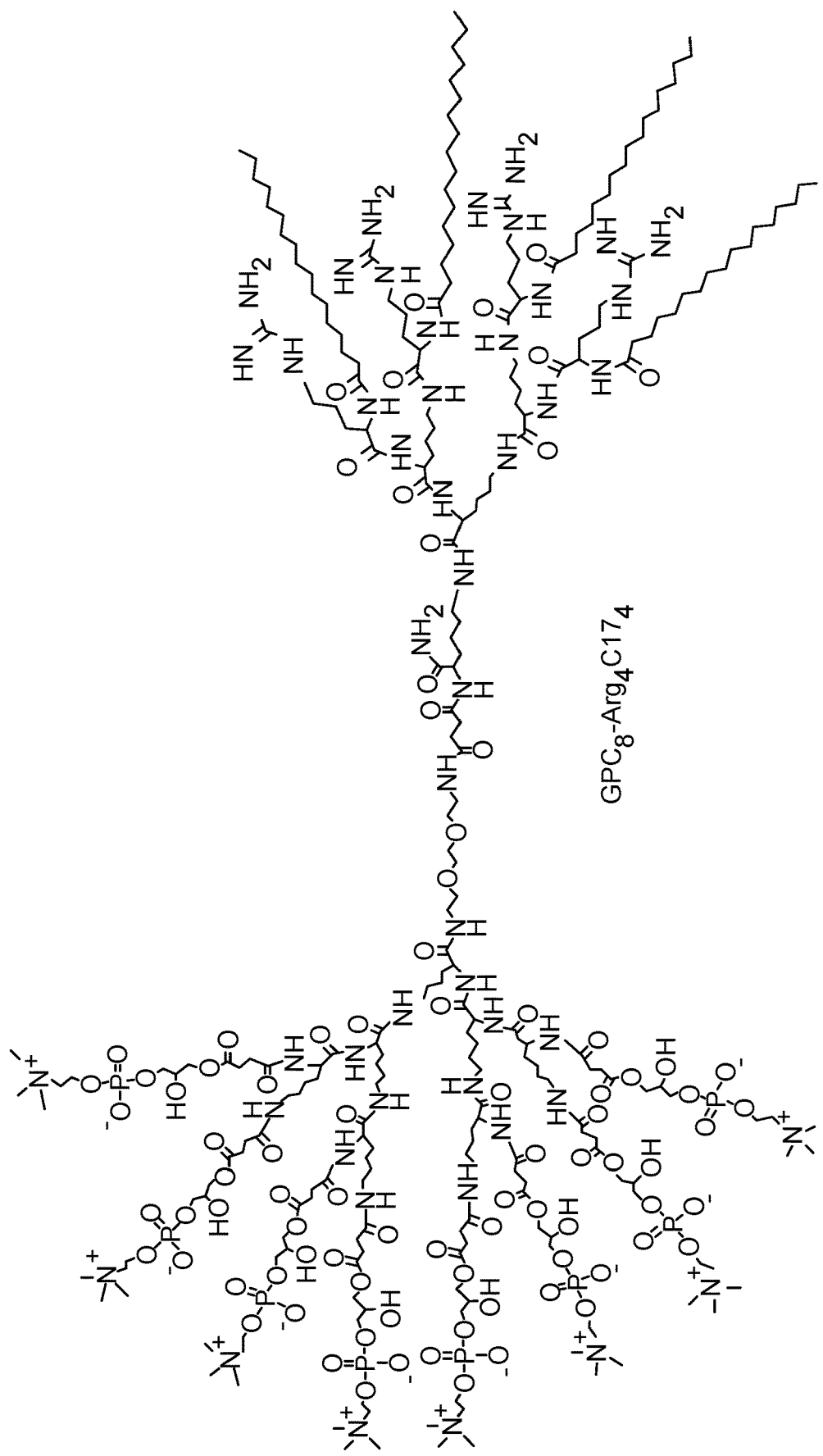
FIG. 12 shows examples of Janus-type zwitterionic amphiphilies, $GPC_8$-$Arg_4C17_4$, $CB_{16}$-$Arg_4C17_4$, $GPC_8$-$Rh_4$, and $CB_{16}$—$Rh_4$
Figure 12:
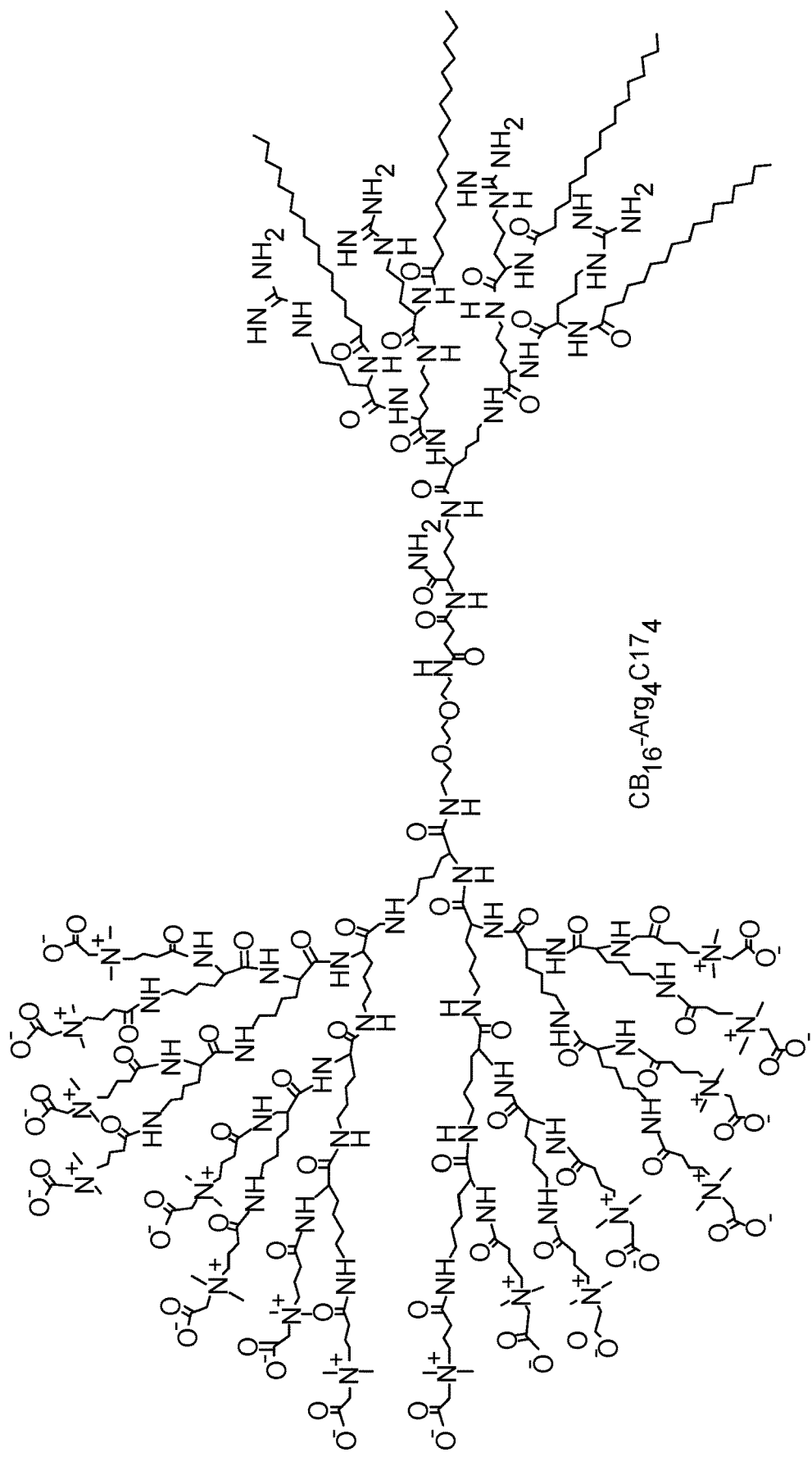
Figure 12:
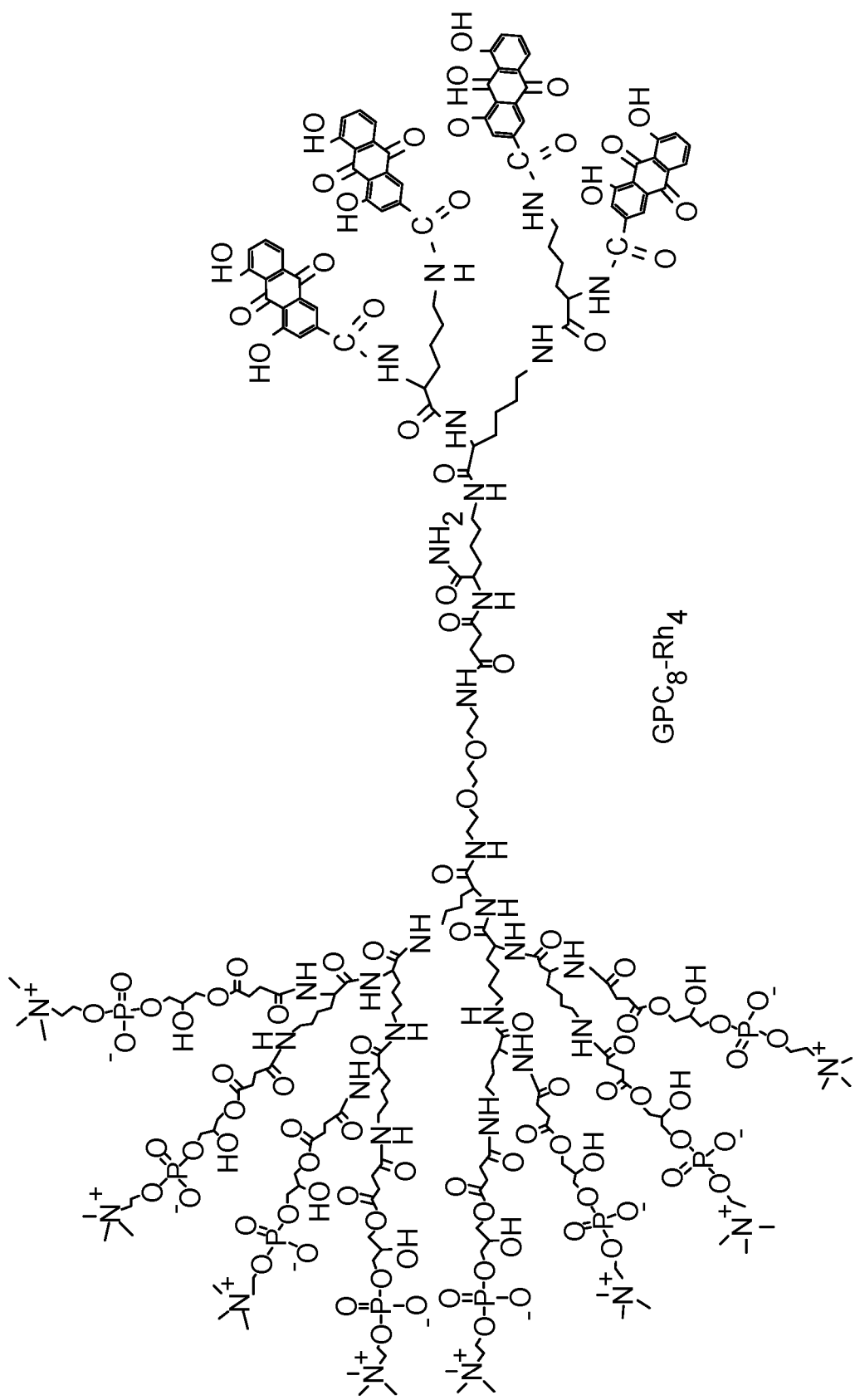
Figure 12:
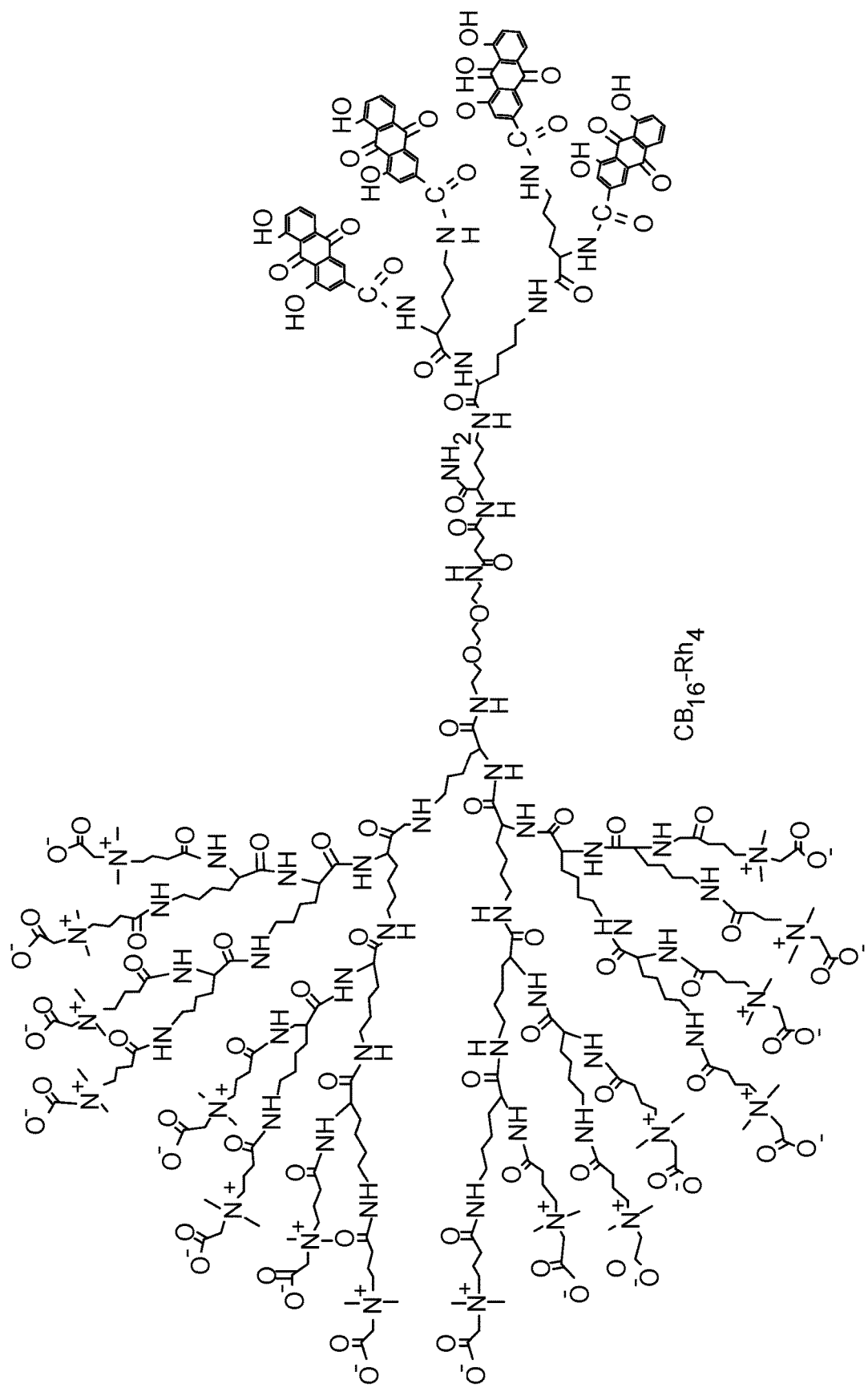
Figure 13:
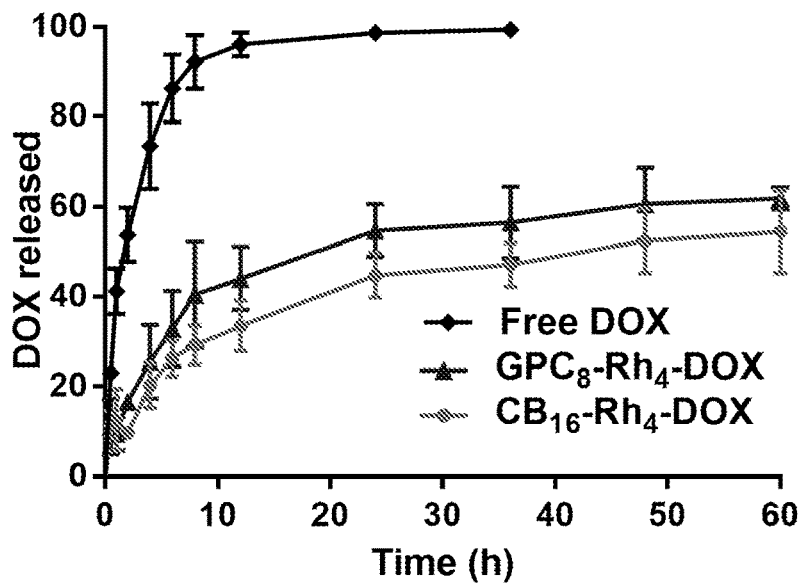
FIG. 13 shows data for in vitro DOX release of free DOX, $GPC_8$-$Rh_4$-DOX, and $CB_{16}$—$Rh_4$-DOX. (B) Blood circulation profiles of ovalbumin (RB-OVA) and ovalbumin loaded $GPC_8$-$Arg_4C17_4$ (GPC-RB-OVA), showing the prolonged circulation time of nanoformulation.
Figure 13:
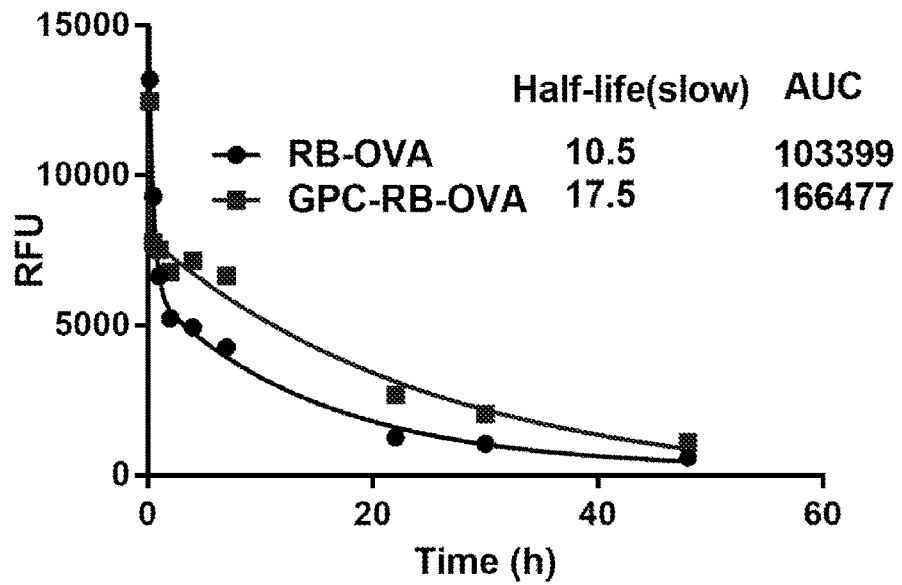
Figure 14:
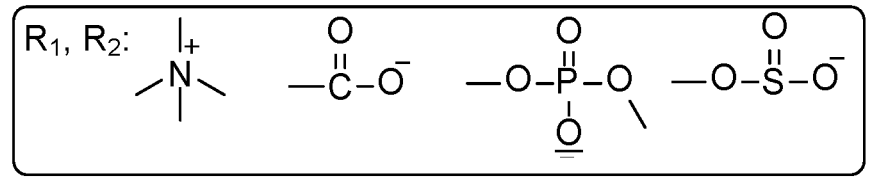
FIG. 14 shows examples of zwitterionic groups/moieties.
Figure 15:
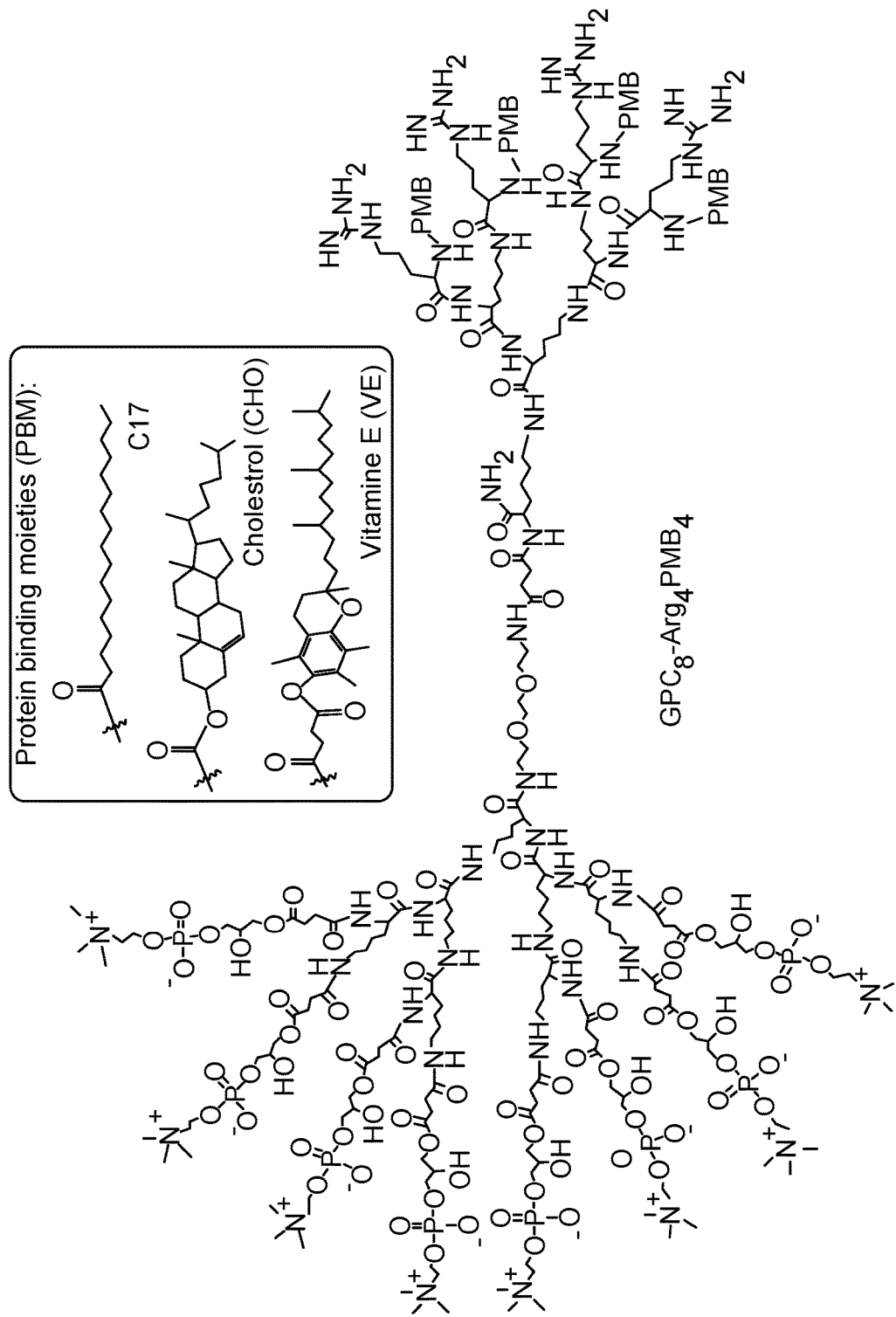
FIG. 15 shows examples of Janus-type zwitterionic amphiphilies for protein binding.
Figure 15:
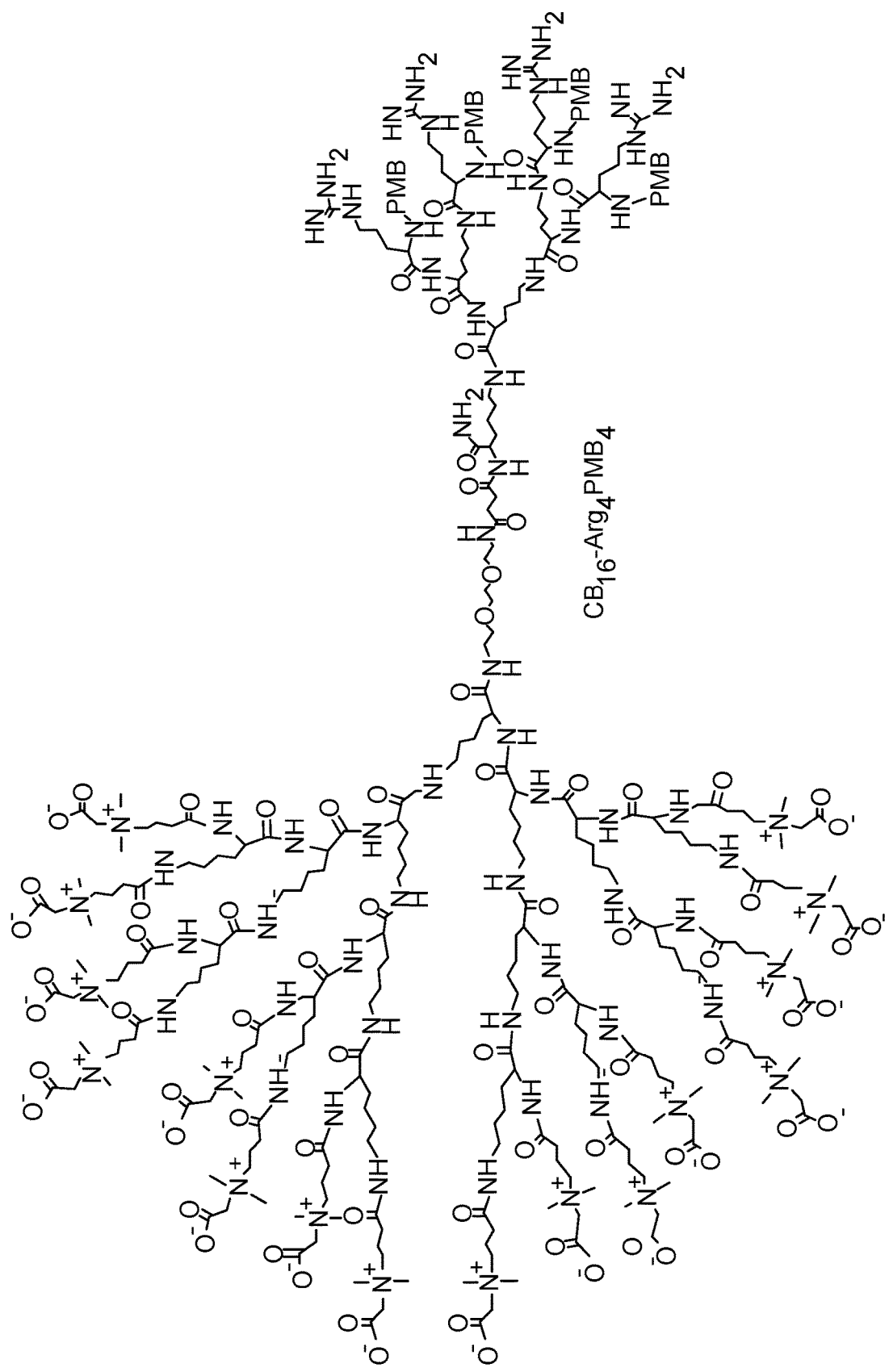
Figure 15:
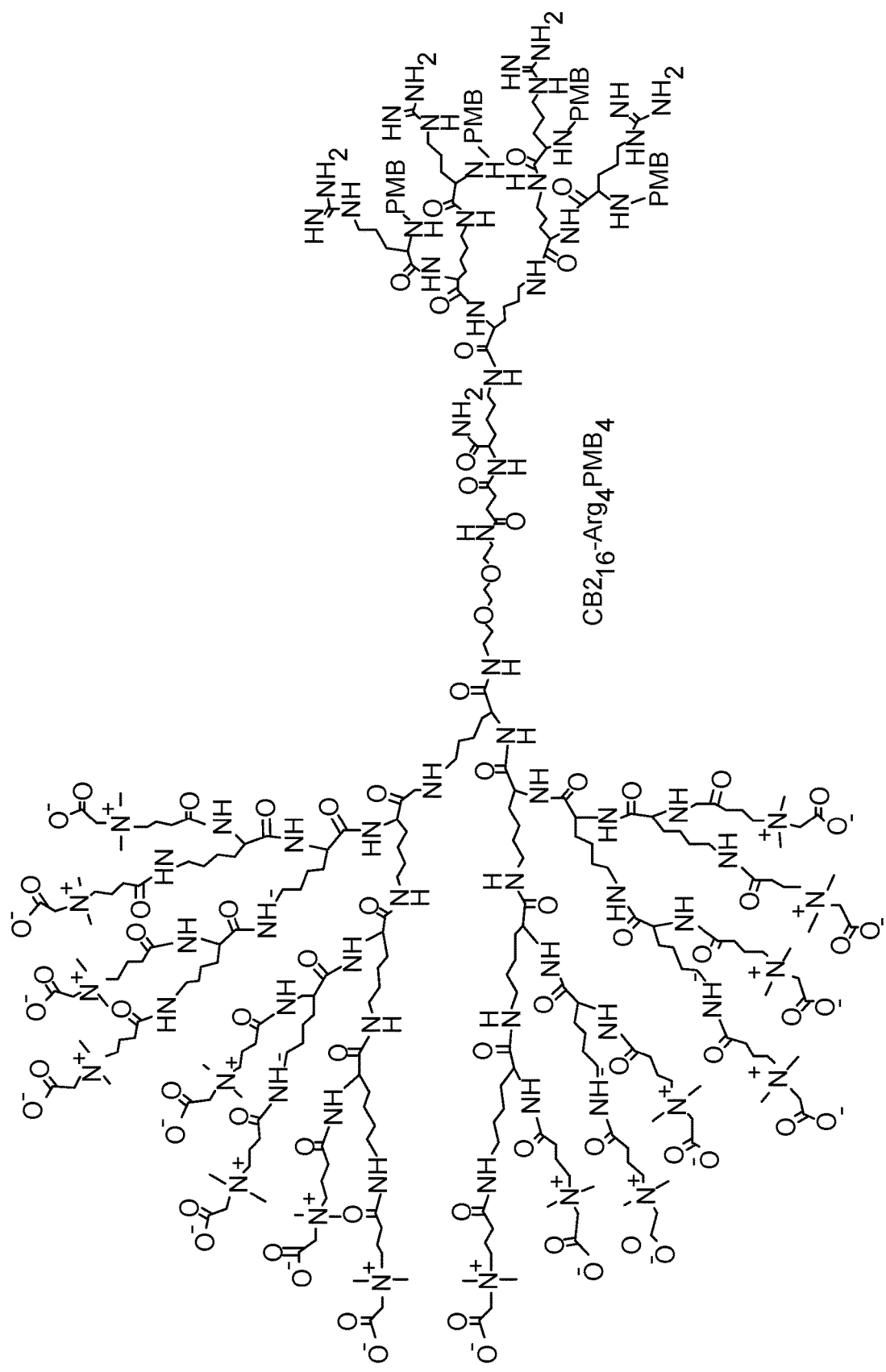
Figure 16:
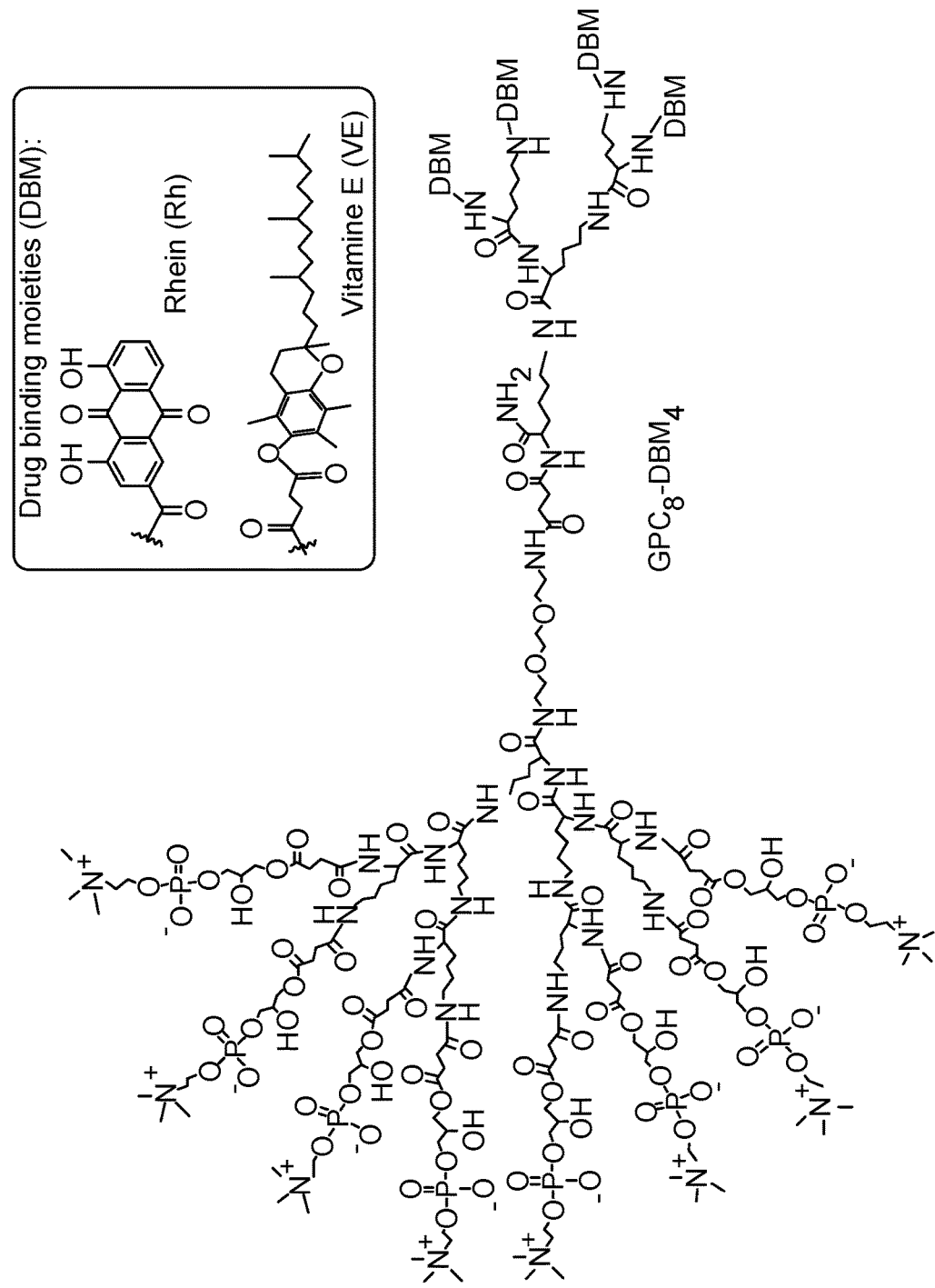
FIG. 16 shows examples of Janus-type zwitterionic amphiphilies for drug binding.
Figure 16:
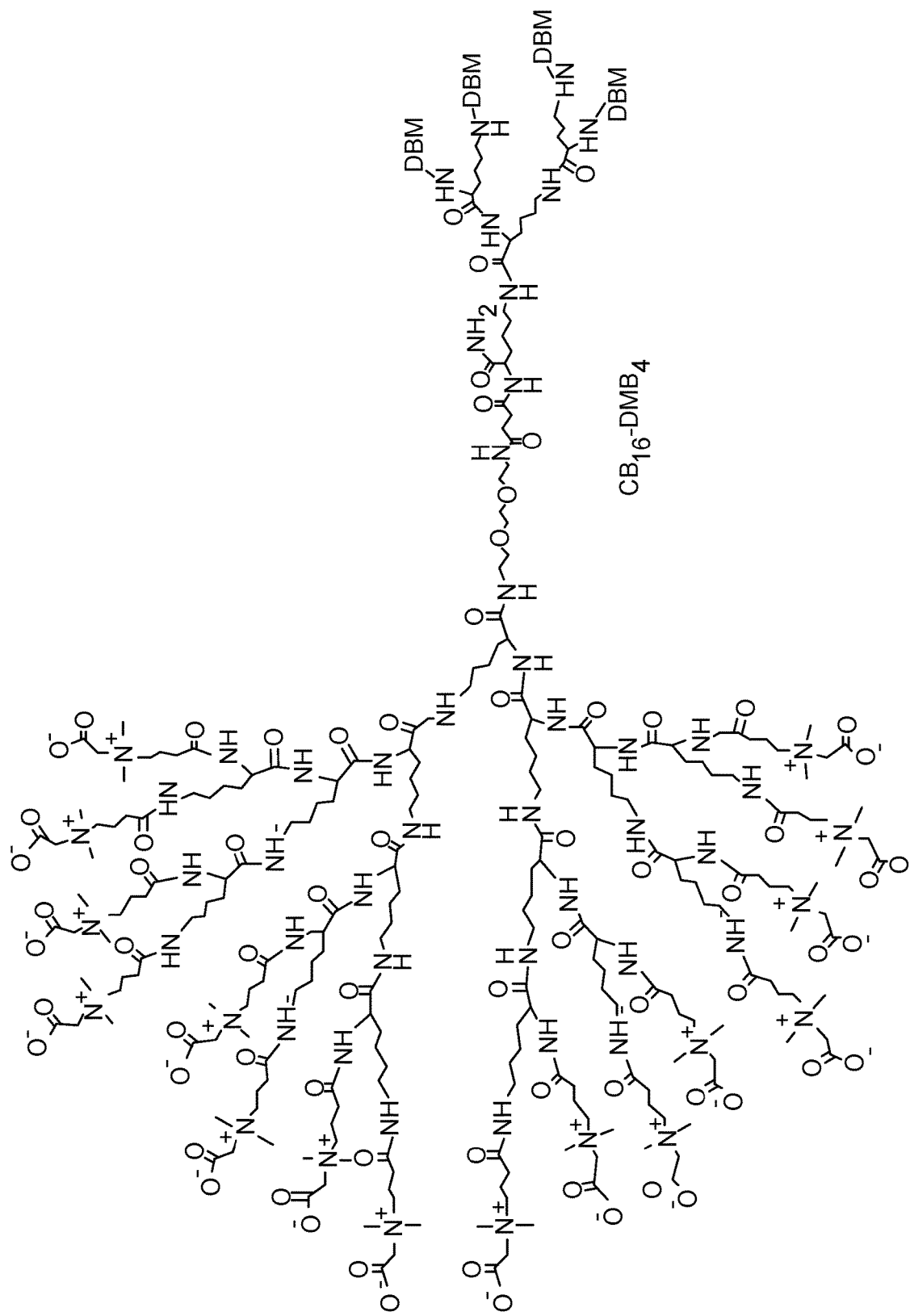
Figure 16:
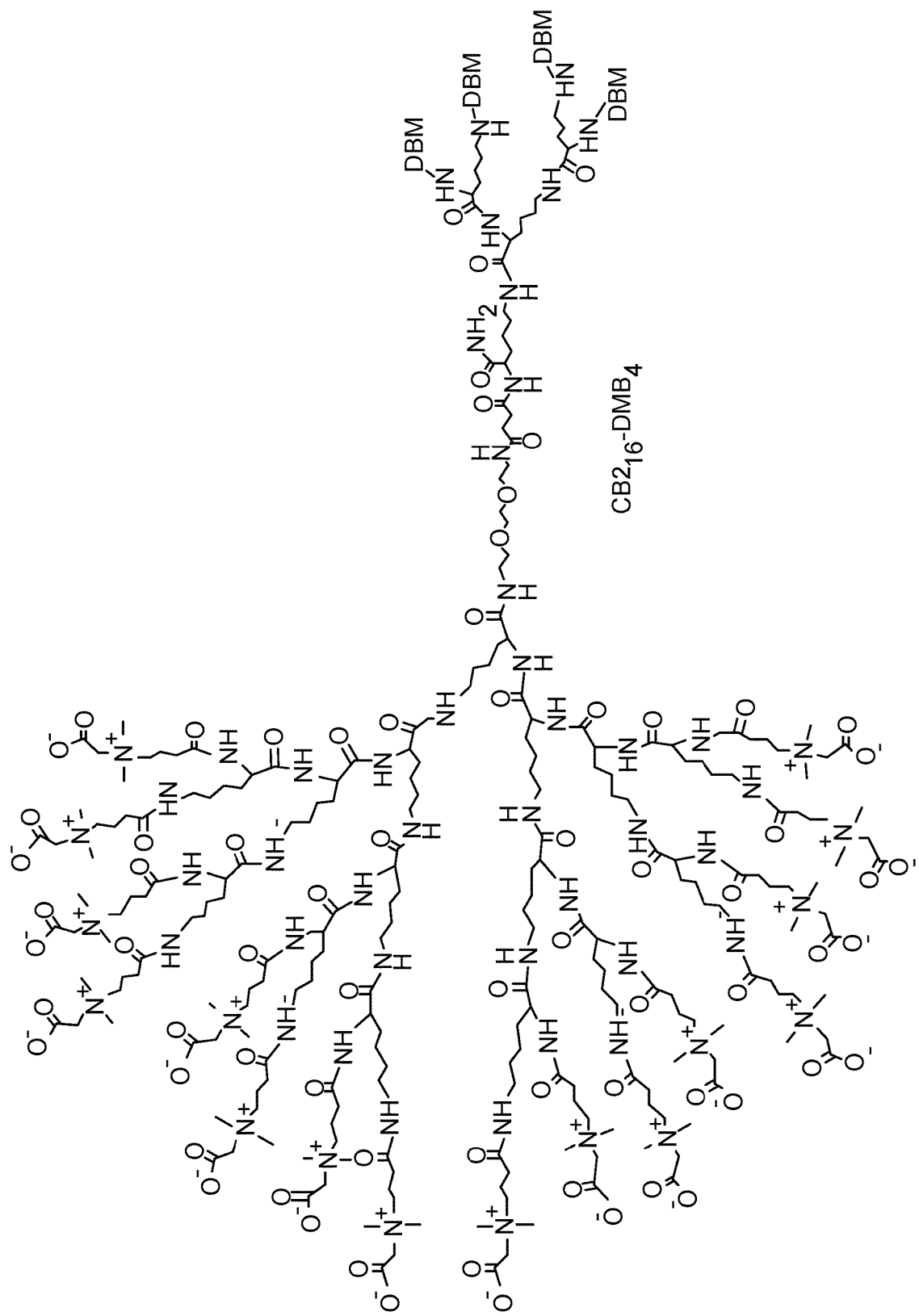
Figure 17:
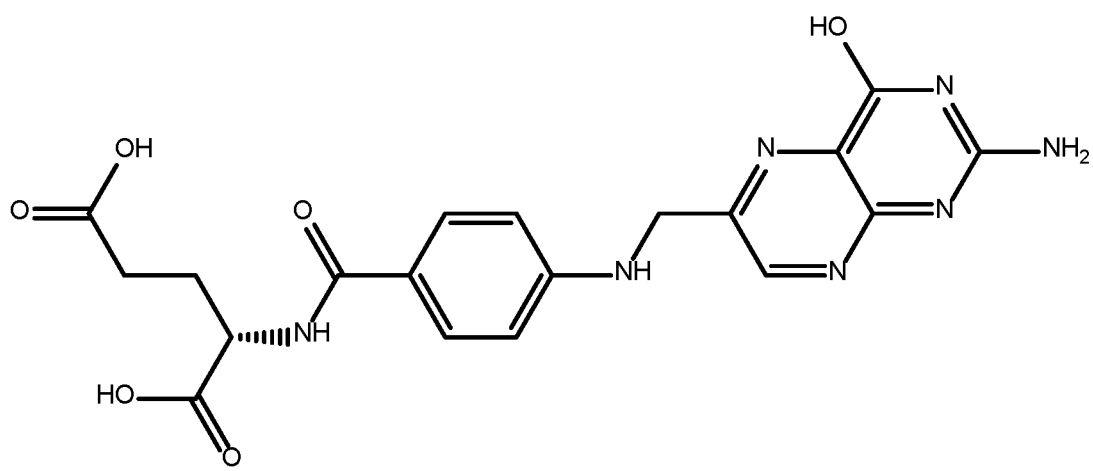
FIG. 17 shows an example of a targeting ligand (folic acid).
Figure 18:
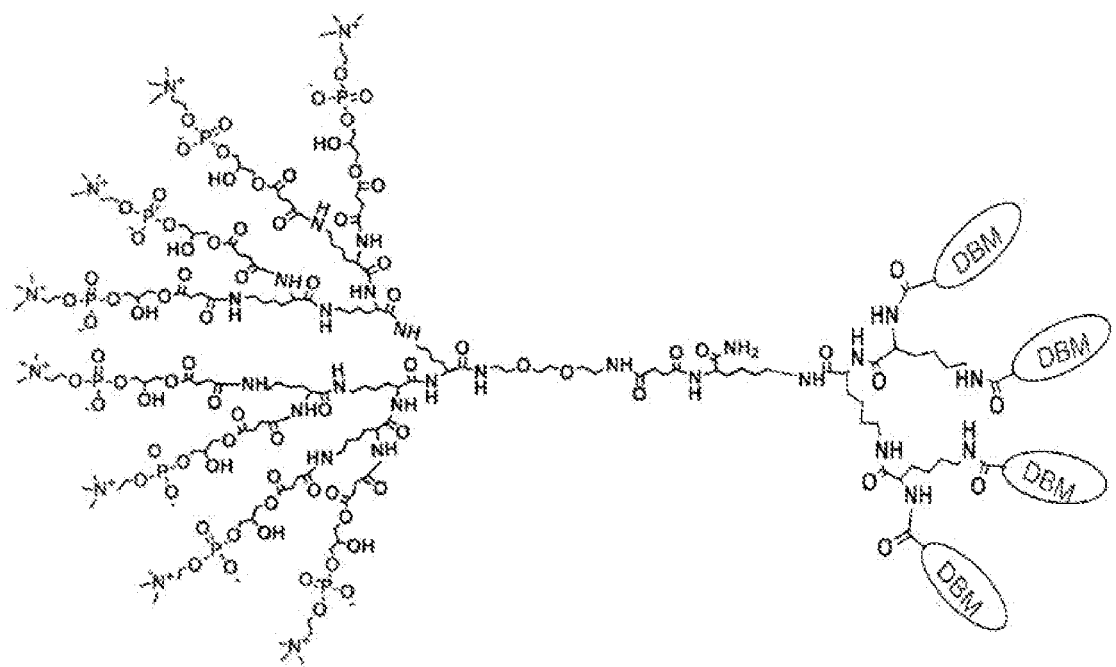
FIGS. 18-36 show examples of amphiphilic dendrimers of the present disclosure.
Figure 19:
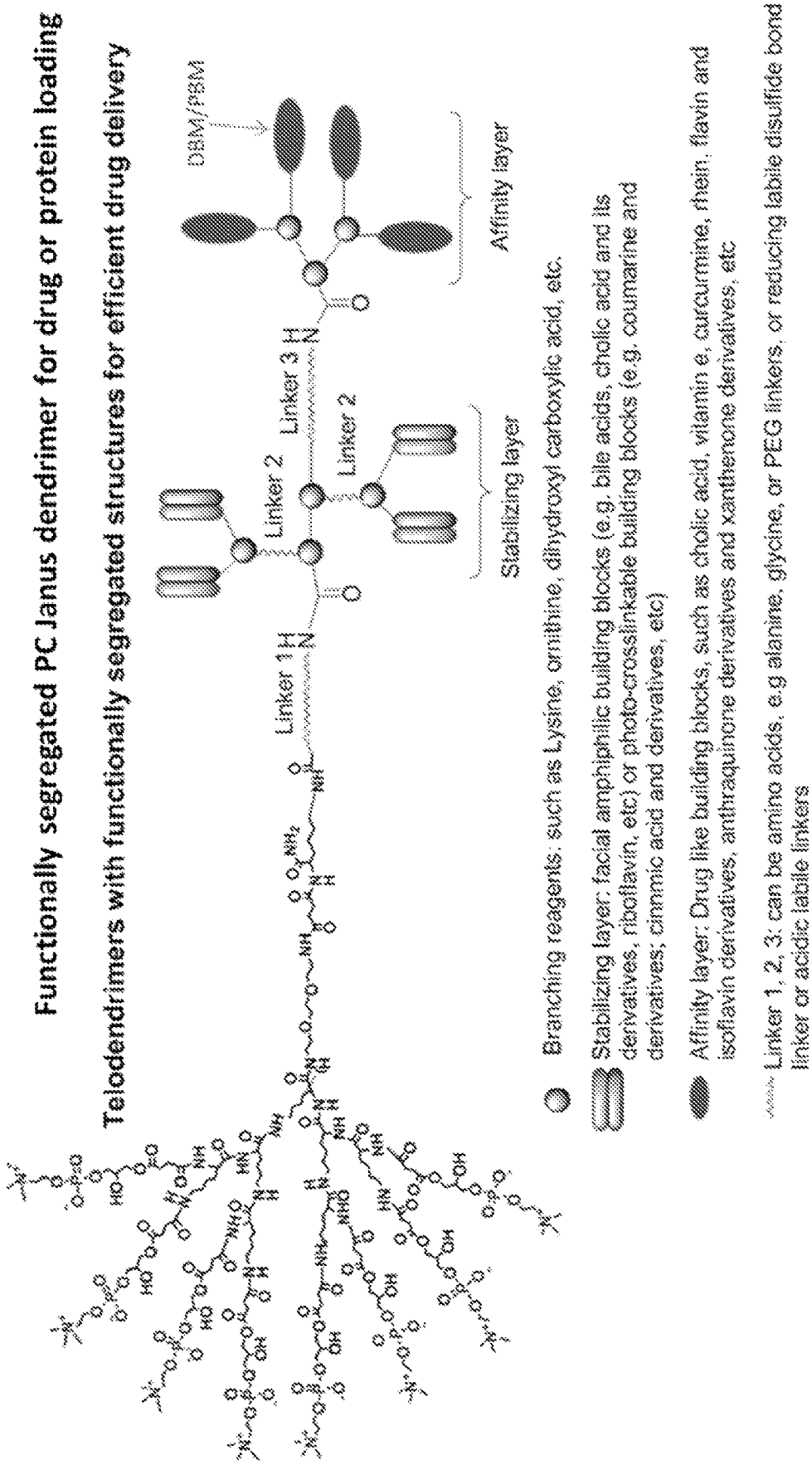
Figure 20:
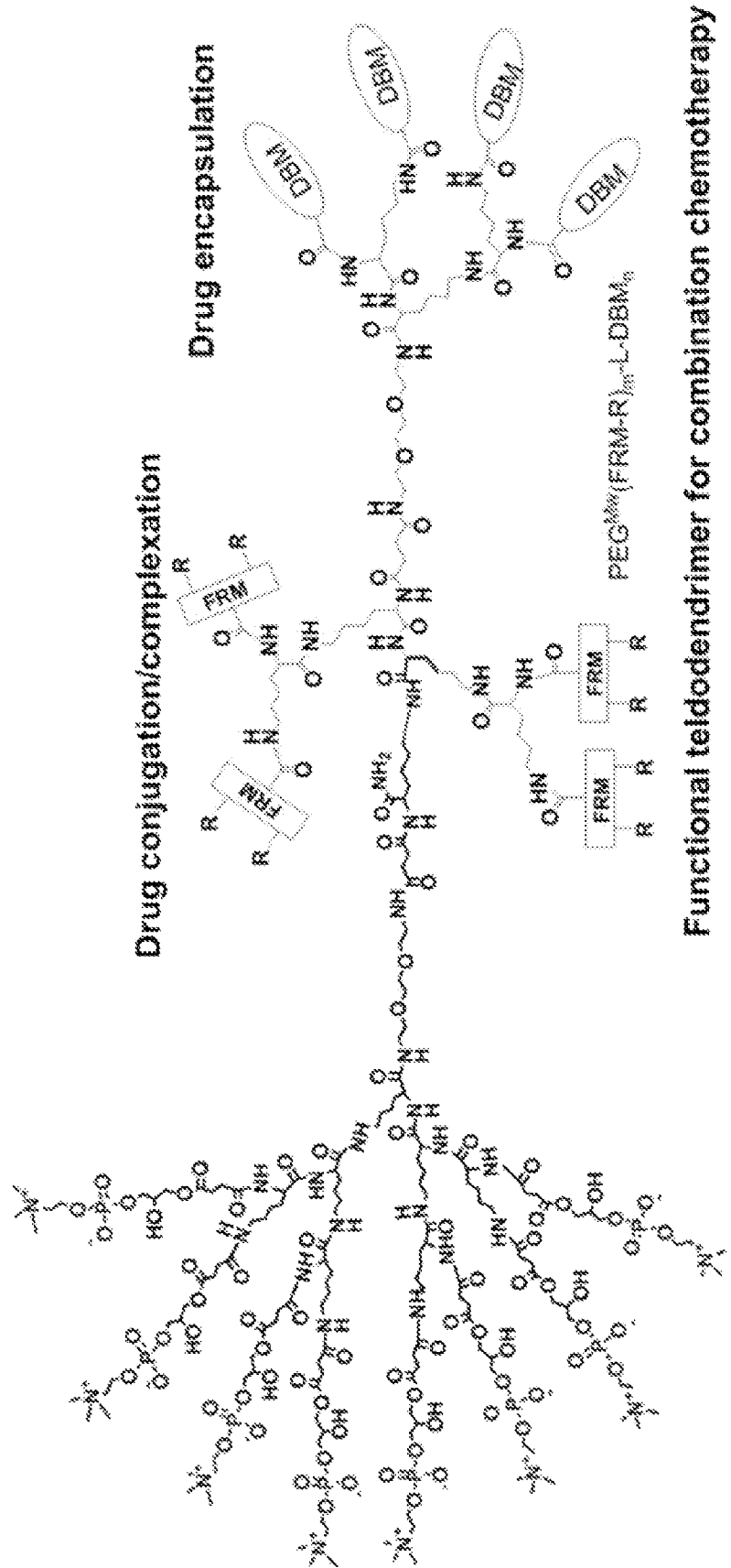
Figure 21:
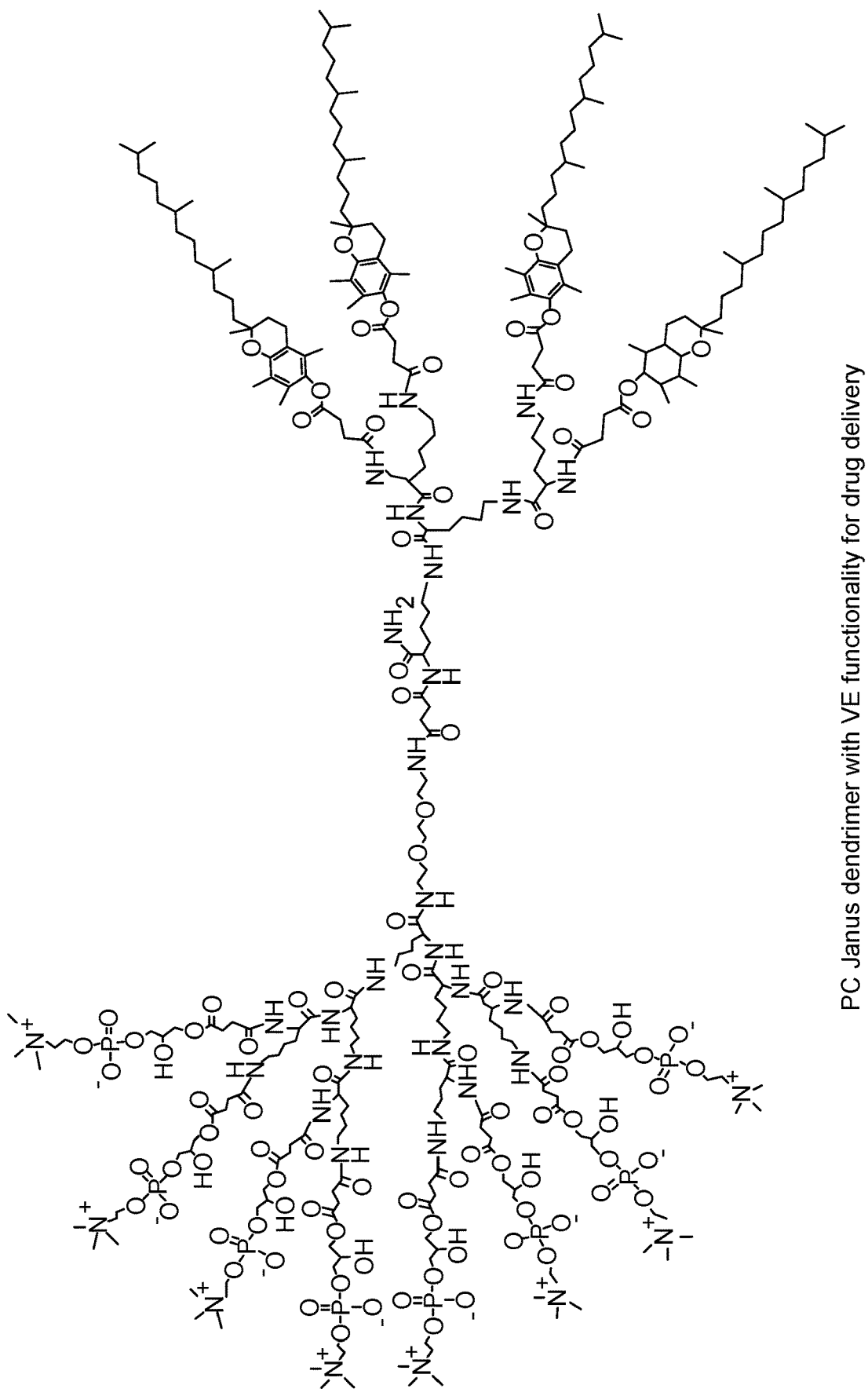
Figure 22:
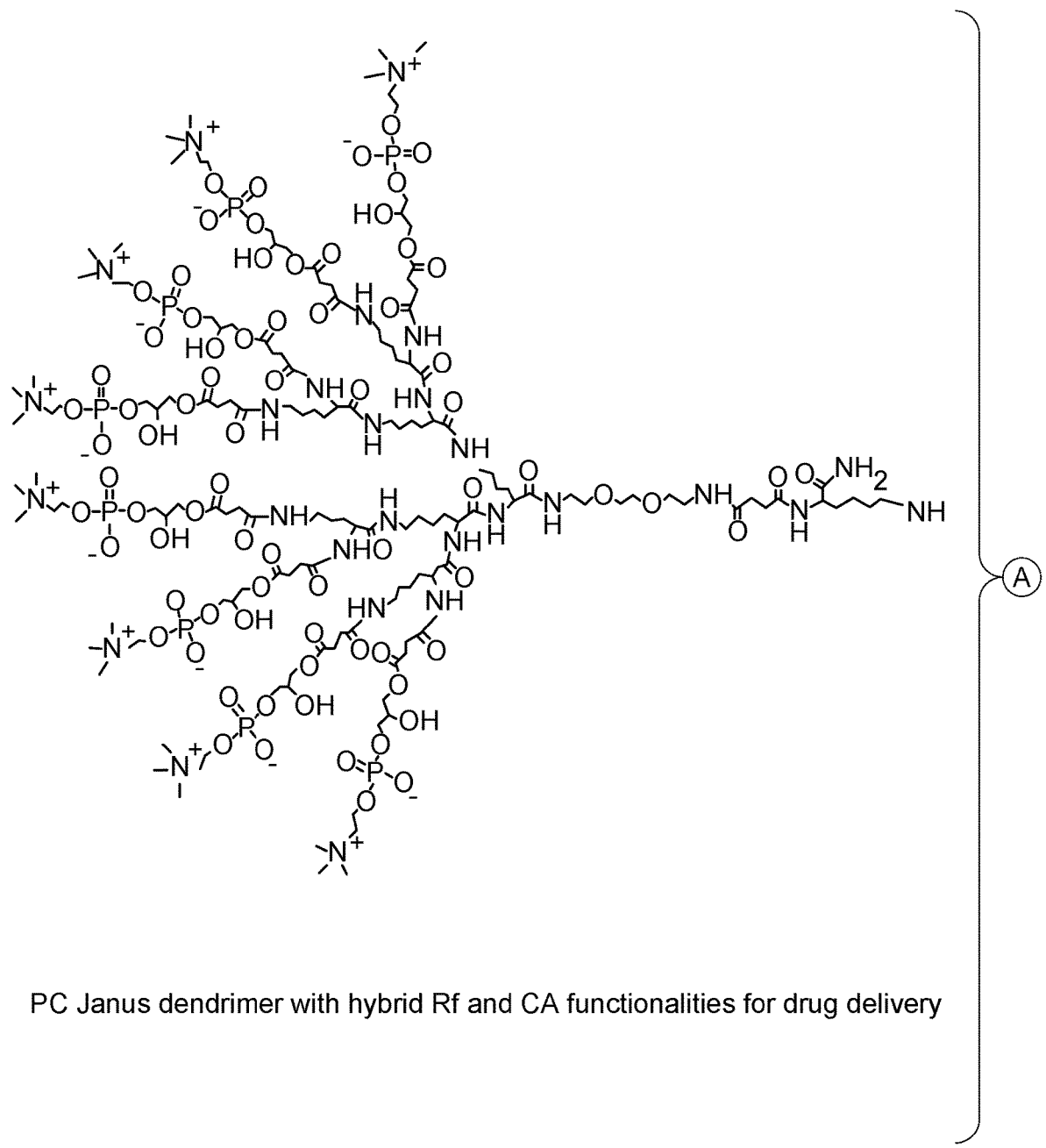
Figure 22:
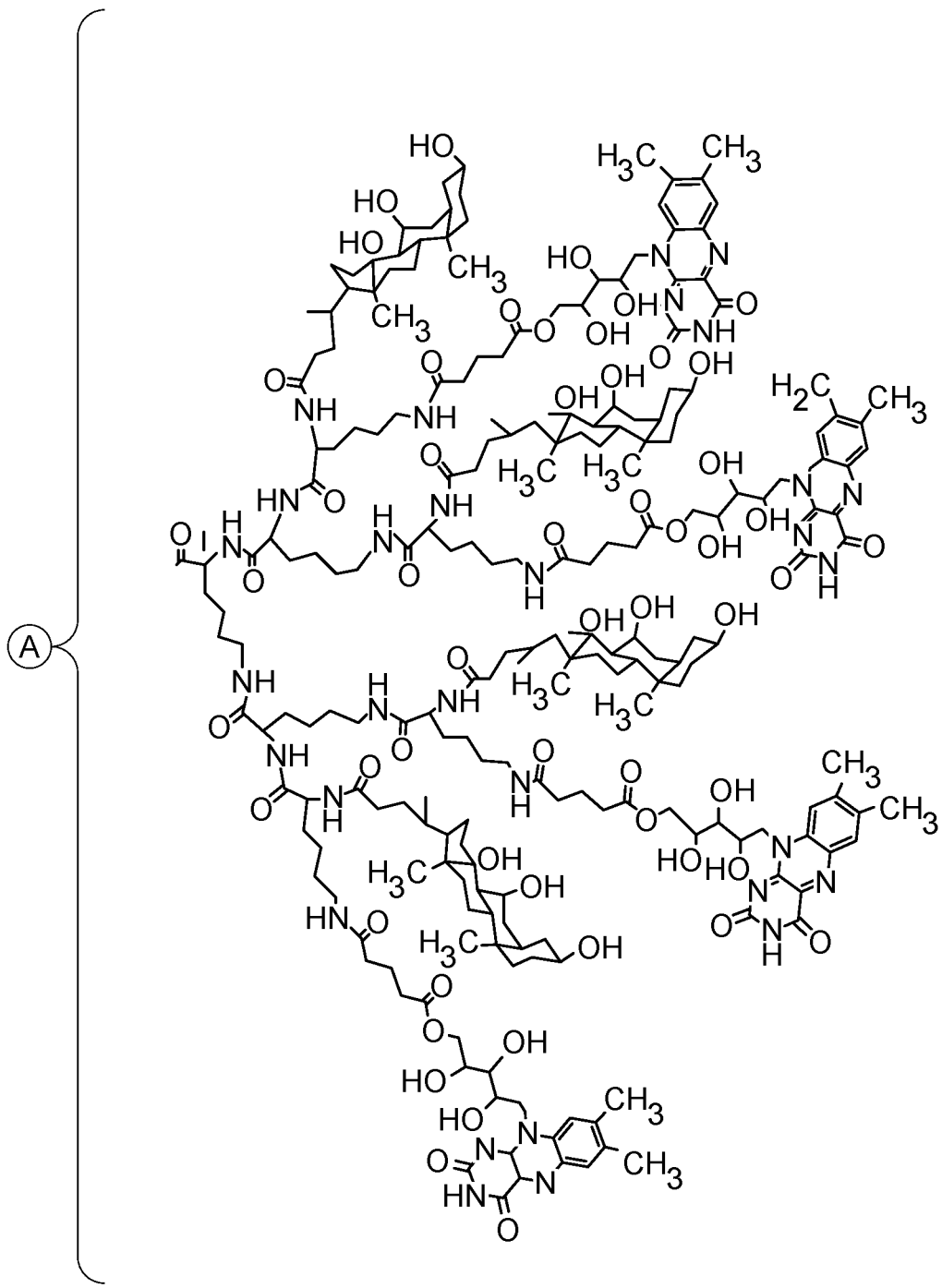
Figure 23:
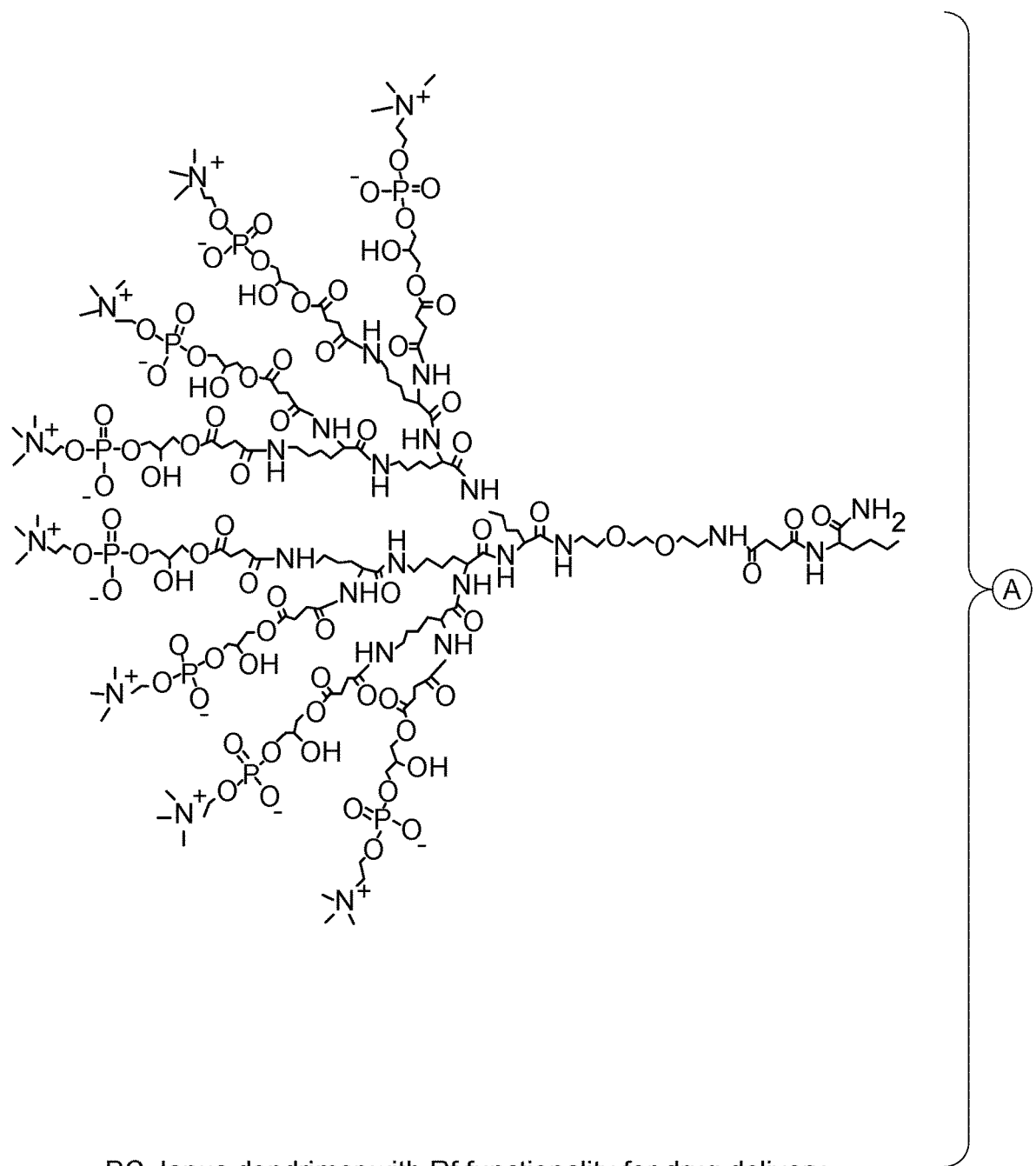
Figure 23:
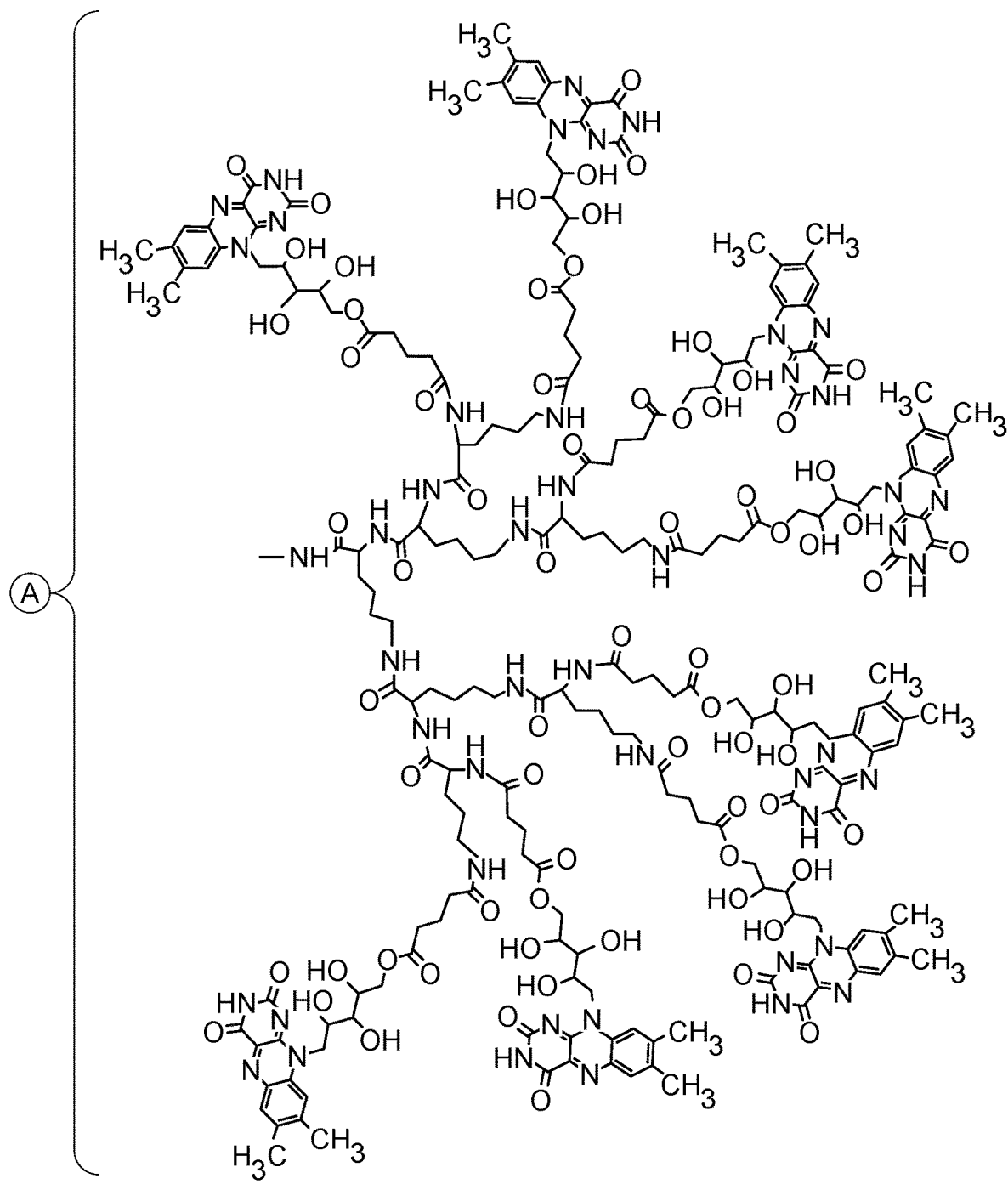
Figure 24:
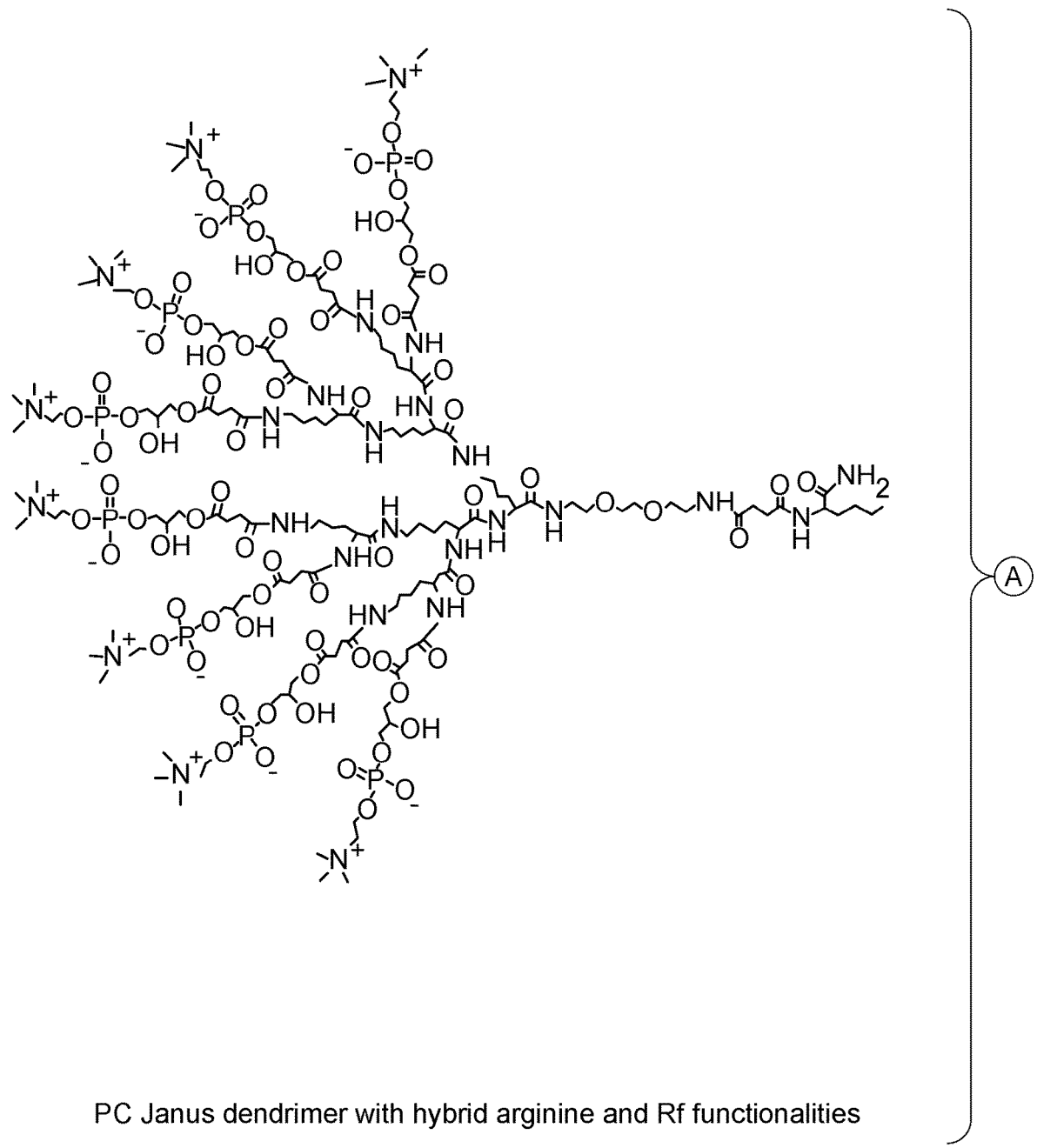
Figure 24:
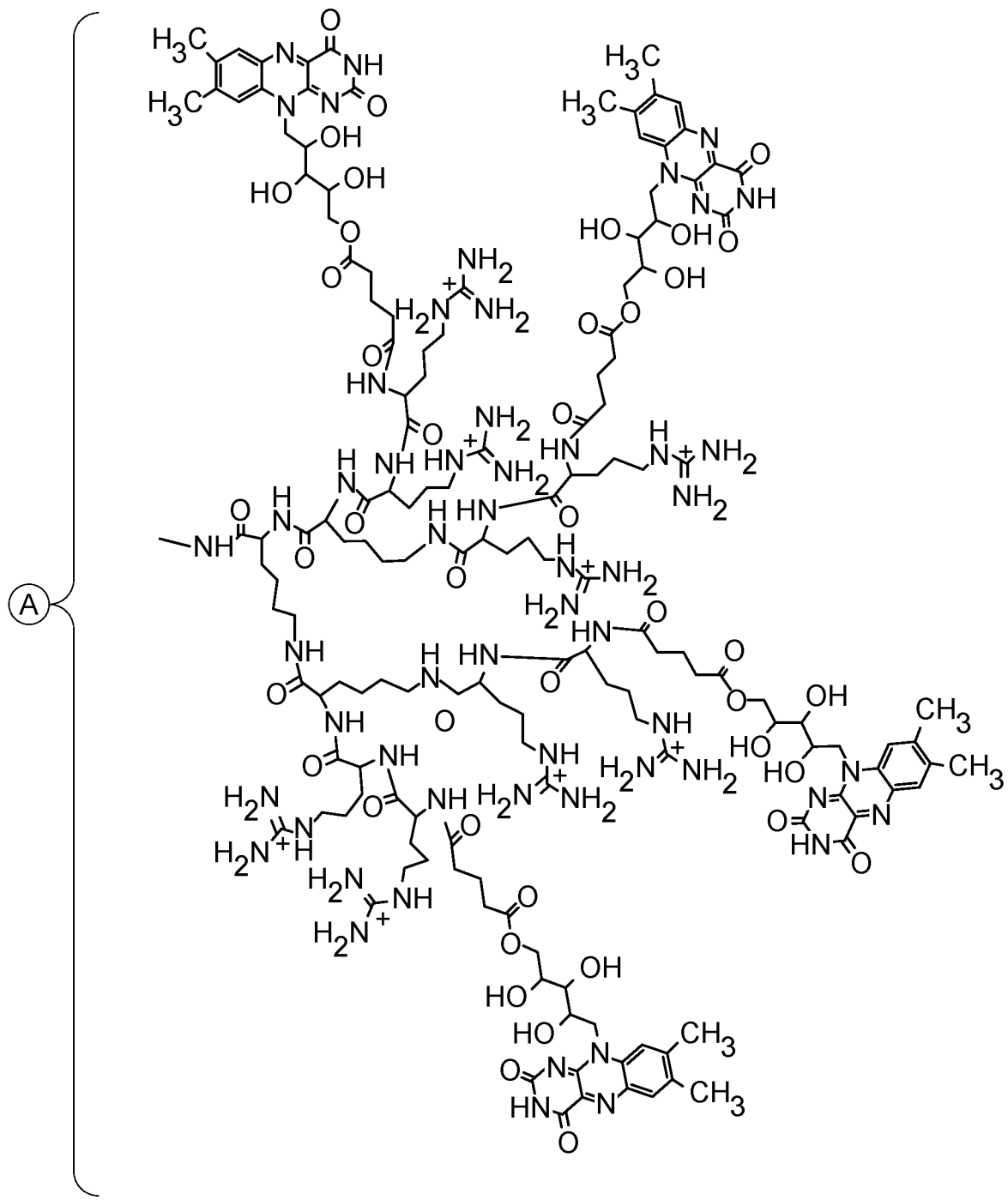
Figure 25:
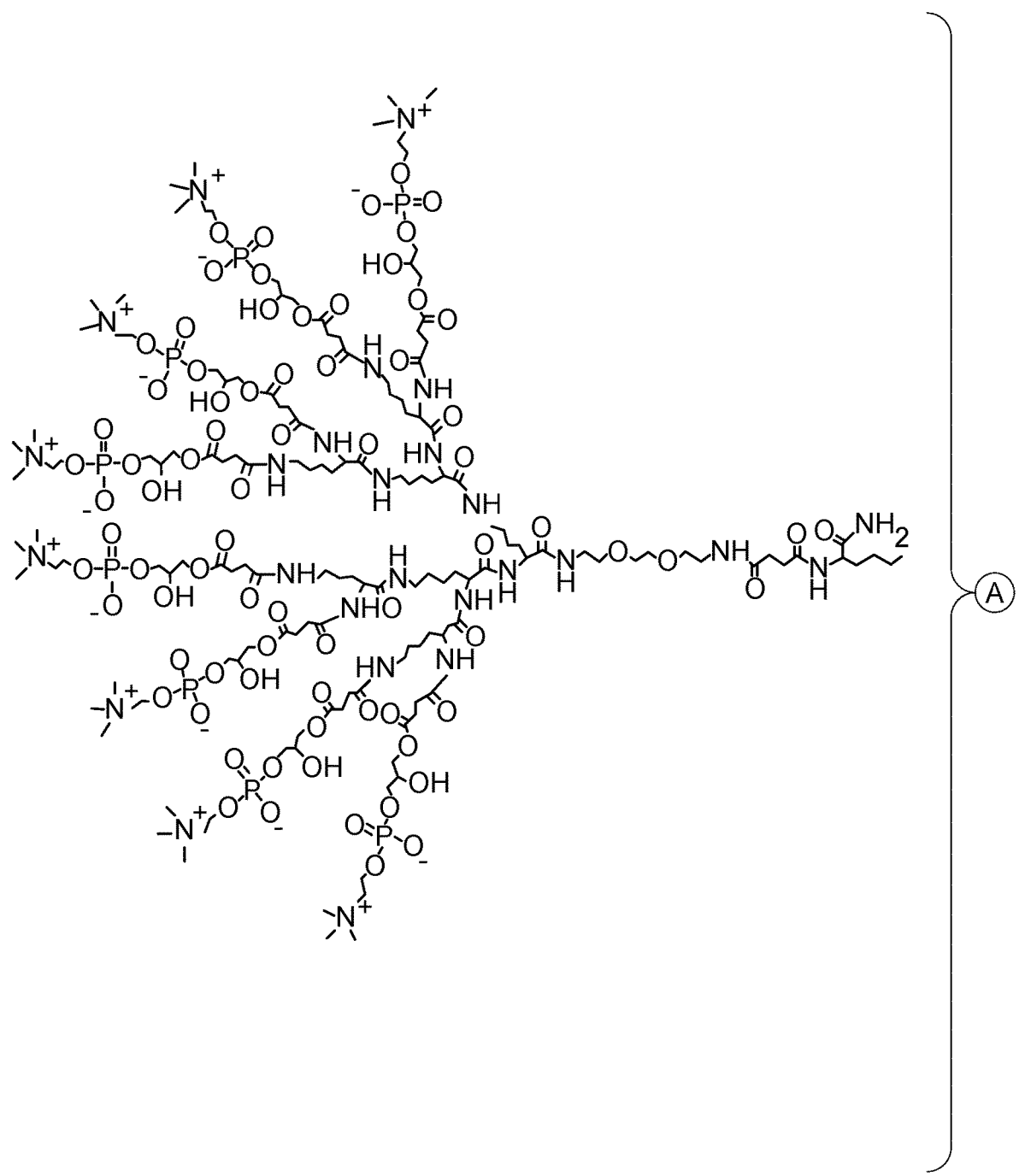
Figure 25:
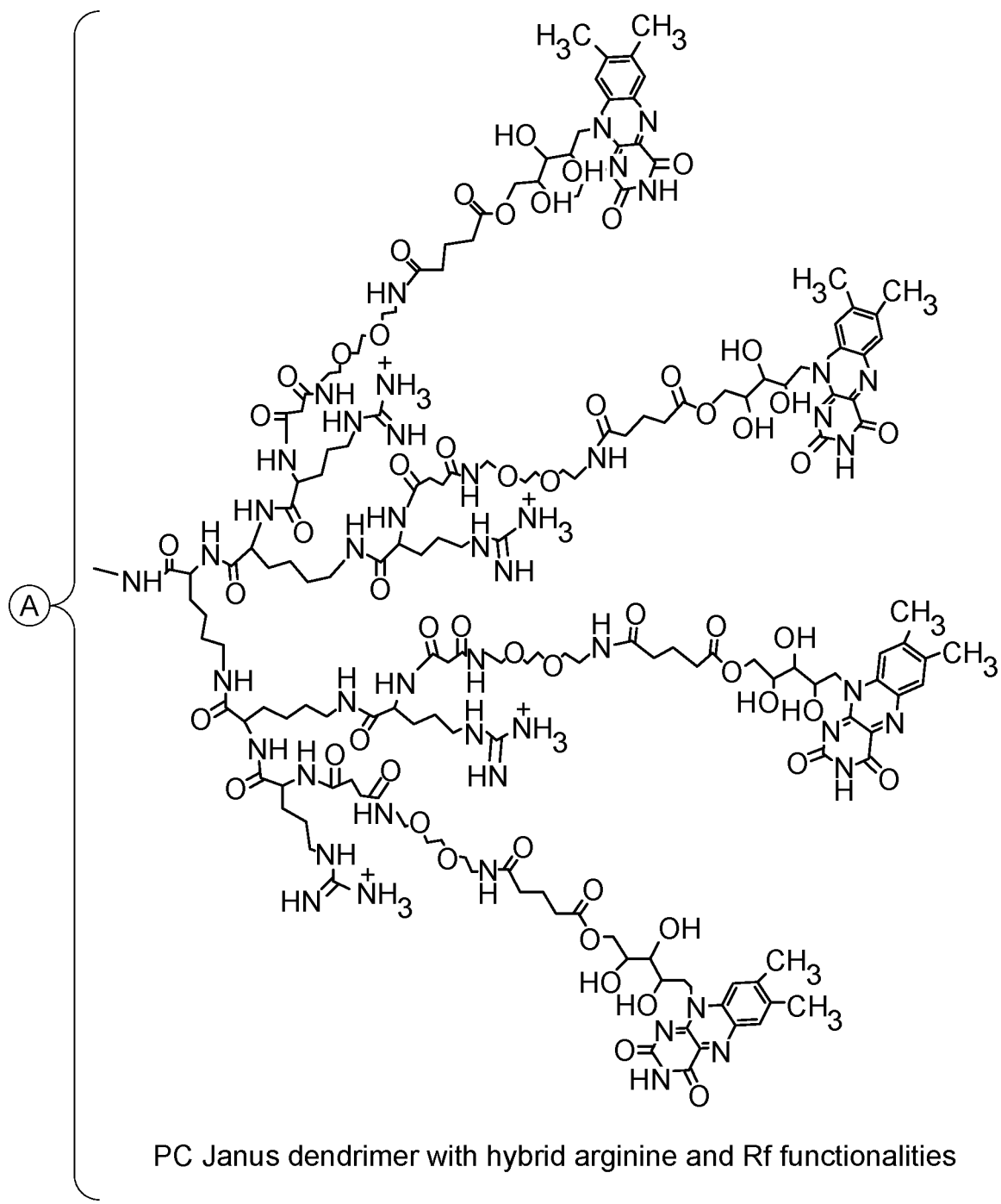
Figure 26:
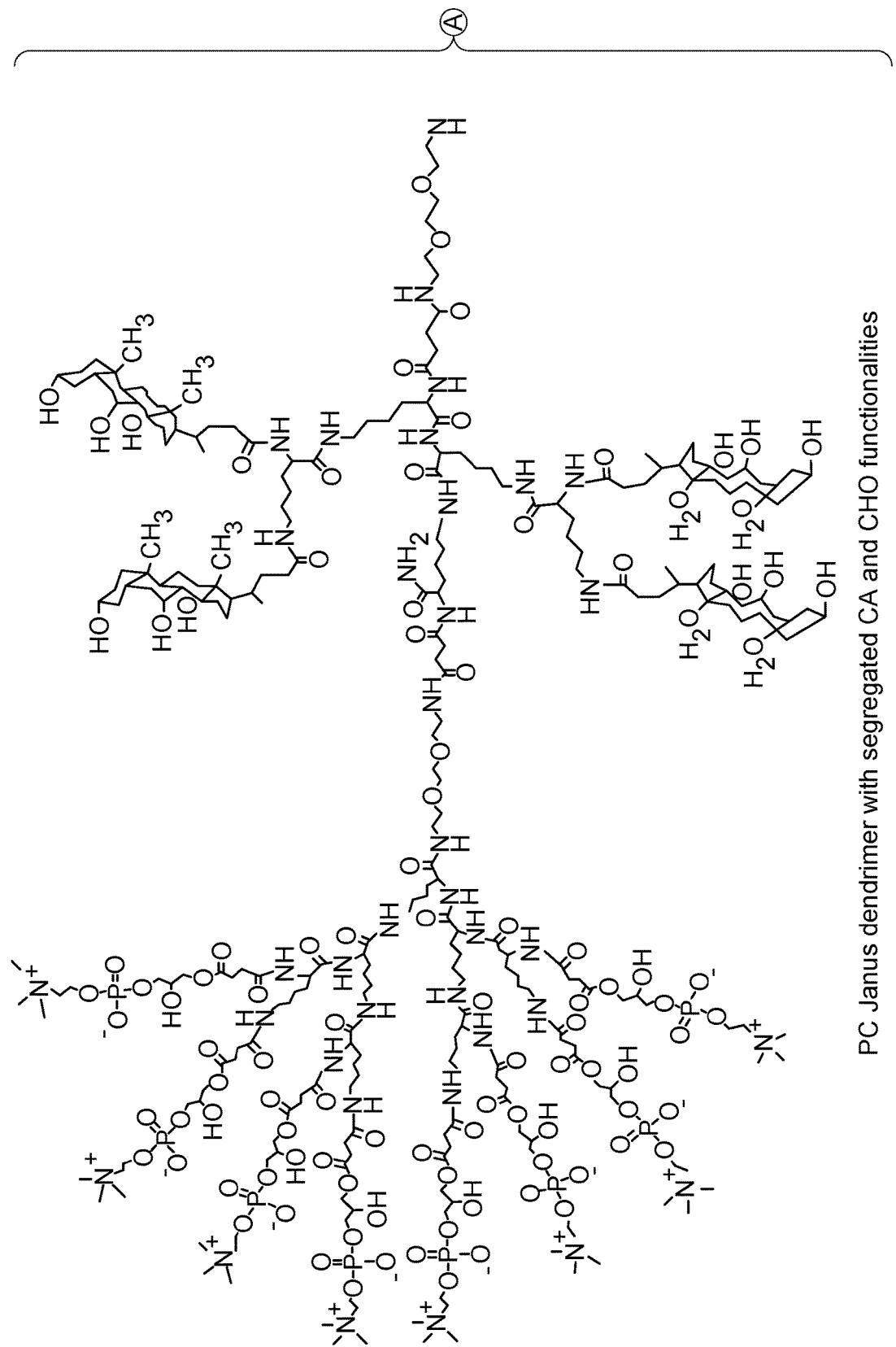
Figure 26:
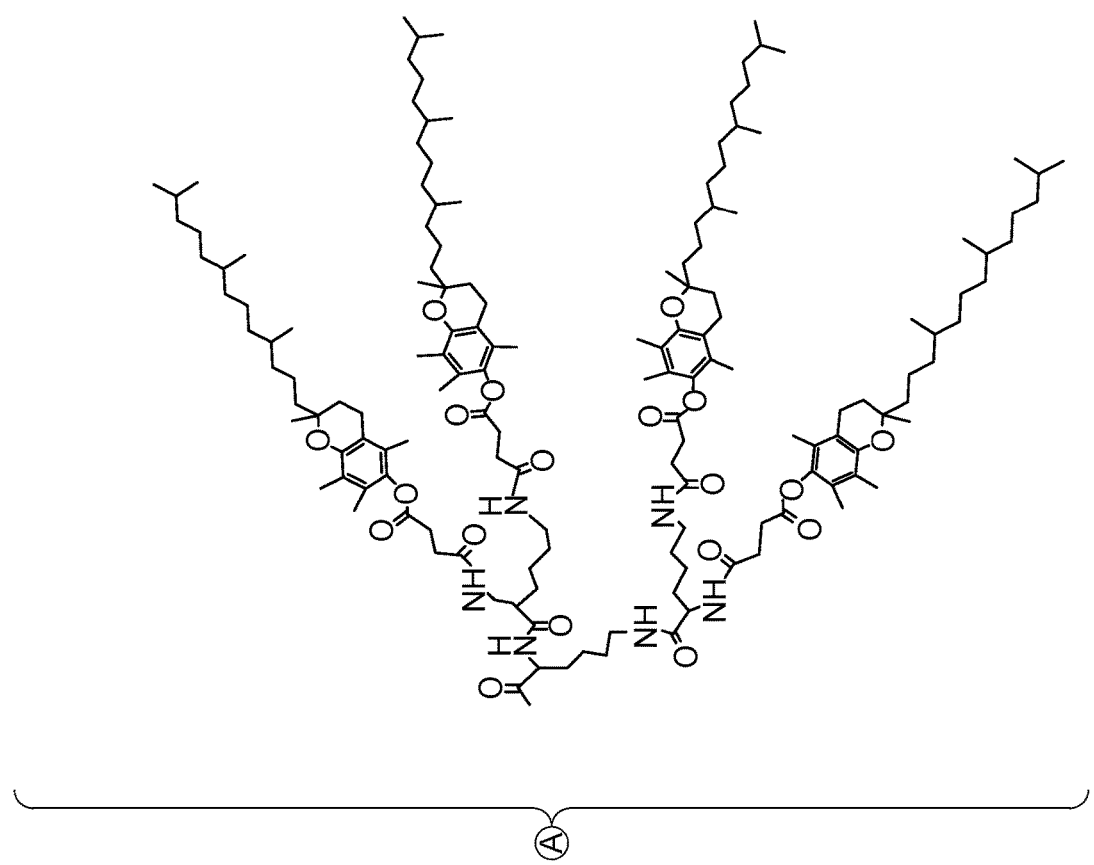
Figure 27:
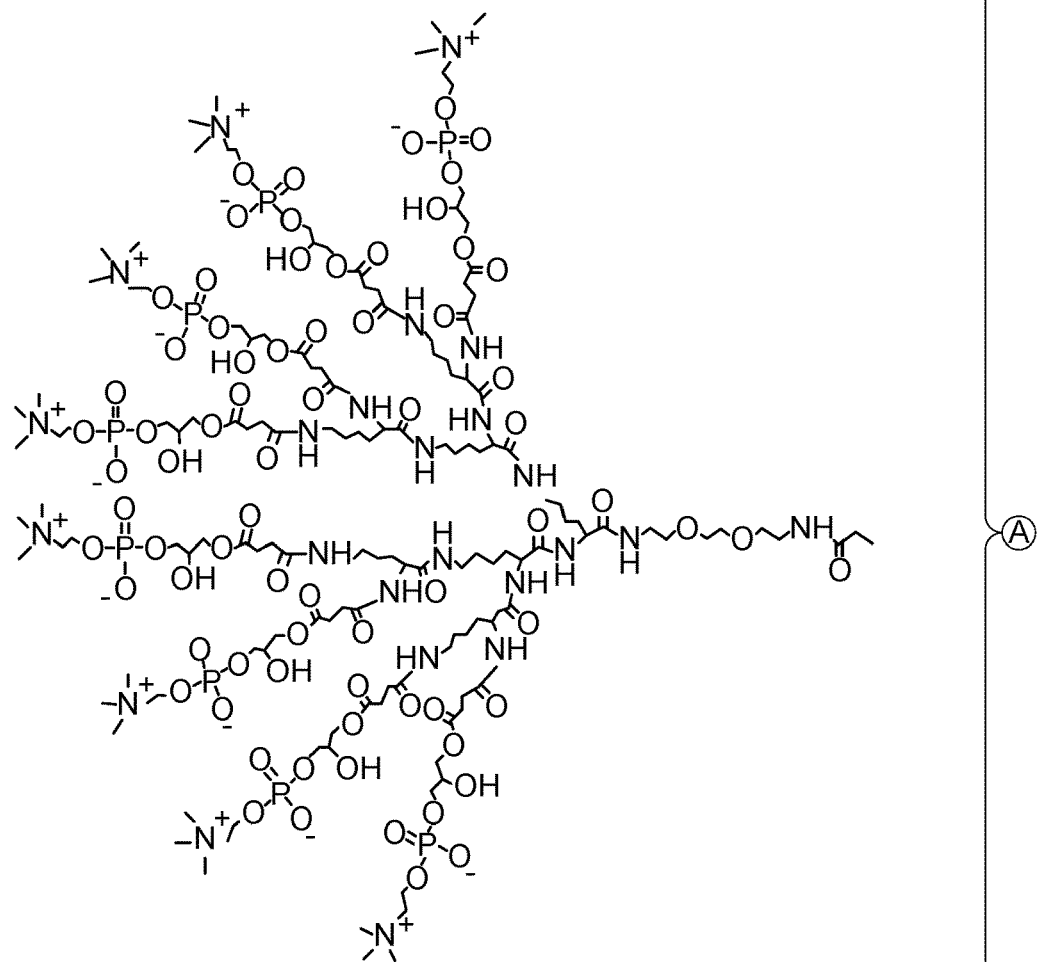
Figure 27:
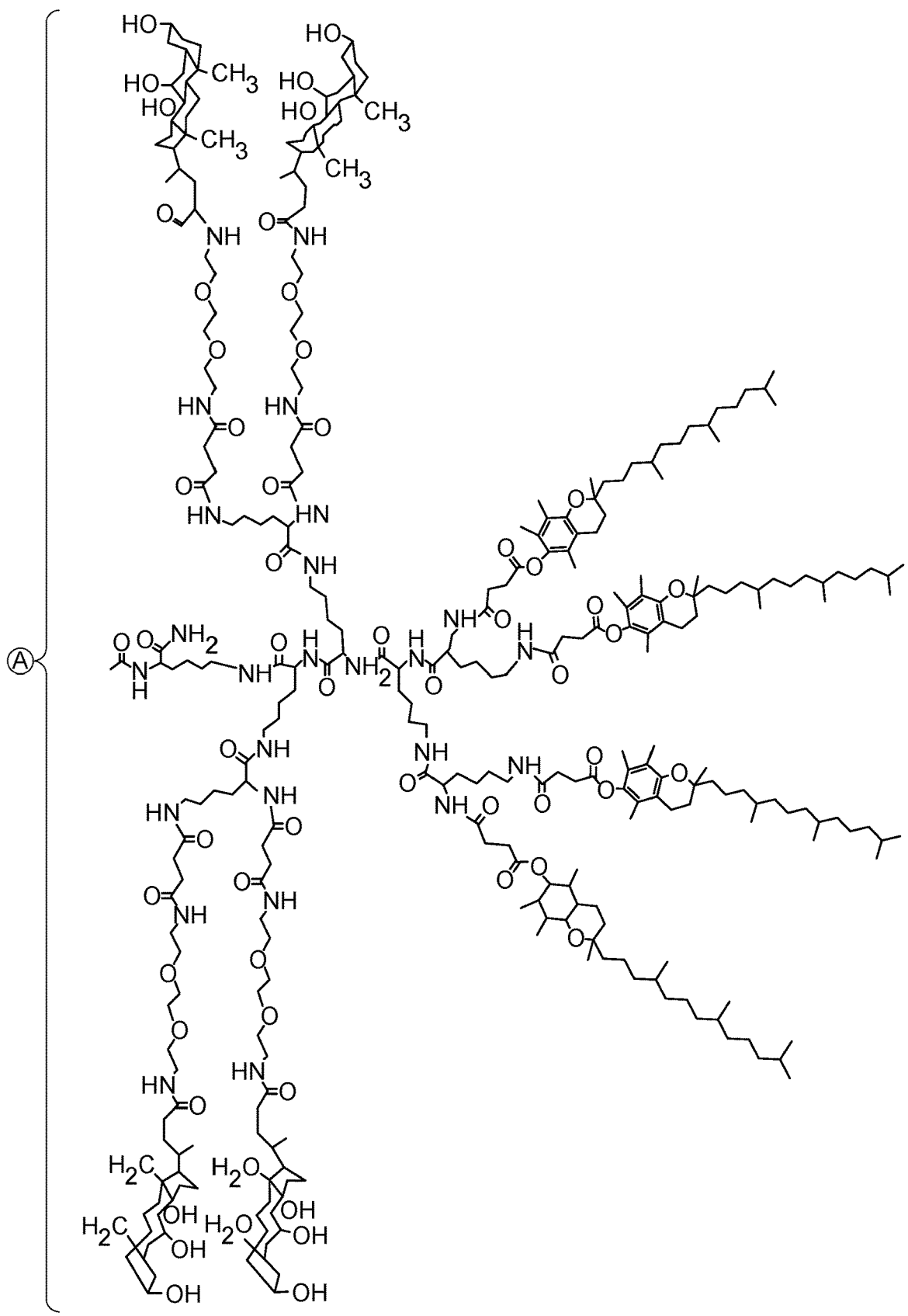
Figure 28:
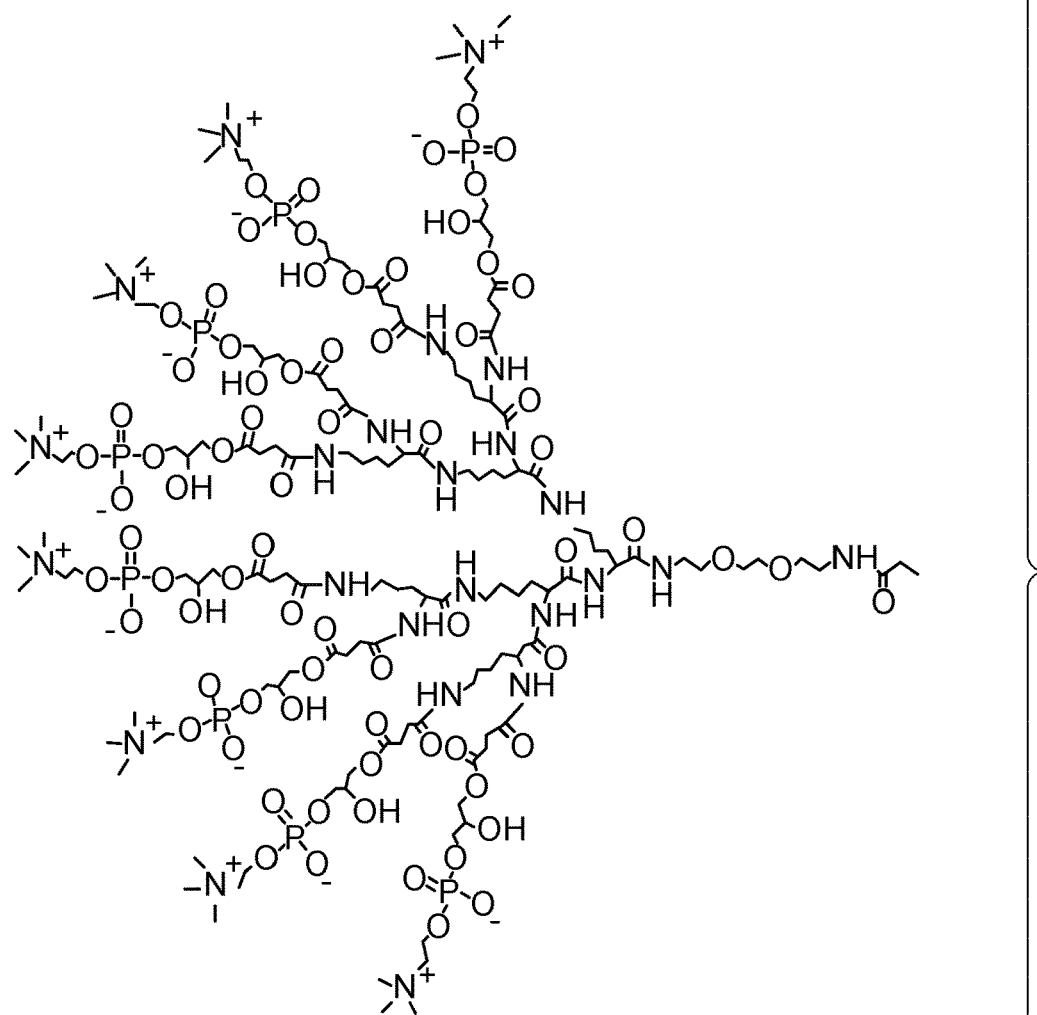
Figure 28:
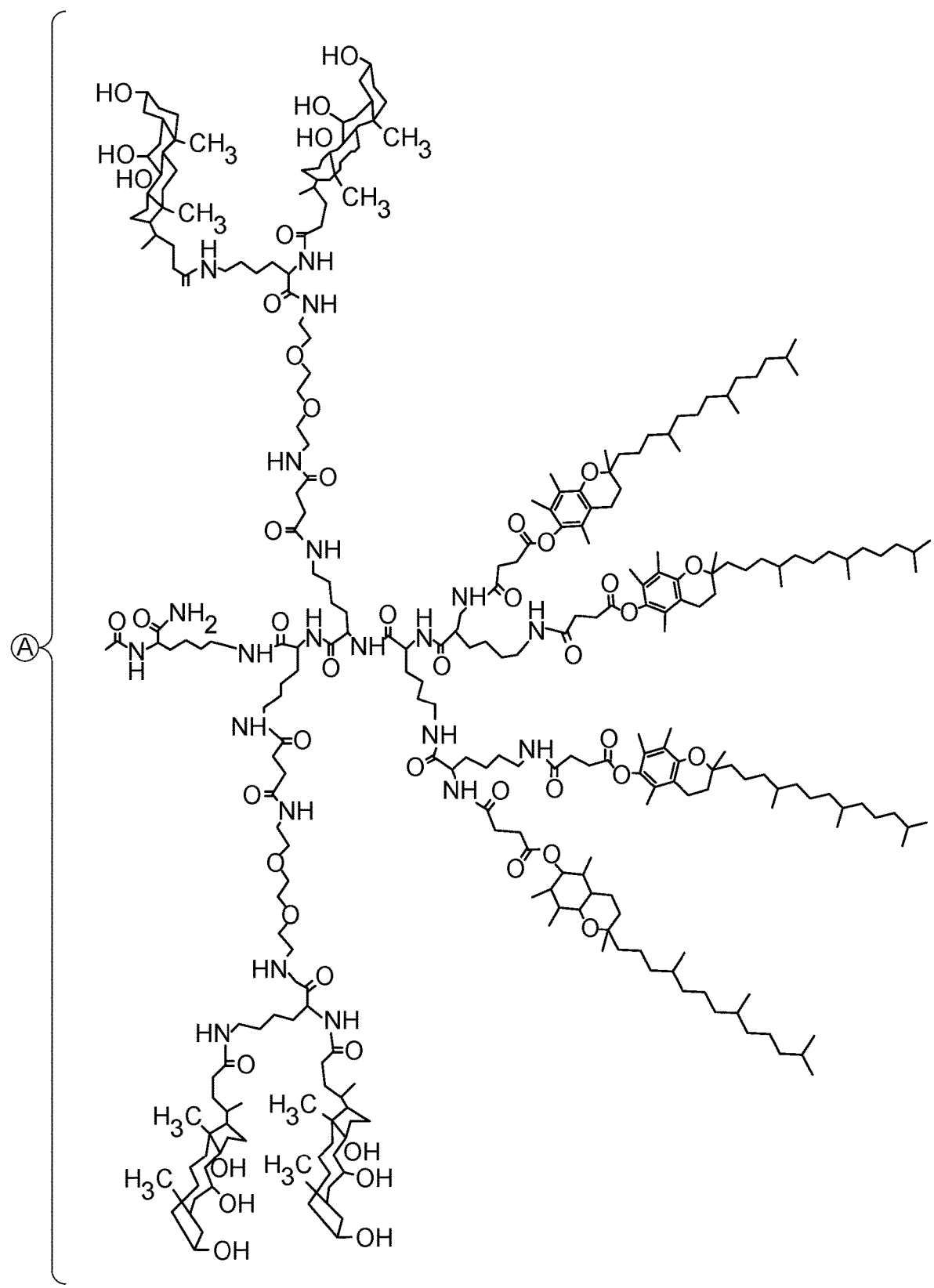
Figure 29:
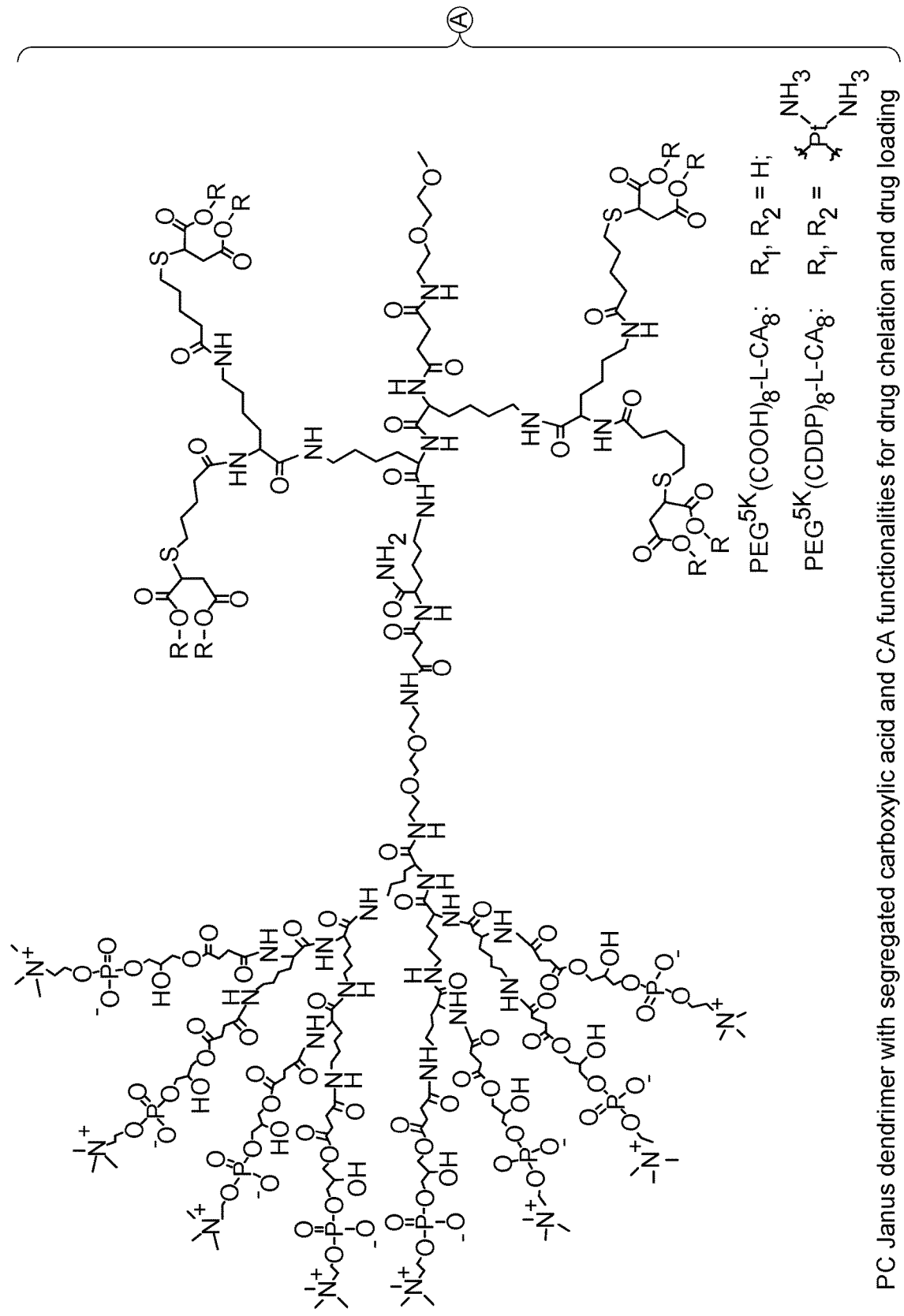
Figure 29:
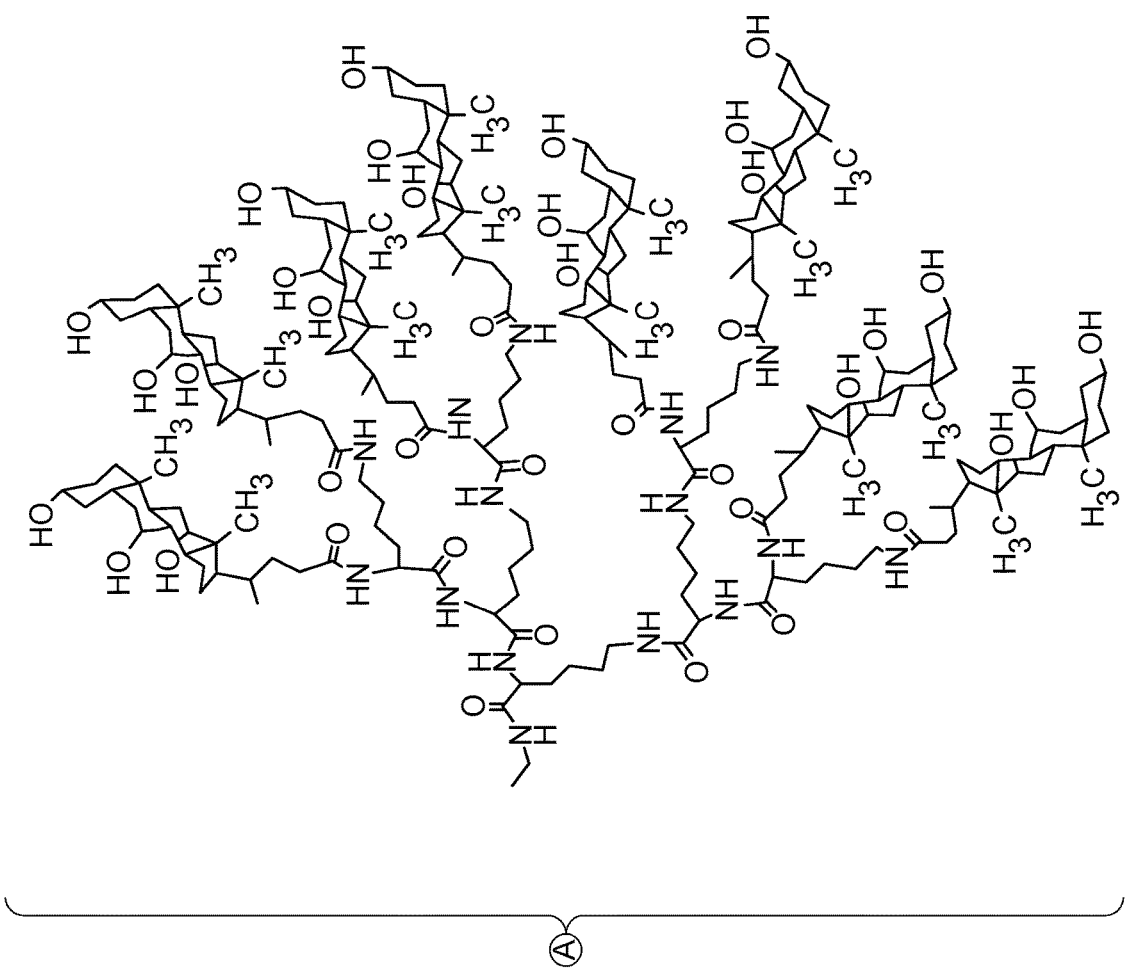
Figure 30:
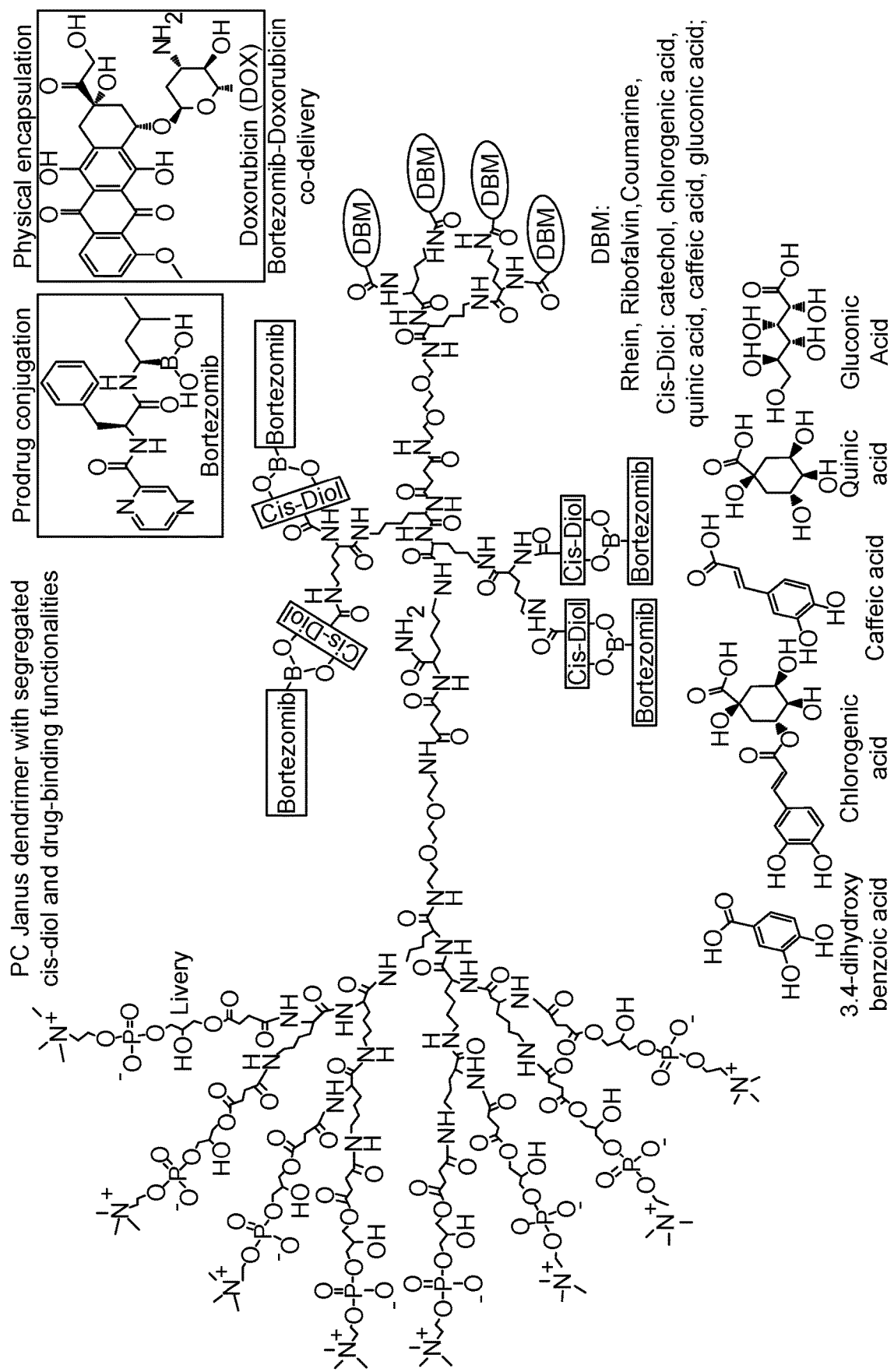
Figure 31:
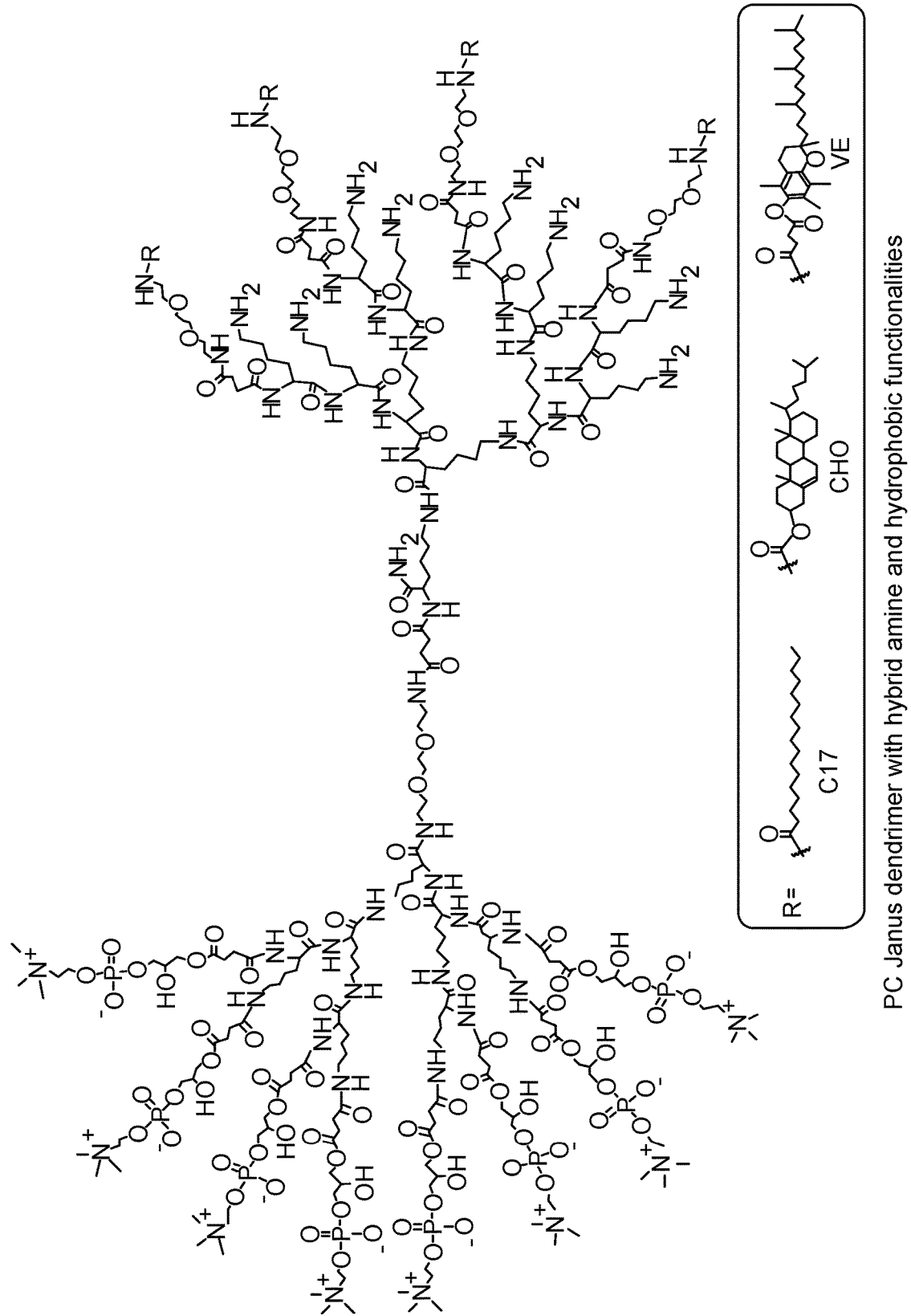
Figure 32:
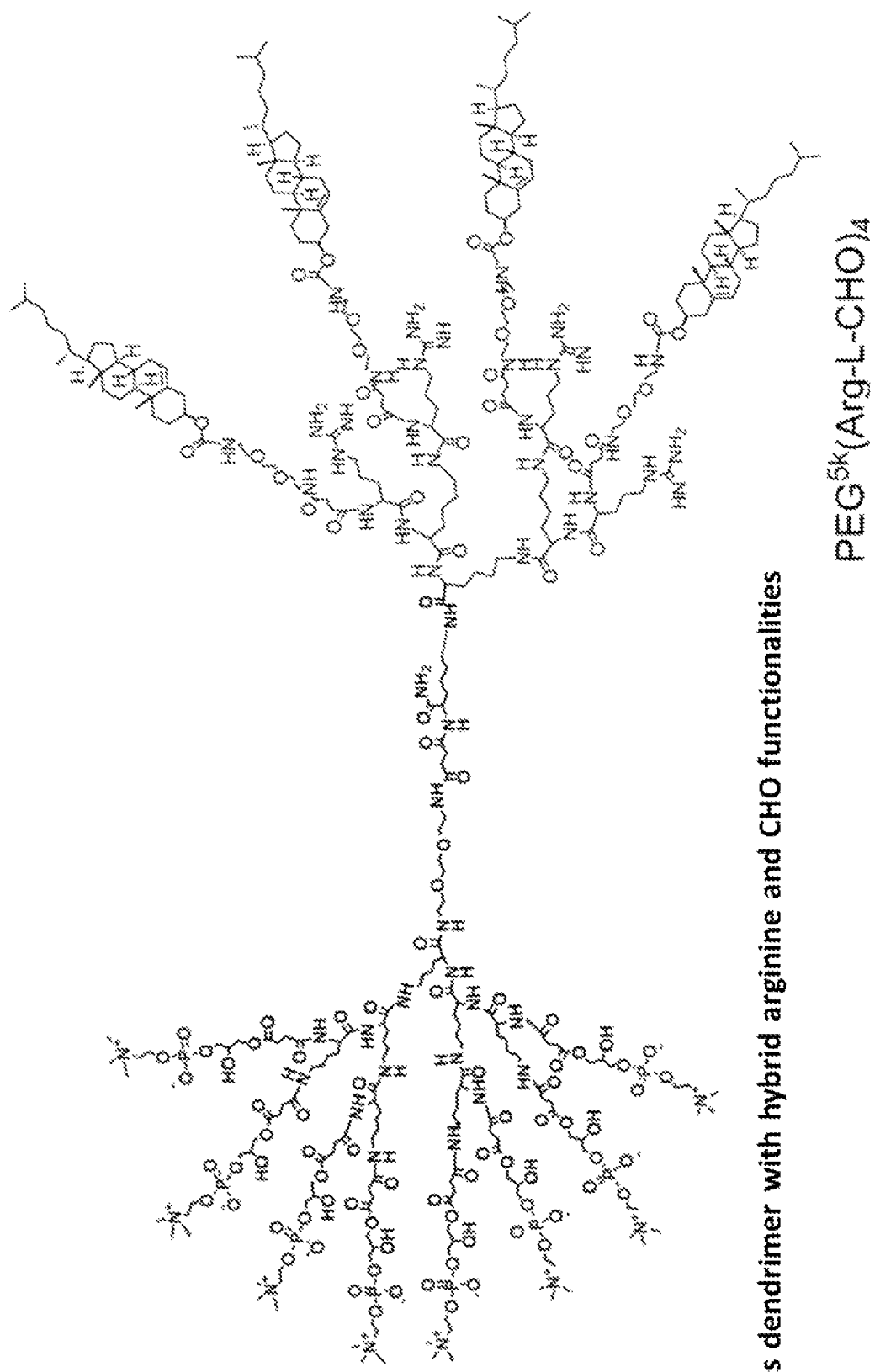
Figure 33:
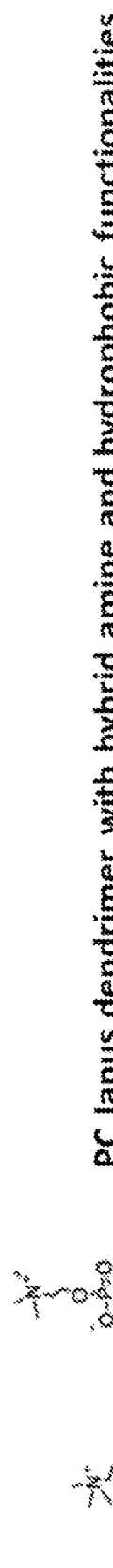
Figure 34:
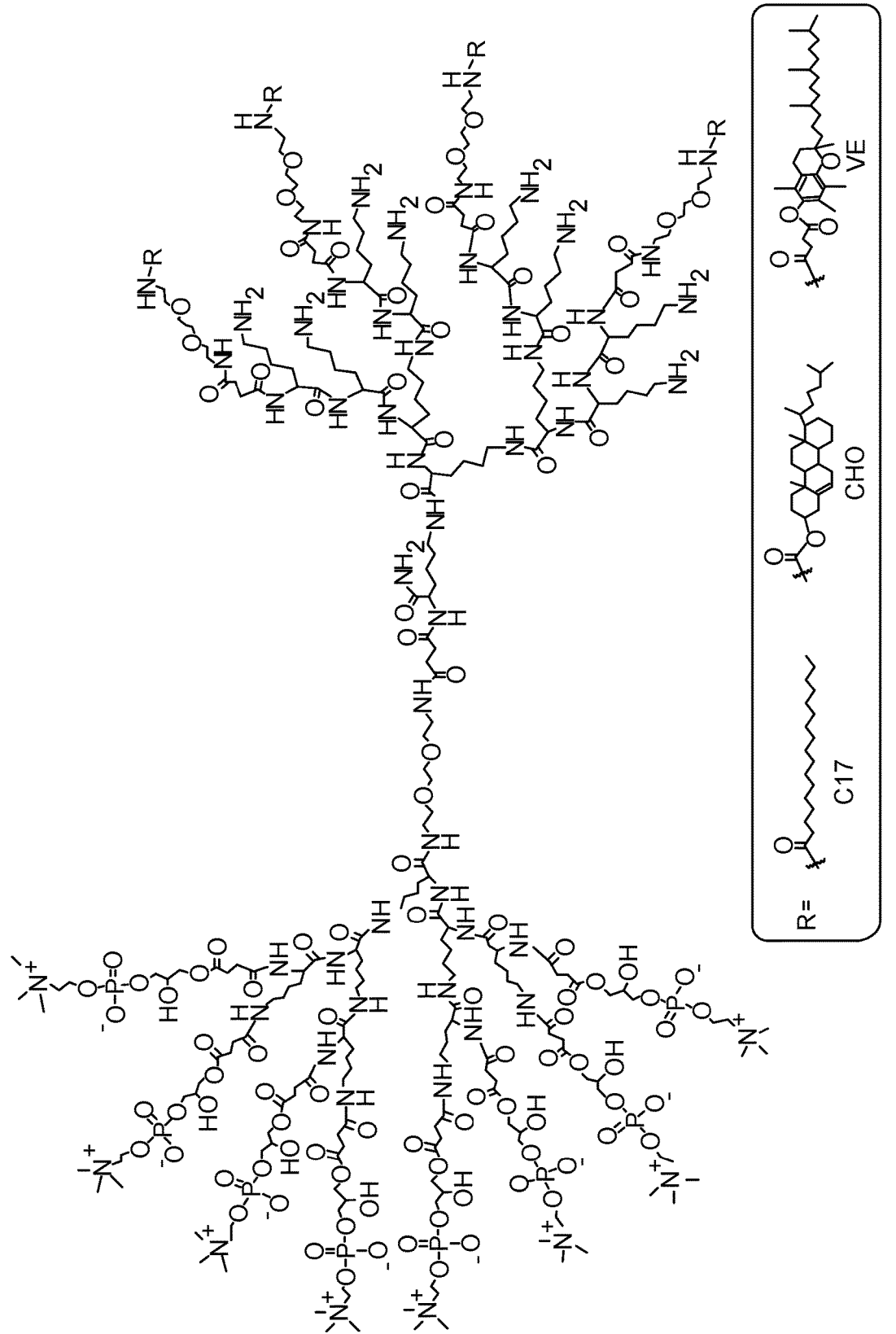
Figure 35:
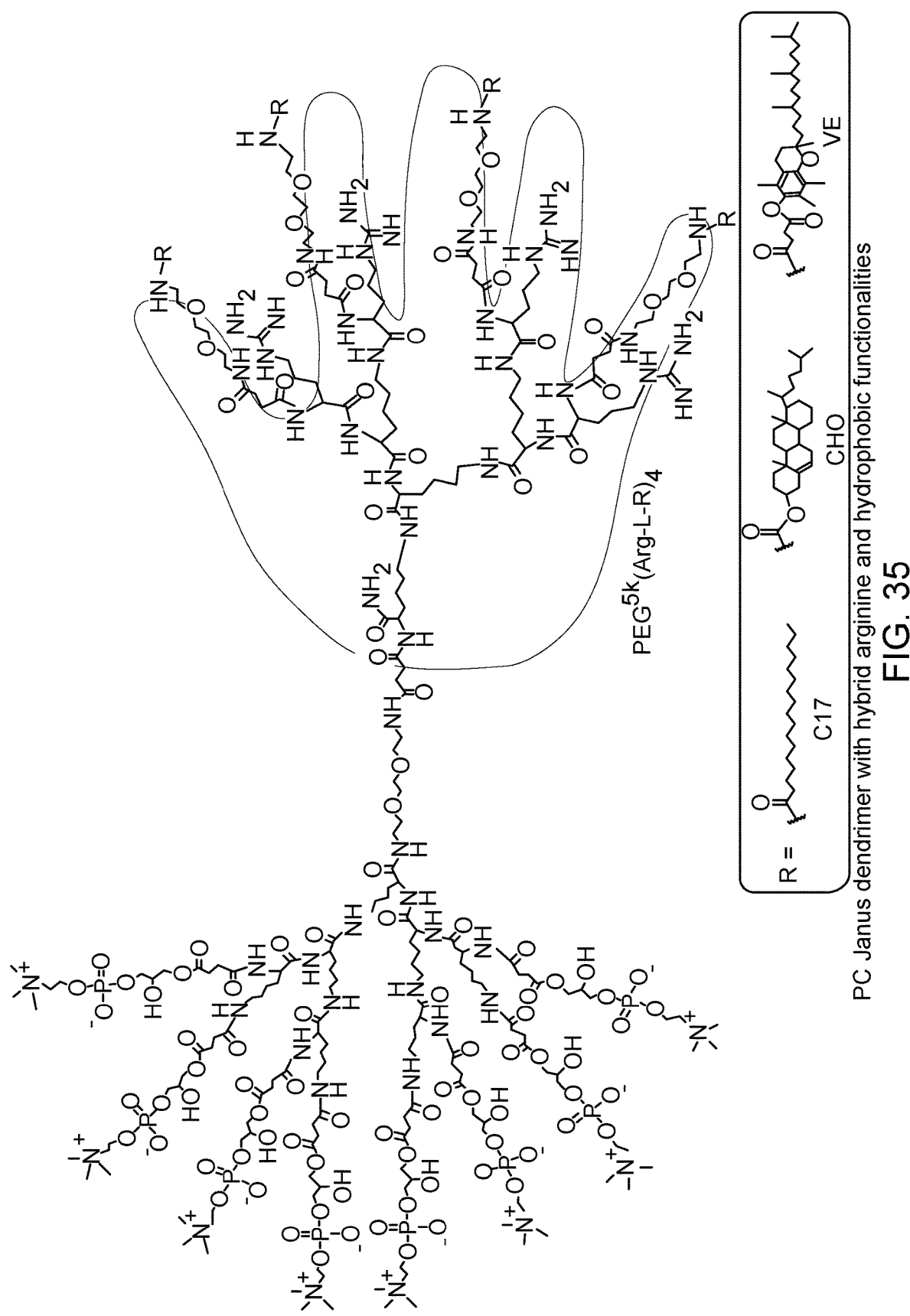
Figure 36:
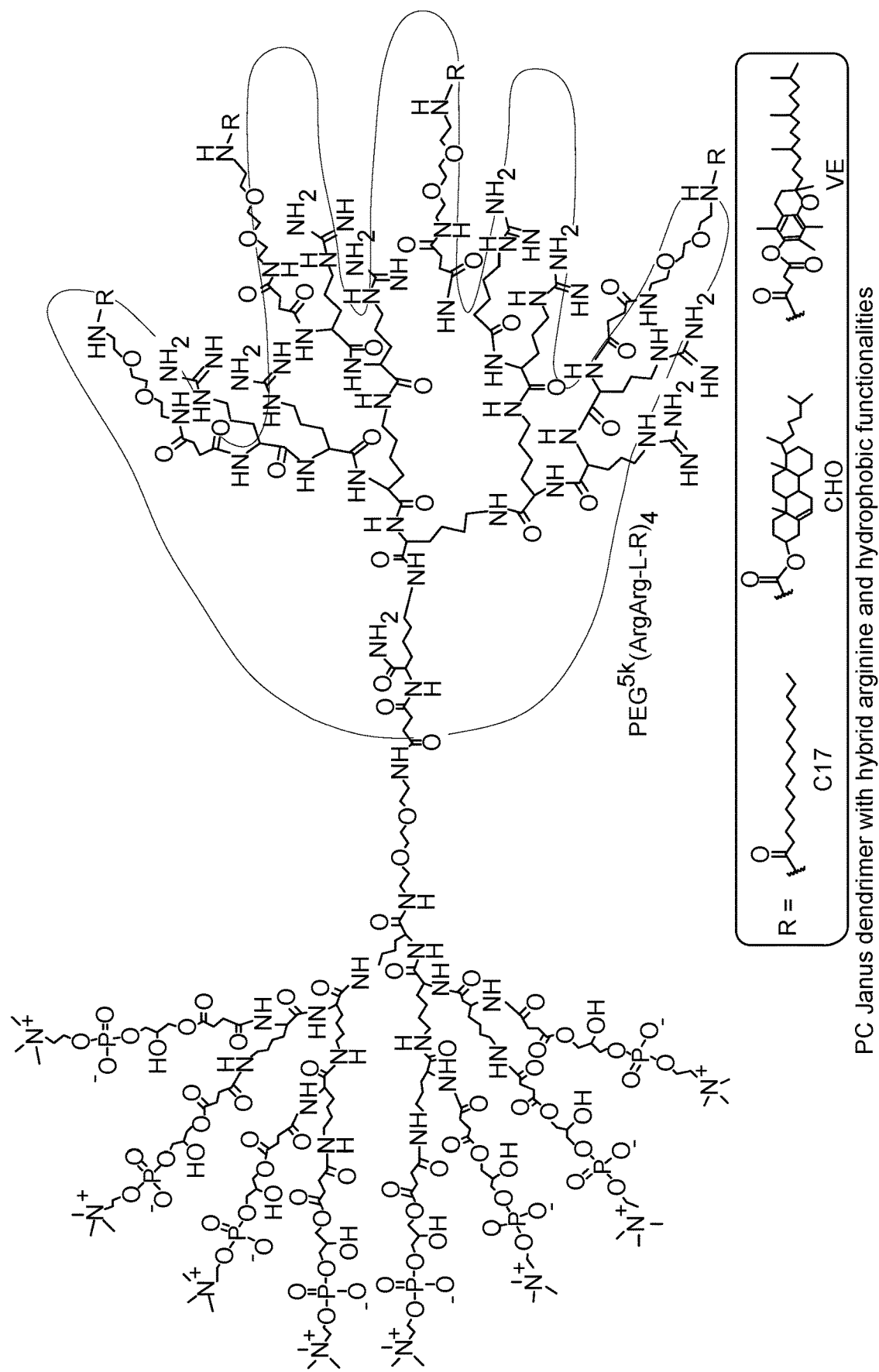

FIGS. 11 and 12 provide examples of dendrimers comprising one or more zwitterionic dendrons (also referred to herein as Janus-type amphiphiles) that can be used for protein or drug binding FIG. 13 show drug release from a dendrimers comprising one or more zwitterionic dendrons of the present disclosure.

Example 4

The following provides examples of uses of dendrimers of the present disclosure.

Animals—BALB/c mice, at age 8 weeks, were purchased from Jackson Laboratory (Bar Harbor, Maine). All animals were kept under pathogen-free conditions according to Association for Assessment and Accreditation of Laboratory Animal Care (AAALAC) guidelines and were allowed to acclimatize for at least 6 days prior to any experiments. All animal experiments were performed in compliance with institutional guidelines and according to protocol approved by the Committee for the Humane Use of Animals of State University of New York Upstate Medical University.

Figure 37A:
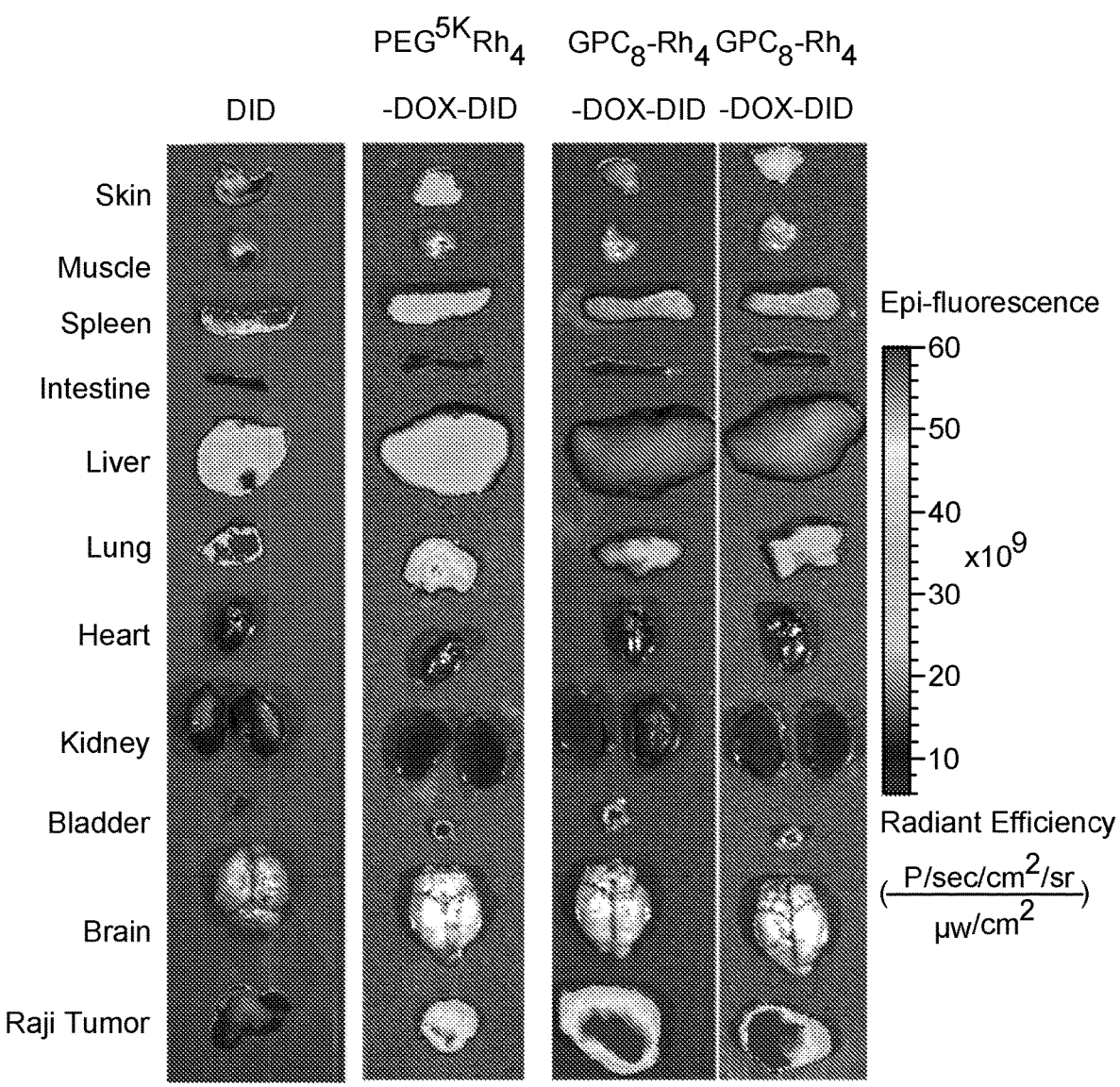
FIG. 37 shows (A) Ex vivo NIRF optical images and (B) the quantitative analysis of fluorescent signals in the major organs and tumor of Raji lymphoma-bearing mice injected intravenously with free DiD and DiD-DOX co-loaded nanoformulations in telodendrimer $PEG^{5k}Rh_4$ and Janus dendrimer $GPC_8Rh_4$ formulations.
Figure 37B:
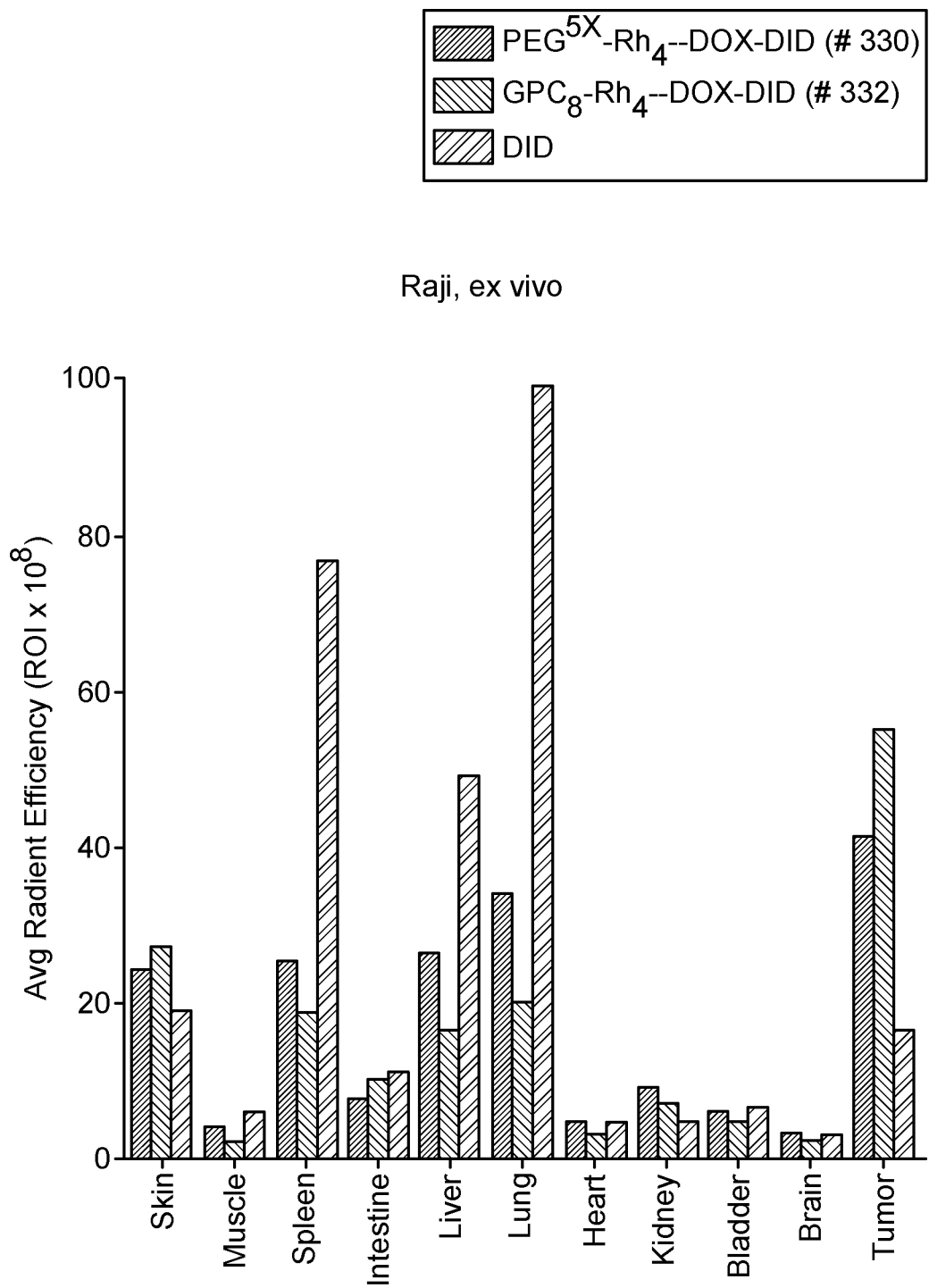
Figure 38A:
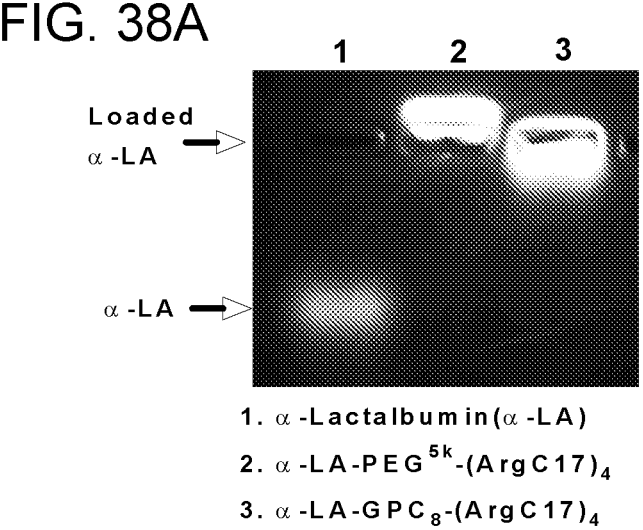
FIG. 38 shows pharmacokinetic studies of α-lactalbumin (α-LA) and pHLIP. (A) Agarose gel electrophoresis profile showing the loading of α-LA. Blood circulation profiles (B) and area under curves (C) for α-LA and α-LA loaded nanoparticles following intravenous administration. (D) Agarose gel electrophoresis profile of pHLIP loading. Blood circulation profiles (E) and area under curves (F) for native pHLIP and pHLIP loaded nanoparticles.
Figure 38B:
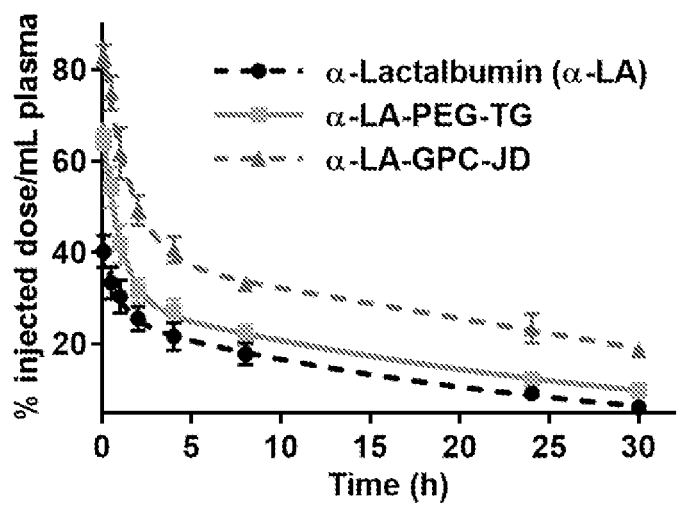
Figure 38C:
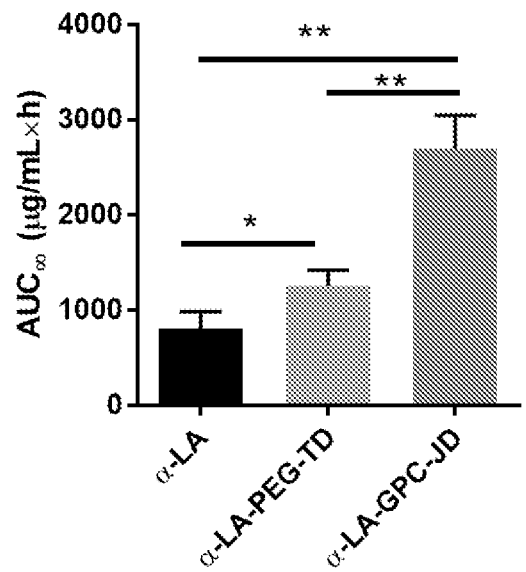
Figure 38D:
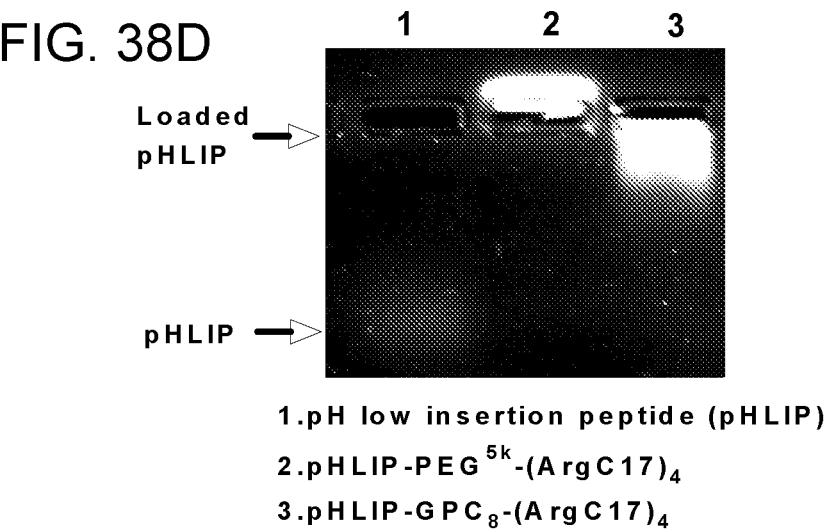
Figure 38E:
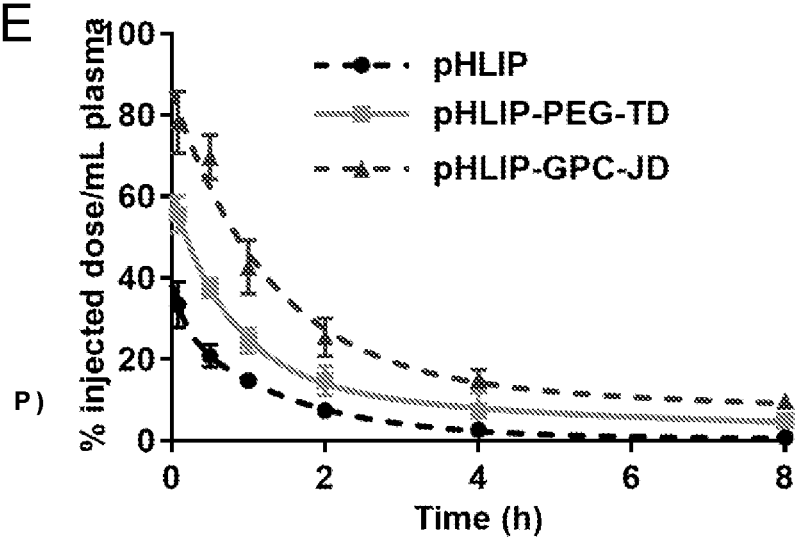
Figure 38F:
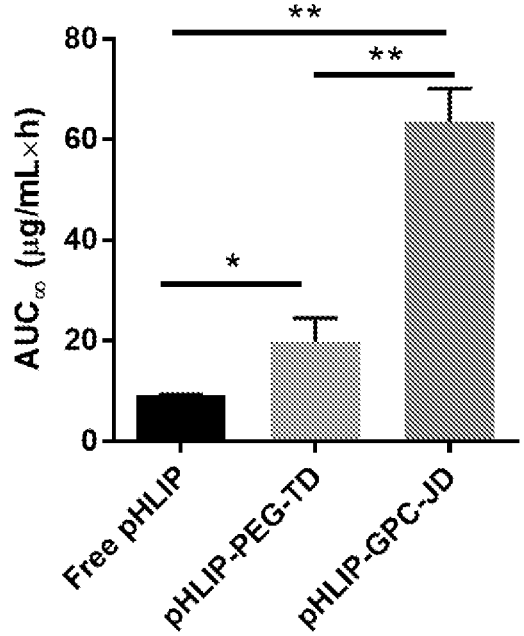
Figure 39A:
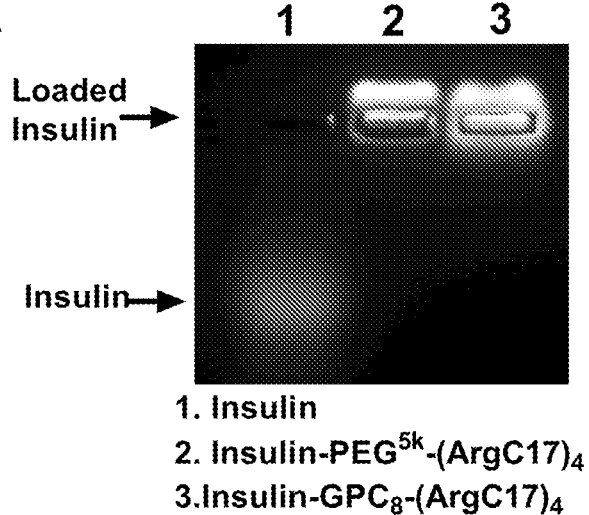
FIG. 39 shows (A) Agarose gel electrophoresis profile of insulin loading by TD and JD nanocarriers. (B) Blood glucose response of normal mice after subcutaneous injection with to free insulin or insulin-loaded nanoparticles at insulin dose of 2 IU/kg, (C) Quantification of hypoglycemia index (*P<0.05, P<0.01, *P<0.001).
Figure 39B:
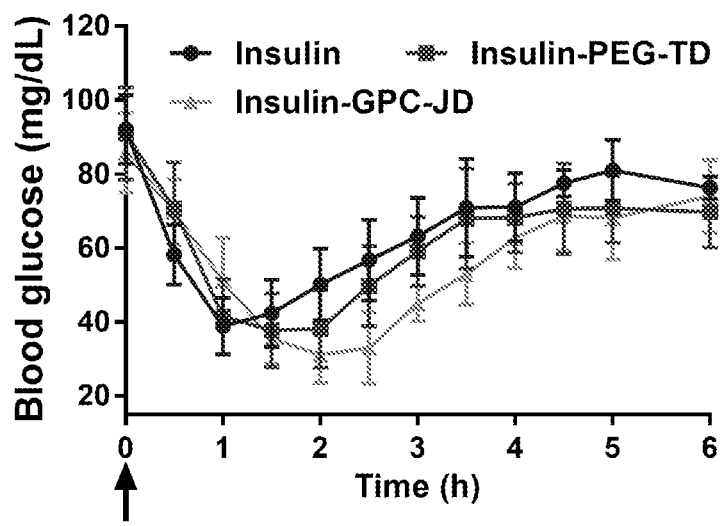
Figure 39C:
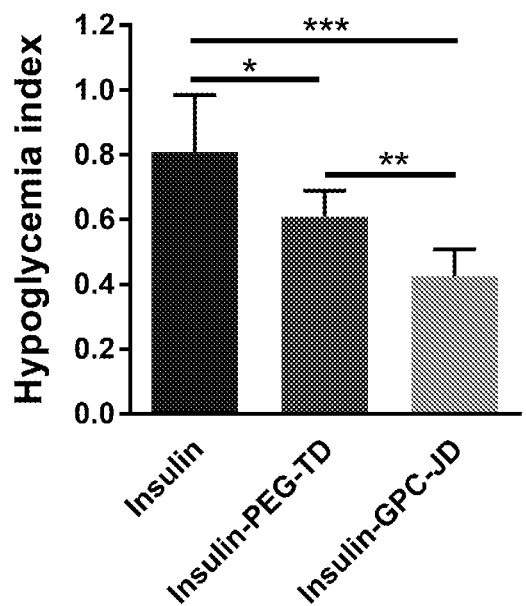

Biodistribution of zwitterionic nanocarrier $GPC_8$-$Rh_4$ loaded with doxorubicin and DiD was examined. Nude mice bearing human Raji lymphoma xenografts (approximately 500 $mm^3$) were randomized into three groups (3 mice per group). DiD (a hydrophobic near-infrared (NIR) cyanine dye) was encapsulated in the nanocarriers $GPC_8$-$Rh_4$ and $PEG^{5k}$-$Rh_4$ together with DOX. 100 µL DiD-NP(DOX) solution was filtered with a 0.22 µm filter to sterilize the solution before injection. An equal amount of DiD in ethanol solution was diluted with PBS, mixed with BTZ+DOX and intravenously injected. Mice were anesthetized with isoflurane and optically imaged at designed time points using an IVIS 200 (PerkinElmer) with the excitation/emission at 625/700 nm. After 72 h, the animals were sacrificed and all the major organs and tumors excised for ex vivo imaging to determine the in vivo biodistribution of nanoparticles. The associated fluorescence intensities were determined by Living Image software (Caliper Life Sciences) using operator-defined regions of interest (ROI) measurements. See FIG. 37.

A pharmocokinetic (PK) study of protein/peptide loaded in zwitterionic nanocarriers was done. See FIG. 38. The blood circulations of biomacromolecules were studied using different model compounds including peptide and protein. The PKs of native and polymer encapsulated alpha-Lactalbumin (α-LA) and pH low insertion peptide (pHLIP) [2] were studied on BALB/c mice (n=3 per group). Rhodamine B (RhB)-labeled α-LA (RB-α-LA) and pHLIP were intravenously injected at a dose of 8 mg/kg and 1 mg/kg, respectively. All animal experiments adhered to federal guidelines and were approved by the SUNY Upstate Medical University and Use Committee. For PK studies, each protein sample was administered into the mice via tail vein injection at the dose of 10 mg/kg body weight. Blood samples were collected from the tail vein at predetermined time after the injection. The blood samples were put in heparinized vials and centrifuged, and serum was collected for quantitative measurement. The fluorescent signals of RB-α-LA and pHLIP were recorded at excitation/emission of 525/580 nm and 630/671 nm, respectively.

Table 2 shows pharmacokinetic parameters of α-lactalbumin and pHLIP peptide after intravenous injections.

| PK parameter | α-LA | | | pHLIP | | |
|---|---|---|---|---|---|---|
| | Native α-LA | α-LA-PEG-TD | α-LA-GPC-JD | pHLIP | pHLIP-PEG-TD | pHLIP-GPC-JD |
| $t_{1/2}$ α $(h)^a$ | 0.025 ± 0.002 | 0.31 ± 0.19 | 0.74 ± 0.16 | 0.022 ± 0.002 | 0.048 ± 0.007 | 0.93 ± 0.27 |
| $t_{1/2}$ β $(h)^b$ | 10.3 ± 2.4 | 15.3 ± 4.0 | 30.9 ± 4.4 | 1.2 ± 0.2 | 2.8 ± 1.4 | 9.9 ± 2.9 |
| CL $(mL/h)^c$ | 21.1 ± 1.8 | 3.2 ± 2.5 | 0.72 ± 0.22 | 20.1 ± 3.3 | 7.2 ± 0.7 | 0.37 ± 0.20 |
| $AUC_∞$ (µg/mL × h)$^d$ | 805.9 ± 179.6 | 1253.5 ± 161.2 | 2762.2 ± 291.8 | 9.4 ± 0.3 | 19.8 ± 4.7 | 63.5 ± 6.7 |

$^a$Initial half-life.
$^b$Terminal elimination half-life.
$^c$Apparent total clearance of the protein from plasma.
$^d$Area under curve from time zero to infinity.

The blood sugar control of the insulin and insulin nanoformulations following subcutaneous administration were evaluated on healthy BALB/c mice (n=6 per group) at insulin dose of 2 IU/kg. The mice were fasted for overnight before the injection with only water access and stay fasted during the test. The nanoformulation were produced at a mass ratio of 1/10 of insulin to polymer. Blood glucose levels were measured using a glucose meter (EasyTouch®, MHC Medical Products, LLC, Fairfield, OH).

It is critical to maintain the bioactivity of protein therapeutics after loaded in the nanoparticles. Insulin was loaded in JD and TD nanocarriers efficiently (FIG. 40A) and was subcutaneously injected into the fasted mice to control blood sugar level at a dose of 2 IU/kg. Reduced blood glucose levels were observed in all the groups treated with either free insulin or insulin nanoformulations (FIG. 40B), indicating release of the active form of insulin. It is noticed that insulin loaded in GPC-JD nanocarrier sustained the blood sugar level for longer time than both free insulin and insulin loaded in PEG-TD. The overall effect of insulin-elicited hypoglycemia was quantified by the hypoglycemia index, a parameter evaluating the blood glucose drop from the initial reading to the nadir value divided by the time over which this drop occurred. As shown in FIG. 40C, the hypoglycemia indexes for the insulin nanoformulation groups are significantly lower than that of the free insulin group, suggesting the reduced hypoglycemia elicited by nanotherapeutics. Insulin nanoformulation with GPC shell show extended delay of hypoglycemic response, which is likely attributed to the controlled release of insulin from GPC-JD nanocarrier.

While the disclosure has been described through specific examples, routine modifications will be apparent to those skilled in the art and such modifications are intended to be within the scope of the present disclosure.

The invention claimed is:

1. A Janus-type zwitterionic dendritic compound comprising the following structure:

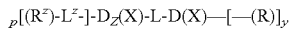
$_p[(R^z)-L^z-]-D_z(X)-L-D(X)-[-(R)]_y$ wherein $R^z$ is one or more zwitterionic groups selected from the group consisting of: a phosphorylcholine moiety (PC) and carboxybetain moiety (CB) wherein $L^z$ is optional and is a linker glycerol-succinate moiety;

$D^z$ is a nonlinear dendritic polymer moiety having a single focal group and one or more branched monomer units (X), and a plurality of end groups, wherein (X) is independently selected from the group consisting of a diamino carboxylic acid moiety, a dihydroxy carboxylic acid moiety, and a hydroxyl amino carboxylic acid moiety;

L is optional and at least one linker group or a bond selected from the group consisting of a polyethylene glycol moiety, disulfide bond moiety and acid labile moiety;

D is a nonlinear dendritic polymer moiety having a single focal group and one or more branched monomer units (X), and a plurality of end groups, wherein (X) is independently selected from the group consisting of a diamino carboxylic acid moiety, a dihydroxy carboxylic acid moiety, and a hydroxyl amino carboxylic acid moiety R is an end group of the D dendritic polymer moiety and is independently at each occurrence at least one compound selected from the group consisting of, riboflavin, chlorogenic acid, rhein, vitamin E, and cholesterol;

subscript p is an integer from 2 to 64; and subscript y is an integer from 2 to 64; and combinations thereof.

2. The compound of claim 1, wherein $R^z$ is glycerolphosphorylcholine, $D^z$ and D are nonlinear dendritic structures; X is lysine; L is

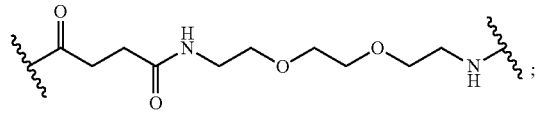 [SMILES: *NCCOCCOCCNC(=O)CCC(*)=O]

R is Rhein; subscript y is 4; subscript p is 8; and the compound has a molecular weight of 5436.30, an exact mass of 5433.15, and the chemical formula C232H353N33O99P8.

3. The compound of claim 1, wherein the compound further comprises a protein associated with the compound.

4. The compound of claim 1, wherein the compound further comprises a drug associated with the compound.

5. A nanocarrier comprising a plurality of compounds of claim 1.

6. The nanocarrier of claim 5, wherein at least one of the compounds of the plurality compounds is structurally distinct from rest of the plurality of compounds.

7. The nanocarrier of claim 5, wherein the nanocarrier further comprises one or more protein or peptides.

8. The nanocarrier of claim 5, wherein the nanocarrier further comprises a drug.

9. The nanocarrier of claim 5, wherein the nanocarrier further comprises an imaging agent.

10. A method of delivering a protein and/or drug to an individual comprising administering to the individual a compound of claim 1.

11. A method of delivering a protein and/or drug to an individual comprising administering to the individual a nanocarrier of claim 5.

* * * * *